US011285168B2

(12) United States Patent
Iba et al.

(10) Patent No.: US 11,285,168 B2
(45) Date of Patent: Mar. 29, 2022

(54) METHOD FOR SUPPRESSING TUMORS BY MIR-200 FAMILY INHIBITION

(71) Applicant: NATIONAL UNIVERSITY CORPORATION CHIBA UNIVERSITY, Chiba (JP)

(72) Inventors: Hideo Iba, Chiba (JP); Takeshi Haraguchi, Chiba (JP)

(73) Assignee: NATIONAL UNIVERSITY CORPORATION CHIBA UNIVERSITY, Chiba (JP)

( * ) Notice: Subject to any disclaimer, the term of this patent is extended or adjusted under 35 U.S.C. 154(b) by 306 days.

(21) Appl. No.: 15/763,825

(22) PCT Filed: Sep. 27, 2016

(86) PCT No.: PCT/JP2016/078345
§ 371 (c)(1),
(2) Date: Mar. 27, 2018

(87) PCT Pub. No.: WO2017/057312
PCT Pub. Date: Apr. 6, 2017

(65) Prior Publication Data
US 2018/0271895 A1 Sep. 27, 2018

(30) Foreign Application Priority Data
Sep. 28, 2015 (JP) .............................. JP2015-190419

(51) Int. Cl.
| A61K 31/7105 | (2006.01) |
| A61K 45/00 | (2006.01) |
| A61K 48/00 | (2006.01) |
| A61P 35/00 | (2006.01) |
| A61K 45/06 | (2006.01) |

(52) U.S. Cl.
CPC .......... *A61K 31/7105* (2013.01); *A61K 45/00* (2013.01); *A61K 45/06* (2013.01); *A61K 48/00* (2013.01); *A61P 35/00* (2018.01)

(58) Field of Classification Search
None
See application file for complete search history.

(56) References Cited

U.S. PATENT DOCUMENTS

| 2010/0010072 A1* | 1/2010 | Dmitrovsky | .......... | C12Q 1/6886 |
| | | | | 514/44 R |
| 2010/0273856 A1* | 10/2010 | Smith | .................... | A61P 35/00 |
| | | | | 514/44 A |
| 2010/0323903 A1* | 12/2010 | Rosenwald | .......... | C12Q 1/6886 |
| | | | | 506/7 |
| 2011/0245481 A1 | 10/2011 | Iba et al. | | |

FOREIGN PATENT DOCUMENTS

| CN | 102264898 | 11/2011 |
| EP | 2 363 467 | 9/2011 |
| JP | 2008-519606 | 6/2008 |
| JP | 2011-501949 | 1/2011 |
| WO | WO-2006/137941 | 12/2006 |
| WO | WO-2009/015071 | 1/2009 |
| WO | WO-2009/057113 | 5/2009 |
| WO | WO-2010/047216 | 4/2010 |

OTHER PUBLICATIONS

Pacurari et al. The microRNA-200 Family Targets Multiple Non-small Cell Lung Cancer Prognostic Markers in H1299 Cells and BEAS-2B cells. International Journal of Oncology, 2013. 43:548-560).*
Wu et al. MicroRNA-141 Regulates the Tumor Suppressor DLC1 in Colorectal Cancer. Neoplasma, 2015. 62(5): 705-712 (published online Aug. 3, 2015).*
Chen et al. The Roles of miR-200C in Colon Cancer and Associated Molecular Mechanisms. Tumor Biology, 2014. 35:6475-6483.*
Kim et al. Expression of microRNA miR-126 and miR-200c is Associated With Prognosis in Patients with Non-Small Cell Lung Cancer. Virchows Archives, 2014. 465:463-471.*
Korpal et al. Direct Targeting of Sec23a by miR-200s Influences Cancer Cell Secretome and Promotes Metastatic Colonization. Nature Medicine, 2011. 17(9):1101-1108.*
Sun et al., "Suppressive role of miR-502-5p in breast cancer via downregulation of TRAF2," Oncology Reports (2014) 31(5):2085-2092.
Tanaka, et al., "Induction of Epithelial-Mesenchymal Transition and Down-Regulation of miR-200c and miR-141 in Oxaliplatin-Resistant Colorectal Cancer Cells," Biological and Pharmaceutical Bulletin. (2015) 38(3): 435-40.
Tejero et al. "miR-141 and miR-200c as markers of overall survival in early stage non-small cell lung cancer adenocarcinoma," PLoS One. (2014) 9(7): e101899.
Al-Hajj et al., "Prospective identification of tumorigenic breast cancer cells," PNAS (2003) 100(7):3983-3988.
Bracken et al., "Genome-wide identification of miR-200 targets reveals a regulatory network controlling cell invasion," EMBO J (2014) 33(19):2040-2056.
Chaffer et al., "Poised chromatin at the ZEB1 promoter enables breast cancer cell plasticity and enhances tumorigenicity," Cell (2013) 154(1):61-74.
Chen et al., "The roles of miR-200c in colon cancer and associated molecular mechanisms," Tumour Biol (2014) 35(7):6475-6483.

(Continued)

Primary Examiner — James D Schultz
Assistant Examiner — Kimberly A Aron
(74) Attorney, Agent, or Firm — Morrison & Foerster LLP

(57) ABSTRACT

Tumor growth was found to be significantly suppressed in vivo by inhibiting both miRNA containing 5'-AACACUG-3' as a seed sequence and miRNA containing 5'-AAUACUG-3' as a seed sequence. The inhibition significantly altered the proportion of subpopulations of tumor cells and reduced the tumorigenicity in all subpopulations. The inhibition also exerted a remarkable tumor-shrinking effect on already-formed tumors. The present invention provides novel therapeutic potential against tumor.

8 Claims, 32 Drawing Sheets

Specification includes a Sequence Listing.

(56) References Cited

OTHER PUBLICATIONS

Chu et al., "The paradox of E-cadherin: role in response to hypoxia in the tumor microenvironment and regulation of energy metabolism," Oncotarget (2013) 4(3):446-462.
Filmore et al., "Human breast cancer cell lines contain stem-like cells that self-renew, give rise to phenotypically diverse progeny and survive chemotherapy," Breast Cancer Res (2008) 10(2):R25.
Gupta et al., "Stochastic state transitions give rise to phenotypic equilibrium in populations of cancer cells," Cell (2011) 146(4):633-644.
Haraguchi et al., "2'-OME RNA Oligo o Kiban to shita Dokuji no Niji Kozo o Motsu Shinki microRNA Sogaizai," Gene & Medicine Mook (2012) 23:169-175.
Haraguchi et al., "Dynamics and plasticity of the epithelial to mesenchymal transition induced by miR-200 family inhibition," Scientific Reports (2016) 6:21117.
Hur et al., "MicroRNA-200c modulates epithelial-to-mesenchymal transition (EMT) in human colorectal cancer metastasis," Gut (2013) 62(9):1315-1326.
International Preliminary Report on Patentability for PCT/JP2016/078345, dated Feb. 28, 2018, 20 pages (Including English translation).
International Search Report for PCT/JP2016/078345, dated Dec. 20, 2016, 4 pages (Including English translation).
Le et al., "miR-200-containing extracellular vesicles promote breast cancer cell metastasis," J Clin Invest (2014) 124(12):5109-5128.
Ma et al., "miR-9, a MYC/MYCN-activated microRNA, regulates E-cadherin and cancer metastasis," Nat Cell Biol (2010) 12(3):247-256.
Mani et al., "The epithelial-mesenchymal transition generates cells with properties of stem cells," Cell (2008) 133(4):704-715.
Marjanovic et al., "Poised with purpose cell plasticity enhances tumorigenicity," Cell Cycle (2013) 12(17):2713-2714.
Mateescu et al., "miR-141 and miR-200a act on ovarian tumorigenesis by controlling oxidative stress response," Nat Med (2011) 17(12):1627-1635.
Prat et al., "Characterization of cell lines derived from breast cancers and normal mammary tissues for the study of the intrinsic molecular subtypes," Breast Cancer Res (2013) 142(2):237-255.
Prat et al., "Phenotypic and molecular characterization of the claudin-low intrinsic subtype of breast cancer," Breast Cancer Res (2010) 12(5):R68.
Scheel et al., "Cancer stem cells and epithelial-mesenchymal transition: concepts and molecular links," Semin Cancer Biol (2012) 22(5-6):396-403.
Shimono et al., "Downregulation of miRNA-200c links breast cancer stem cells with normal stem cells," Cell (2009) 138(3):592-603.
Tsai et al., "Spatiotemporal regulation of epithelial-mesenchymal transition is essential for squamous cell carcinoma metastasis," Cancer Cell (2012) 22(6):725-736.
Tuomarila et al., Overexpression of MicroRNA-200c Predicts Poor Outcome in Patients with PR-Negative Breast Cancer, PLOS One (2014) 9(10):e109508.
Cao et al., "A new plasmid-based microRNA inhibitor system that inhibits microRNA families in transgenic mice and cells: a potential new therapeutic reagent," Gene Ther (2016) 23(6):527-542.
Haraguchi et al., "A potent 2'-O-methylated RNA-based microRNA inhibitor with unique secondary structures," Nucleic Acids Res (2012) 40(8):e58.
Comsa et al., "The Story of MCF-7 Breast Cancer Cell Line: 40 years of Experience in Research," Anticancer Research (2015) 35:3147-3154.
Park et al., "The miR-200 family determines the epithelial phenotype of cancer cells by targeting the E-cadherin repressors ZEB1 and ZEB2," Genes & Development (2008) 22:894-907.
Tan et al., "Epigenetic analysis of microRNA genes in tumors from surgically resected lung cancer patients and association with survival," Mol Carcinog. (2015) 54(Suppl1):E45-E51.
Yu et al., "Naturally existing isoforms of miR-222 have distinct functions," Nucleic Acids Res. (2017) 45(19):11371-11385.

* cited by examiner

C
|  | TuD-141/200c | TuD-NC |
|---|---|---|
| Day 0 | 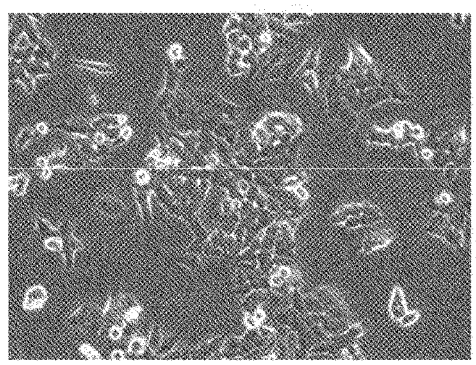 | 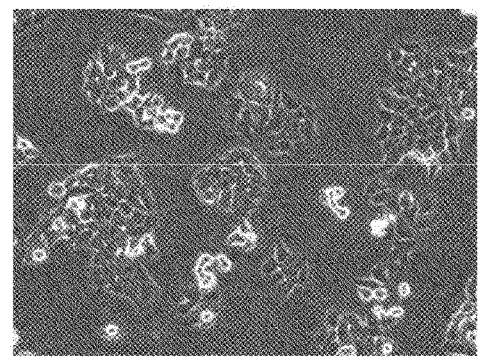 |
| Day 18 Dox+ | 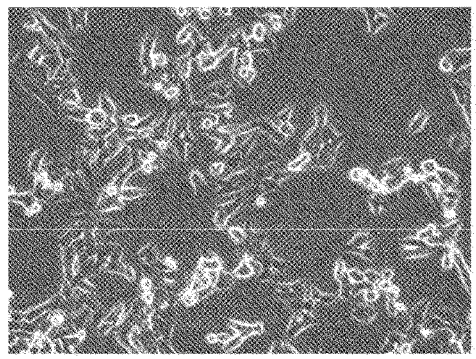 | 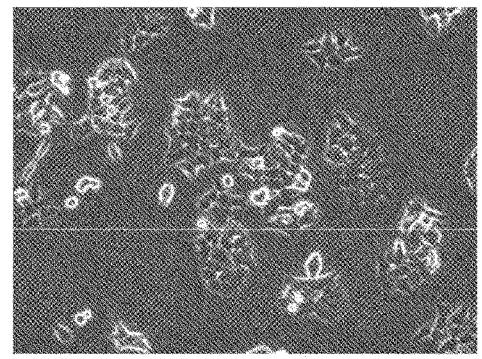 |
| Day 36 Dox+/− | 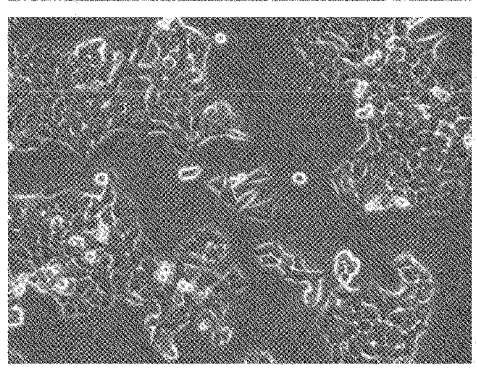 | 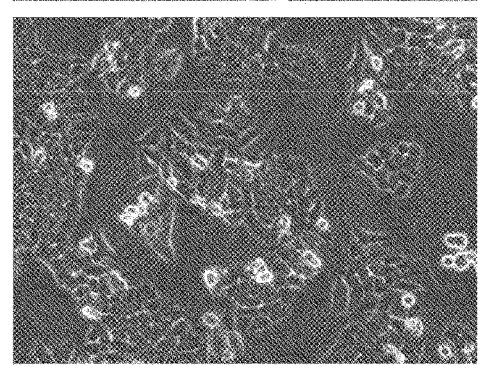 |
| Day 36 Dox+ | 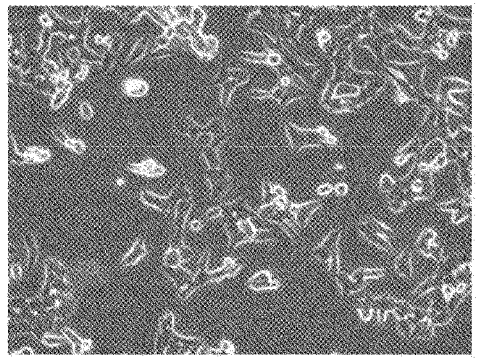 | 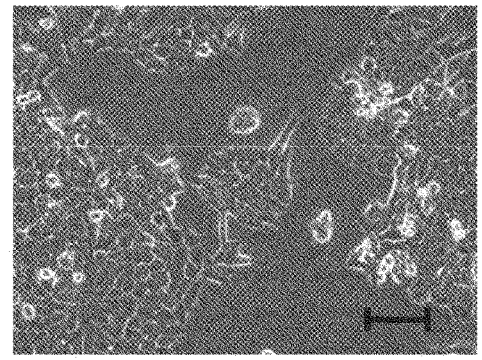 |
FIG. 3-2

A  psiCHECK2-UT

B  psiCHECK2-T21

C  psiCHECK2-T200c

D  psiCHECK2-T141

A  psiCHECK2-UT

B  psiCHECK2-T141

C  psiCHECK2-T200c

SEQUENCE LISTING

```
<160> NUMBER OF SEQ ID NOS: 77

<210> SEQ ID NO 1
<211> LENGTH: 22
<212> TYPE: RNA
<213> ORGANISM: Homo sapiens

<400> SEQUENCE: 1
uaacacuguc ugguaacgau gu                                                22

<210> SEQ ID NO 2
<211> LENGTH: 22
<212> TYPE: RNA
<213> ORGANISM: Homo sapiens

<400> SEQUENCE: 2
uaacacuguc ugguaaagau gg                                                22

<210> SEQ ID NO 3
<211> LENGTH: 22
<212> TYPE: RNA
<213> ORGANISM: Homo sapiens

<400> SEQUENCE: 3
uaauacugcc ugguaaugau ga                                                22

<210> SEQ ID NO 4
<211> LENGTH: 23
<212> TYPE: RNA
<213> ORGANISM: Homo sapiens

<400> SEQUENCE: 4
uaauacugcc ggguaaugau gga                                               23
```

```
<210> SEQ ID NO 5
<211> LENGTH: 22
<212> TYPE: RNA
<213> ORGANISM: Homo sapiens

<400> SEQUENCE: 5
uaauacuguc ugguaaaacc gu                                             22

<210> SEQ ID NO 6
<211> LENGTH: 26
<212> TYPE: RNA
<213> ORGANISM: Artificial
<220> FEATURE:
<223> OTHER INFORMATION: Synthetic

<400> SEQUENCE: 6
ccaucuuuac cacauagaca guguua                                         26

<210> SEQ ID NO 7
<211> LENGTH: 27
<212> TYPE: RNA
<213> ORGANISM: Artificial
<220> FEATURE:
<223> OTHER INFORMATION: Synthetic

<400> SEQUENCE: 7
uccaucauua ccccacuggc aguauua                                        27

<210> SEQ ID NO 8
<211> LENGTH: 300
<212> TYPE: DNA
<213> ORGANISM: Artificial
<220> FEATURE:
<223> OTHER INFORMATION: Synthetic

<400> SEQUENCE: 8
ggatccgaac gctgacgtca tcaacccgct ccaaggaatc gcgggcccag tgtcactagg    60
cgggaacacc cagcgcgcgt gcgccctggc aggaagatgg ctgtgaggga caggggagtg   120
gcgccctgca atatttgcat gtcgctatgt gttctgggaa atcaccataa acgtgaaatg   180
tctttggatt tgggaatctt ataagttctg tatgagacca caggatgtga gggcgtcatc   240
ggagacgaca ccatccacag ccagcgtctc gatgacgccc tcacatcctt ttttgaattc   300

<210> SEQ ID NO 9
<211> LENGTH: 327
<212> TYPE: DNA
<213> ORGANISM: Artificial
<220> FEATURE:
<223> OTHER INFORMATION: Synthetic

<400> SEQUENCE: 9
ggatcctgca gtatttgcat atgcaaataa ggtggtggat cgattctgga tagtgtcaaa    60
acagccggaa atcaagtccg tttatctcaa acatttgcat tttgggaata aatgatattt   120
gcattgctgg ttaaattaga ttttagttaa atttcctgct gaagctctag tacgataagc   180
aacttgacct aagtgtaaag ttgagatttc cttcaggttt atatagcttg tgcgccgcct   240
gggtacctcg gatgtgaggg cgtcatcgga gacgacacca tccacagcca gcgtctcgat   300
gacgccctca tcctttttt tgaattc                                        327

<210> SEQ ID NO 10
<211> LENGTH: 327
```

```
<212> TYPE: DNA
<213> ORGANISM: Artificial
<220> FEATURE:
<223> OTHER INFORMATION: Synthetic

<400> SEQUENCE: 10
ggatcctgca gtatttgcat atgcaaataa ggtggtggat cgattctgga tagtgtcaaa      60
acagccggaa atcaagtccg tttatctcaa acatttgcat tttgggaata aatgatattt     120
gcattgctcc ctatcagtga tagagattaa atttccttcc ctatcagtga tagagaaagc     180
aacttgacct aagtgtaaag ttgagatttc cttcaggttt atatagctcc ctatcagtga     240
tagagactcg gatgtgaggg cgtcatcgga gacgacacca tccacagcca gcgtctcgat     300
gacgccctca catccttttt tgaattc                                         327

<210> SEQ ID NO 11
<211> LENGTH: 29
<212> TYPE: DNA
<213> ORGANISM: Artificial
<220> FEATURE:
<223> OTHER INFORMATION: Synthetic

<400> SEQUENCE: 11
tcgagtcaac atcagtctga taagctagc                                        29

<210> SEQ ID NO 12
<211> LENGTH: 29
<212> TYPE: DNA
<213> ORGANISM: Artificial
<220> FEATURE:
<223> OTHER INFORMATION: Synthetic

<400> SEQUENCE: 12
ggccgctagc ttatcagact gatgttgac                                        29

<210> SEQ ID NO 13
<211> LENGTH: 30
<212> TYPE: DNA
<213> ORGANISM: Artificial
<220> FEATURE:
<223> OTHER INFORMATION: Synthetic

<400> SEQUENCE: 13
tcgagtccat cattacccgg cagtattagc                                       30

<210> SEQ ID NO 14
<211> LENGTH: 30
<212> TYPE: DNA
<213> ORGANISM: Artificial
<220> FEATURE:
<223> OTHER INFORMATION: Synthetic

<400> SEQUENCE: 14
ggccgctaat actgccgggt aatgatggac                                       30

<210> SEQ ID NO 15
<211> LENGTH: 29
<212> TYPE: DNA
<213> ORGANISM: Artificial
<220> FEATURE:
<223> OTHER INFORMATION: Synthetic

<400> SEQUENCE: 15
tcgagccatc tttaccagac agtgttagc                                        29
```

```
<210> SEQ ID NO 16
<211> LENGTH: 29
<212> TYPE: DNA
<213> ORGANISM: Artificial
<220> FEATURE:
<223> OTHER INFORMATION: Synthetic

<400> SEQUENCE: 16
ggccgctaac actgtctggt aaagatggc                                    29

<210> SEQ ID NO 17
<211> LENGTH: 89
<212> TYPE: DNA
<213> ORGANISM: Artificial
<220> FEATURE:
<223> OTHER INFORMATION: Synthetic

<400> SEQUENCE: 17
catcaaccca tctttaccac atagacagtg ttacaagtat tctggtcaca gaatacaacc  60
catctttacc acatagacag tgttacaag                                    89

<210> SEQ ID NO 18
<211> LENGTH: 89
<212> TYPE: DNA
<213> ORGANISM: Artificial
<220> FEATURE:
<223> OTHER INFORMATION: Synthetic

<400> SEQUENCE: 18
tcatcttgta acactgtcta tgtggtaaag atgggttgta ttctgtgacc agaatacttg  60
taacactgtc tatgtggtaa agatgggtt                                    89

<210> SEQ ID NO 19
<211> LENGTH: 91
<212> TYPE: DNA
<213> ORGANISM: Artificial
<220> FEATURE:
<223> OTHER INFORMATION: Synthetic

<400> SEQUENCE: 19
catcaactcc atcattaccc cactggcagt attacaagta ttctggtcac agaatacaac  60
tccatcatta ccccactggc agtattacaa g                                 91

<210> SEQ ID NO 20
<211> LENGTH: 91
<212> TYPE: DNA
<213> ORGANISM: Artificial
<220> FEATURE:
<223> OTHER INFORMATION: Synthetic

<400> SEQUENCE: 20
tcatcttgta atactgccag tggggtaatg atggagttgt attctgtgac cagaatactt  60
gtaatactgc cagtggggta atgatggagt t                                 91

<210> SEQ ID NO 21
<211> LENGTH: 89
<212> TYPE: DNA
<213> ORGANISM: Artificial
<220> FEATURE:
<223> OTHER INFORMATION: Synthetic

<400> SEQUENCE: 21
catcaaccag actccggtga agagaatgaa ggacaagtat tctggtcaca gaatacaacc  60
```

```
agactccggt gaagagaatg aaggacaag                                        89

<210> SEQ ID NO 22
<211> LENGTH: 89
<212> TYPE: DNA
<213> ORGANISM: Artificial
<220> FEATURE:
<223> OTHER INFORMATION: Synthetic

<400> SEQUENCE: 22
tcatcttgtc cttcattctc ttcaccggag tctggttgta ttctgtgacc agaatacttg      60
tccttcattc tcttcaccgg agtctggtt                                        89

<210> SEQ ID NO 23
<211> LENGTH: 90
<212> TYPE: DNA
<213> ORGANISM: Artificial
<220> FEATURE:
<223> OTHER INFORMATION: Synthetic

<400> SEQUENCE: 23
catcaaccca tctttaccac atagacagtg ttacaagtat tctggtcaca gaatacaact      60
ccatcattac cccactggca gtattacaag                                       90

<210> SEQ ID NO 24
<211> LENGTH: 90
<212> TYPE: DNA
<213> ORGANISM: Artificial
<220> FEATURE:
<223> OTHER INFORMATION: Synthetic

<400> SEQUENCE: 24
tcatcttgta atactgccag tggggtaatg atggagttgt attctgtgac cagaatactt      60
gtaacactgt ctatgtggta aagatgggtt                                       90

<210> SEQ ID NO 25
<211> LENGTH: 105
<212> TYPE: DNA
<213> ORGANISM: Artificial
<220> FEATURE:
<223> OTHER INFORMATION: Synthetic

<400> SEQUENCE: 25
gaagactgtt tgatcctggg cctgaagctg cctgacccaa ggtgggcggg ctgggcgggg      60
gccctcgtct tacccagcag tgtttgggtg cggttgggag tctct                     105

<210> SEQ ID NO 26
<211> LENGTH: 101
<212> TYPE: DNA
<213> ORGANISM: Artificial
<220> FEATURE:
<223> OTHER INFORMATION: Synthetic

<400> SEQUENCE: 26
gaattctaag ggctggggac ctgaggcgat ggatgttgct gacacaggga caggggcctc      60
catcattacc cggcagtatt agagactccc aaccgcaccc a                         101

<210> SEQ ID NO 27
<211> LENGTH: 487
<212> TYPE: DNA
<213> ORGANISM: Artificial
<220> FEATURE:
```

<223> OTHER INFORMATION: Synthetic

<400> SEQUENCE: 27

| ggatccgacg ccgccatctc taggcccgcg ccggcccct cgcacagact tgtgggagaa | 60 |
| gctcggctac tcccctgccc cggttaattt gcatataata tttcctagta actatagagg | 120 |
| cttaatgtgc gataaaagac agataatctg ttcttttaa tactagctac attttacatg | 180 |
| ataggcttgg atttctataa gagatacaaa tactaaatta ttattttaaa aaacagcaca | 240 |
| aaaggaaact caccctaact gtaaagtaat tgtgtgtttt gagactataa atatcccttg | 300 |
| gagaaaagcc ttgtttgtag caactggtga gcgcgcaccg tagttctctg tcggccggcc | 360 |
| ctgggtccat cttccagtac agtgttggat ggtctaattg tgaagctcct aacactgtct | 420 |
| ggtaaagatg gctcccgggt gggttctctc ggcagtaacc ttcagggagc cctgaagacc | 480 |
| agaattc | 487 |

<210> SEQ ID NO 28
<211> LENGTH: 483
<212> TYPE: DNA
<213> ORGANISM: Artificial
<220> FEATURE:
<223> OTHER INFORMATION: Synthetic

<400> SEQUENCE: 28

| ggatccgacg ccgccatctc taggcccgcg ccggcccct cgcacagact tgtgggagaa | 60 |
| gctcggctac tcccctgccc cggttaattt gcatataata tttcctagta actatagagg | 120 |
| cttaatgtgc gataaaagac agataatctg ttcttttaa tactagctac attttacatg | 180 |
| ataggcttgg atttctataa gagatacaaa tactaaatta ttattttaaa aaacagcaca | 240 |
| aaaggaaact caccctaact gtaaagtaat tgtgtgtttt gagactataa atatcccttg | 300 |
| gagaaaagcc ttgtttgcat ccccaccctc tgagaaaaag atcctcagac aatccatgtg | 360 |
| cttctcttgt ccttcattcc accggagtct gtctcatacc caaccagatt tcagtggagt | 420 |
| gaagttcagg aggcatggag ctgacaacca tgaggcctcg gcagccaccg ccaccacgaa | 480 |
| ttc | 483 |

<210> SEQ ID NO 29
<211> LENGTH: 29
<212> TYPE: DNA
<213> ORGANISM: Artificial
<220> FEATURE:
<223> OTHER INFORMATION: Synthetic

<400> SEQUENCE: 29

| tcgagccatc tttaccagac agtgttagc | 29 |

<210> SEQ ID NO 30
<211> LENGTH: 29
<212> TYPE: DNA
<213> ORGANISM: Artificial
<220> FEATURE:
<223> OTHER INFORMATION: Synthetic

<400> SEQUENCE: 30

| ggccgctaac actgtctggt aaagatggc | 29 |

<210> SEQ ID NO 31
<211> LENGTH: 30
<212> TYPE: DNA
<213> ORGANISM: Artificial

<220> FEATURE:
<223> OTHER INFORMATION: Synthetic

<400> SEQUENCE: 31
tcgagtccat cattacccgg cagtattagc          30

<210> SEQ ID NO 32
<211> LENGTH: 30
<212> TYPE: DNA
<213> ORGANISM: Artificial
<220> FEATURE:
<223> OTHER INFORMATION: Synthetic

<400> SEQUENCE: 32
ggccgctaat actgccgggt aatgatggac          30

<210> SEQ ID NO 33
<211> LENGTH: 29
<212> TYPE: DNA
<213> ORGANISM: Artificial
<220> FEATURE:
<223> OTHER INFORMATION: Synthetic

<400> SEQUENCE: 33
tcgagcagac tccggtggaa tgaaggagc           29

<210> SEQ ID NO 34
<211> LENGTH: 29
<212> TYPE: DNA
<213> ORGANISM: Artificial
<220> FEATURE:
<223> OTHER INFORMATION: Synthetic

<400> SEQUENCE: 34
ggccgctcct tcattccacc ggagtctgc           29

<210> SEQ ID NO 35
<211> LENGTH: 20
<212> TYPE: DNA
<213> ORGANISM: Artificial
<220> FEATURE:
<223> OTHER INFORMATION: Synthetic

<400> SEQUENCE: 35
cacaccagaa gccagtggtc                     20

<210> SEQ ID NO 36
<211> LENGTH: 20
<212> TYPE: DNA
<213> ORGANISM: Artificial
<220> FEATURE:
<223> OTHER INFORMATION: Synthetic

<400> SEQUENCE: 36
aactgcacag ggagcaacta                     20

<210> SEQ ID NO 37
<211> LENGTH: 20
<212> TYPE: DNA
<213> ORGANISM: Artificial
<220> FEATURE:
<223> OTHER INFORMATION: Synthetic

<400> SEQUENCE: 37
acatcaagta ccgccacgag                     20

<210> SEQ ID NO 38
<211> LENGTH: 21
<212> TYPE: DNA
<213> ORGANISM: Artificial
<220> FEATURE:
<223> OTHER INFORMATION: Synthetic

<400> SEQUENCE: 38
gcatttggtg ctgatctgtc c                                              21

<210> SEQ ID NO 39
<211> LENGTH: 20
<212> TYPE: DNA
<213> ORGANISM: Artificial
<220> FEATURE:
<223> OTHER INFORMATION: Synthetic

<400> SEQUENCE: 39
gcctgaacaa cggattgagc                                                20

<210> SEQ ID NO 40
<211> LENGTH: 20
<212> TYPE: DNA
<213> ORGANISM: Artificial
<220> FEATURE:
<223> OTHER INFORMATION: Synthetic

<400> SEQUENCE: 40
atcgaaggag agccattcgc                                                20

<210> SEQ ID NO 41
<211> LENGTH: 20
<212> TYPE: DNA
<213> ORGANISM: Artificial
<220> FEATURE:
<223> OTHER INFORMATION: Synthetic

<400> SEQUENCE: 41
gcagtaacct tcagggagcc                                                20

<210> SEQ ID NO 42
<211> LENGTH: 20
<212> TYPE: DNA
<213> ORGANISM: Artificial
<220> FEATURE:
<223> OTHER INFORMATION: Synthetic

<400> SEQUENCE: 42
gattcgtccc ccatccagag                                                20

<210> SEQ ID NO 43
<211> LENGTH: 20
<212> TYPE: DNA
<213> ORGANISM: Artificial
<220> FEATURE:
<223> OTHER INFORMATION: Synthetic

<400> SEQUENCE: 43
tgtaagtgag gagcaccgag                                                20

<210> SEQ ID NO 44
<211> LENGTH: 20
<212> TYPE: DNA
<213> ORGANISM: Artificial
<220> FEATURE:
<223> OTHER INFORMATION: Synthetic

```
<400> SEQUENCE: 44
tggagagaaa ctgggctacc                                              20

<210> SEQ ID NO 45
<211> LENGTH: 22
<212> TYPE: DNA
<213> ORGANISM: Artificial
<220> FEATURE:
<223> OTHER INFORMATION: Synthetic

<400> SEQUENCE: 45
gattgcaggg ggcacatcac ta                                           22

<210> SEQ ID NO 46
<211> LENGTH: 20
<212> TYPE: DNA
<213> ORGANISM: Artificial
<220> FEATURE:
<223> OTHER INFORMATION: Synthetic

<400> SEQUENCE: 46
caaagagggc gaaggcatca                                              20

<210> SEQ ID NO 47
<211> LENGTH: 21
<212> TYPE: DNA
<213> ORGANISM: Artificial
<220> FEATURE:
<223> OTHER INFORMATION: Synthetic

<400> SEQUENCE: 47
tggcgcagat cgatttgaat a                                            21

<210> SEQ ID NO 48
<211> LENGTH: 20
<212> TYPE: DNA
<213> ORGANISM: Artificial
<220> FEATURE:
<223> OTHER INFORMATION: Synthetic

<400> SEQUENCE: 48
ccgtccgaga gatgctgtag                                              20

<210> SEQ ID NO 49
<211> LENGTH: 21
<212> TYPE: DNA
<213> ORGANISM: Artificial
<220> FEATURE:
<223> OTHER INFORMATION: Synthetic

<400> SEQUENCE: 49
tctttcaatg acaacgcagc a                                            21

<210> SEQ ID NO 50
<211> LENGTH: 21
<212> TYPE: DNA
<213> ORGANISM: Artificial
<220> FEATURE:
<223> OTHER INFORMATION: Synthetic

<400> SEQUENCE: 50
ttgggtctct tcttccacct g                                            21

<210> SEQ ID NO 51
```

```
<211> LENGTH: 20
<212> TYPE: DNA
<213> ORGANISM: Artificial
<220> FEATURE:
<223> OTHER INFORMATION: Synthetic

<400> SEQUENCE: 51
tacaccccat cccagacgaa                                                    20

<210> SEQ ID NO 52
<211> LENGTH: 24
<212> TYPE: DNA
<213> ORGANISM: Artificial
<220> FEATURE:
<223> OTHER INFORMATION: Synthetic

<400> SEQUENCE: 52
gaatgtgtct tggtctctgg tagc                                               24

<210> SEQ ID NO 53
<211> LENGTH: 22
<212> TYPE: DNA
<213> ORGANISM: Artificial
<220> FEATURE:
<223> OTHER INFORMATION: Synthetic

<400> SEQUENCE: 53
gctggaattg ttgtgctggt ta                                                 22

<210> SEQ ID NO 54
<211> LENGTH: 20
<212> TYPE: DNA
<213> ORGANISM: Artificial
<220> FEATURE:
<223> OTHER INFORMATION: Synthetic

<400> SEQUENCE: 54
aagatgtctt cgtcccacgc                                                    20

<210> SEQ ID NO 55
<211> LENGTH: 20
<212> TYPE: DNA
<213> ORGANISM: Artificial
<220> FEATURE:
<223> OTHER INFORMATION: Synthetic

<400> SEQUENCE: 55
acgccgagag ctacacgttc                                                    20

<210> SEQ ID NO 56
<211> LENGTH: 20
<212> TYPE: DNA
<213> ORGANISM: Artificial
<220> FEATURE:
<223> OTHER INFORMATION: Synthetic

<400> SEQUENCE: 56
tgaatcgggt gtcgagggaa                                                    20

<210> SEQ ID NO 57
<211> LENGTH: 20
<212> TYPE: DNA
<213> ORGANISM: Artificial
<220> FEATURE:
<223> OTHER INFORMATION: Synthetic

<400> SEQUENCE: 57
```
atttccatcc tgcgcgtgaa            20

<210> SEQ ID NO 58
<211> LENGTH: 20
<212> TYPE: DNA
<213> ORGANISM: Artificial
<220> FEATURE:
<223> OTHER INFORMATION: Synthetic

<400> SEQUENCE: 58
aaaagttgtt tggcctggcg            20

<210> SEQ ID NO 59
<211> LENGTH: 20
<212> TYPE: DNA
<213> ORGANISM: Artificial
<220> FEATURE:
<223> OTHER INFORMATION: Synthetic

<400> SEQUENCE: 59
caccaaccat catcccgaca            20

<210> SEQ ID NO 60
<211> LENGTH: 20
<212> TYPE: DNA
<213> ORGANISM: Artificial
<220> FEATURE:
<223> OTHER INFORMATION: Synthetic

<400> SEQUENCE: 60
tctgtgttag ccgccttcag            20

<210> SEQ ID NO 61
<211> LENGTH: 20
<212> TYPE: DNA
<213> ORGANISM: Artificial
<220> FEATURE:
<223> OTHER INFORMATION: Synthetic

<400> SEQUENCE: 61
aggaggaaat ggctcgtcac            20

<210> SEQ ID NO 62
<211> LENGTH: 21
<212> TYPE: DNA
<213> ORGANISM: Artificial
<220> FEATURE:
<223> OTHER INFORMATION: Synthetic

<400> SEQUENCE: 62
aggcagagaa atcctgctct c            21

<210> SEQ ID NO 63
<211> LENGTH: 20
<212> TYPE: DNA
<213> ORGANISM: Artificial
<220> FEATURE:
<223> OTHER INFORMATION: Synthetic

<400> SEQUENCE: 63
ggagtccgca gtcttacgag            20

<210> SEQ ID NO 64
<211> LENGTH: 20
<212> TYPE: DNA

```
<213> ORGANISM: Artificial
<220> FEATURE:
<223> OTHER INFORMATION: Synthetic

<400> SEQUENCE: 64
tggaggacct ggtagaggaa                                              20

<210> SEQ ID NO 65
<211> LENGTH: 20
<212> TYPE: DNA
<213> ORGANISM: Artificial
<220> FEATURE:
<223> OTHER INFORMATION: Synthetic

<400> SEQUENCE: 65
ggacccacac tggcgagaag                                              20

<210> SEQ ID NO 66
<211> LENGTH: 20
<212> TYPE: DNA
<213> ORGANISM: Artificial
<220> FEATURE:
<223> OTHER INFORMATION: Synthetic

<400> SEQUENCE: 66
acattcggga gaaggtccga                                              20

<210> SEQ ID NO 67
<211> LENGTH: 23
<212> TYPE: DNA
<213> ORGANISM: Artificial
<220> FEATURE:
<223> OTHER INFORMATION: Synthetic

<400> SEQUENCE: 67
cgaactggac acacatacag tga                                          23

<210> SEQ ID NO 68
<211> LENGTH: 20
<212> TYPE: DNA
<213> ORGANISM: Artificial
<220> FEATURE:
<223> OTHER INFORMATION: Synthetic

<400> SEQUENCE: 68
ggaatggagc agcggtagtc                                              20

<210> SEQ ID NO 69
<211> LENGTH: 21
<212> TYPE: DNA
<213> ORGANISM: Artificial
<220> FEATURE:
<223> OTHER INFORMATION: Synthetic

<400> SEQUENCE: 69
actttcctcc tgaggctttg g                                            21

<210> SEQ ID NO 70
<211> LENGTH: 20
<212> TYPE: DNA
<213> ORGANISM: Artificial
<220> FEATURE:
<223> OTHER INFORMATION: Synthetic

<400> SEQUENCE: 70
tgcttggatc tgggggtaga                                              20
```

<210> SEQ ID NO 71
<211> LENGTH: 22
<212> TYPE: DNA
<213> ORGANISM: Artificial
<220> FEATURE:
<223> OTHER INFORMATION: Synthetic

<400> SEQUENCE: 71
actttgtcaa gctcatttcc tg                                           22

<210> SEQ ID NO 72
<211> LENGTH: 22
<212> TYPE: DNA
<213> ORGANISM: Artificial
<220> FEATURE:
<223> OTHER INFORMATION: Synthetic

<400> SEQUENCE: 72
ctctcttcct cttgtgctct tg                                           22

<210> SEQ ID NO 73
<211> LENGTH: 123
<212> TYPE: RNA
<213> ORGANISM: Artificial
<220> FEATURE:
<223> OTHER INFORMATION: Synthetic

<400> SEQUENCE: 73
ggaugugagg gcgucaucaa cccaucuuua ccacauagac aguguuacaa guauucgggu    60
cacagaauac aacuccauca uuaccccacu ggcaguauua caagaugacg cccucacauc   120
cuu                                                                123

<210> SEQ ID NO 74
<211> LENGTH: 243
<212> TYPE: DNA
<213> ORGANISM: Homo sapiens

<400> SEQUENCE: 74
ctgcagtatt tagcatgccc cacccatctg caaggcattc tggatagtgt caaaacagcc    60
ggaaatcaag tccgtttatc tcaaacttta gcattttggg aataaatgat atttgctatg   120
ctggttaaat tagattttag ttaaatttcc tgctgaagct ctagtacgat aagcaacttg   180
acctaagtgt aaagttgaga tttccttcag gtttatatag cttgtgcgcc gcctgggtac   240
ctc                                                                243

<210> SEQ ID NO 75
<211> LENGTH: 244
<212> TYPE: DNA
<213> ORGANISM: Artificial
<220> FEATURE:
<223> OTHER INFORMATION: Synthetic

<400> SEQUENCE: 75
ctgcagtatt tgcatatgca aataaggtgg tggatcgatt ctggatagtg tcaaaacagc    60
cggaaatcaa gtccgtttat ctcaaacatt tgcattttgg gaataaatga tatttgcatt   120
gctggttaaa ttagatttta gttaaatttc ctgctgaagc tctagtacga taagcaactt   180
gacctaagtg taaagttgag atttccttca ggtttatata gcttgtgcgc cgcctgggta   240
cctc                                                               244

```
<210> SEQ ID NO 76
<211> LENGTH: 243
<212> TYPE: DNA
<213> ORGANISM: Artificial
<220> FEATURE:
<223> OTHER INFORMATION: Synthetic

<400> SEQUENCE: 76
tgcagtattt gcatatgcaa ataaggtggt ggatcgattc tggatagtgt caaaacagcc      60
ggaaatcaag tccgtttatc tcaaacattt gcattttggg aataaatgat atttgcattg     120
ctccctatca gtgatagaga ttaaatttcc ttccctatca gtgatagaga aagcaacttg     180
acctaagtgt aaagttgaga tttccttcag gtttatatag ctccctatca gtgatagaga     240
ctc                                                                   243

<210> SEQ ID NO 77
<211> LENGTH: 258
<212> TYPE: DNA
<213> ORGANISM: Artificial
<220> FEATURE:
<223> OTHER INFORMATION: Synthetic

<400> SEQUENCE: 77
tccctatcag tgatagagag tatttgcata tgcaaataag gtggtggatc gatccctatc      60
agtgatagag aagccggaaa ttccctatca gtgatagaga catttgcatt ttgggaataa     120
atgatatttg cattgctccc tatcagtgat agagattaaa tttccttccc tatcagtgat     180
agagaaagca acttgaccta agtgtaaagt tgagatttcc ttcaggttta tatagctccc     240
tatcagtgat agagactc                                                  258
```

METHOD FOR SUPPRESSING TUMORS BY MIR-200 FAMILY INHIBITION

CROSS-REFERENCE TO RELATED APPLICATIONS

This application is the national phase of PCT application PCT/JP2016/078345 having an international filing date of Sep. 27, 2016, which claims benefit of Japanese patent application No. 2015-190419 filed Sep. 28, 2015. The contents of the above patent applications are incorporated by reference herein in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 532842001200SeqList.txt, date recorded: Mar. 27, 2018, size: 17,843 bytes).

TECHNICAL FIELD

The present invention relates to methods for suppressing tumor by inhibiting miRNA, miRNA inhibitors for use therein, and the like.

BACKGROUND ART

Within cancers in individuals or cell lines established from them, cancer cells exist in several distinct phenotypic states, and it is believed that some of such states reflect the traits of cancer-initiating cells (Gupta et al., Cell 146:633-644, 2011; Al-Hajj et al., PNAS 100:3983-3988, 2003). A fraction of cancer cells purified for a given phenotypic state return towards equilibrium proportions after long-term culture, but few key regulatory factors modulating them have been elucidated. Furthermore, there has been no established method yet for identifying key regulatory factors that specifically influence the proportion of cancer-initiating cells, analyzing their functions, or modulating the activities of the regulatory factors.

Meanwhile, microRNAs (miRNAs) play important roles in a variety of biological systems including development by forming cell type-specific gene regulation networks, and various miRNA inhibitors have been developed (WO2010/047216). For example, it has been reported that microRNA-200 (miR-200)-containing extracellular vesicles promote metastasis of breast cancer cells to the lungs (Le M. T. et al., J Clin Invest. 2014, 124(12):5109-28). However, it is not known that tumor growth can be suppressed by suppressing miRNAs.

PRIOR-ART DOCUMENTS

Patent Documents

Patent Document 1: WO2010/047216

Non-Patent Documents

Non-Patent Document 1: Gupta et al., Cell 146: 633-644, 2011
Non-Patent Document 2: Al-Hajj et al., PNAS 100: 3983-3988, 2003

Non-Patent Document 3: Le M. T. et al., J Clin Invest. 2014, 124(12):5109-28

DISCLOSURE OF THE INVENTION

Problems to be Solved by the Invention

The present invention provides methods for suppressing tumor by miRNA inhibition, particularly, methods for effectively suppressing tumor growth in vivo. The present invention also provides miRNA inhibitors that are useful in the methods.

Means for Solving the Problems

In order to analyze in more detail the effect of miRNAs on the trait changes of tumor cells, the present inventors first developed a method of inhibiting the activity of particular miRNAs over a long period in a precisely controllable manner. For this purpose, a tetracycline-inducible expression system was combined for TuD (Tough Decoy) RNA, which is a specific, potent inhibitor for target miRNA. Using this system, the expression of miR-200c and miR-141 was simultaneously suppressed in a human colon cancer cell line by expression of a TuD. The result showed that the suppression induced significant changes in cancer cell subpopulations, including induction of epithelial-mesenchymal transition (EMT).

To further examine the effect of inhibition of the miR-200 family on tumor cells, more analyses were carried out using human triple-negative breast cancer cells. In a population of triple-negative breast cancer cells, particular subpopulations were identified based on their cell surface markers, and then the cells were observed for the mode of interconversion between subpopulations. Unexpectedly, subpopulations with epithelial traits were found to have significantly high tumorigenicity.

It was further demonstrated that the tumorigenicity in these tumor cells was significantly reduced by simultaneous inhibition of several members of the miR-200 family. It was also revealed that when simultaneously inhibiting several members of the miR-200 family in ESA(−) tumor cell subpopulations, their originally low tumorigenicity became undetectable.

The results described above suggest that the miR-200 family members are deeply involved in tumorigenicity, particularly in the growth of primary tumor at the primary site, and the tumorigenicity can be highly efficiently reduced by effectively inhibiting the miR-200 family members. Previously, it has been thought that tumor cells with mesenchymal phenotypes, which are in a more undifferentiated state, have higher tumorigenicity. The present invention has however revealed that cells with epithelial phenotypes contribute strongly to tumorigenicity, and also demonstrated that tumor growth can be suppressed by inhibiting the miR-200 family members, which promote MET (mesenchymal-epithelial transition) in tumor, and thereby shifting the equilibrium of tumor cell populations from epithelial to mesenchymal. Thus, the present invention for the first time demonstrates that inhibition of miR-200 family members effectively suppresses the growth of primary tumor and also achieves regression of tumors already formed. Particularly, the present invention enables not only tumor suppression targeting cancer stem cells but also simultaneous prevention of occurrence of cancer stem cells from non-cancer stem cells.

As described above, the present invention relates to methods for suppressing tumor by inhibiting miRNAs, miRNA inhibitors for use in suppressing tumor, and the like. More specifically, the present invention relates to the following:

[1] a method for suppressing tumor, which comprises inhibiting both at least one miRNA containing 5'-AACACUG-3' as a seed sequence and at least one miRNA containing 5'-AAUACUG-3' as a seed sequence.

[2] the method of [1], wherein the suppression of the tumor achieves both suppression of tumor formation by a group of cells with high tumorigenicity among the cell population of the tumor, and suppression of transition of a group of cells with low tumorigenicity to cells with high tumorigenicity.

[3] the method of [1] or [2], which inhibits at least miR-200c and miR-141.

[4] the method of any one of [1] to [3], wherein a nucleic acid(s) or an analog(s) thereof that binds to the seed sequences of the miRNAs is used for the inhibition.

[5] the method of any one of [1] to [4], wherein the tumor is carcinoma.

[6] the method of any one of [1] to [5], wherein the tumor is colorectal cancer, lung cancer, or breast cancer.

[7] the method of any one of [1] to [6], wherein the inhibition promotes epithelial-mesenchymal transition in the tumor.

[8] use of one or more miRNA inhibitors in manufacture of an agent for suppressing tumor by administering the miRNA inhibitors, wherein the one or more miRNA inhibitors, alone or in combination, inhibit at least one miRNA containing 5'-AACACUG-3' as a seed sequence and at least one miRNA containing 5'-AAUACUG-3' as a seed sequence.

[9] the use of [8], wherein at least miR-200c and miR-141 are inhibited in the tumor suppression.

[10] the use of [8] or [9], wherein the miRNA inhibitor(s) comprises a nucleic acid(s) or an analog(s) thereof that binds to the seed sequences of the miRNAs.

[11] a tumor-suppressing agent comprising:
a miRNA inhibitor(s) which, alone or in combination, comprises a first miRNA-binding sequence that binds to at least one miRNA containing 5'-AACACUG-3' as a seed sequence and a second miRNA-binding sequence that binds to at least one miRNA containing 5'-AAUACUG-3' as a seed sequence, and
a pharmaceutically acceptable carrier.

[12] the tumor-suppressing agent of [11], wherein the miRNA inhibitor is a TuD.

[13] a composition comprising:
one or more TuD molecules which, alone or in combination, comprise a miRNA-binding sequence comprising 5'-CAGUGUU-3' and a miRNA-binding sequence comprising 5'-CAGUAUU-3', and
a pharmaceutically acceptable carrier.

[14] the composition of [13], wherein the TuD comprises the two miRNA-binding sequences within its single molecule.

[15] the composition of [13] or [14], wherein the TuD is a synthetic TuD (S-TuD).

It is intended that for each of the items described above, inventions arbitrarily combined from two or more of the inventions described in items that recite the same antecedent item are also included in the inventions described in the antecedent item that they recite. Furthermore, it is intended that any elements of the inventions described herein and any combinations thereof are also included in the present invention. In addition, it is intended that inventions that exclude any elements described herein or any combinations thereof from the above inventions are also included in the present invention. Herein, for example, when a specific embodiment is described as a "preferable" embodiment, the specification discloses not only this embodiment, but also inventions that exclude the embodiment from antecedent inventions comprising the embodiment disclosed in the specification.

In the tumor suppression of the present invention, simultaneous inhibition of two miR-200 subfamilies—a subfamily to which miR-141 belongs and another subfamily to which miR-200c belongs—had a highly efficient effect (FIGS. 4A and 4B). Reporter assay showed that TuD-141/200c, which is a hybrid-type TuD molecule capable of simultaneous inhibition of miR-141 and miR-200c, completely inhibited the activities of the target miRNAs (FIGS. 4A and 4B). Analysis using a TuD-200c lentiviral vector in the SUM149PT cell line showed a clear reduction in EMT inducibility compared to TuD-141/200c (FIGS. 13 and 23), suggesting that controlling a broad range of target genes by simultaneous inhibition of the two miR-200 subfamilies makes an essential contribution to exertion of the tumor suppression effect of the present invention.

The miRNA inhibitor-induction system exemplified in the Examples is also applicable to some in vivo systems. For example, it is possible to test in a disease animal model whether suppression of a certain miRNA has a therapeutic potential. By screening Dox treatment periods, evaluations can be made for the proper timing to start inhibition of the miRNA or the required duration of inhibition. If such a proof of concept is obtained in the disease animal model using TuD expression vectors, therapeutic strategies in terms of the administration period and dose of miRNA inhibitors such as S-TuD can be readily designed.

The present invention also demonstrated induction of EMT in breast cancer cells by inhibiting miRNAs in the same manner as described above, and examined the effect of miRNA inhibition on tumorigenicity and in vivo tumor growth. Tumor cells such as breast cancer include a number of subpopulations characterized by different phenotypes. In the Examples, the present inventors demonstrated that the increased expression levels of miR-200 family members in the Epithelial Specific Antigen (ESA)(+) fraction of the tumor cells are the major determining factor for the epithelial cell traits. When the miR-200 family was suppressed in the ESA(+) or ESA(−) fraction, the ESA(+) fraction showed a dramatic reduction in its strong tumorigenicity, and the ESA(−) fraction also showed complete suppression of its weak tumorigenicity, which presumably originated from ESA(+) cells stochastically converted from ESA(−) cells in vivo. Furthermore, when a tumor was formed by xenotransplantation of the ESA(+) fraction, the xenograft was significantly shrunk by inhibitors of miR-200 family members. These results suggest that epithelial traits in tumor cells are essential characteristics of cancer-initiating cells, and thus it is of therapeutic value to suppress the activity of the miR-200 family for those cells to become stuck at a mesenchyme-like phenotype and lose their cellular plasticity.

As shown in Example 2, the ESA(+) subpopulations with epithelial cell traits had high tumorigenicity (FIG. 11-2B), and steady suppression of the activity of the miR-200 family induced EMT in these ESA(+) subpopulations when judged with several parameters (FIG. 13), and strongly suppressed tumor progression and even diminished already formed tumor in the mouse xenograft model (FIG. 18). Meanwhile, the ESA(−) subpopulations with mesenchymal cell-like traits had only weak tumorigenicity in the same mouse xenograft model (FIG. 11-2B), and exogenous expression of miR-200c and -141 in these subpopulations induced MET-like processes which involved even cells with intermediate characteristics between epithelial and stromal (FIGS. 15 and 16), leading to significant potentiation of the tumorigenicity (FIG. 17).

As described above, the present invention for the first time demonstrated that inhibition of the activity of the miR-200 family induced tumor suppression. As shown in FIG. 23, the suppression of either miR-200c or miR-141 alone was not enough to fully induce the conversion from ESA(+) to ESA(−) cells, and the suppression of both was essential to achieve sufficient conversion. Thus, the present invention for the first time demonstrates that effective tumor suppression can be achieved by inhibiting two miRNA species.

Effects of the Invention

The present invention provides novel methods for suppressing tumor by inhibiting miRNAs. The methods of the present invention induce significant reduction of tumorigenicity and thereby achieve suppression of in vivo tumor growth. The present invention is expected to be a promising therapeutic means against tumors that are difficult to treat with conventional methods.

BRIEF DESCRIPTION OF THE DRAWINGS

FIG. 3-1. EMT induced by pLSB-Tete7SK-TuD-141/200c. (A) The sequence and structure of hybrid TuD RNA TuD-141/200c which inhibits miR-200 family members simultaneously. The sequences of miR-200 family members and their seed sequences (boxed) are shown at the bottom. (B) pLSB-Tete7SK-TuD-141/200c or pLSB-Tete7SK-TuD-NC was introduced into HCT116-TetOn III cells, and the cells were allowed to proliferate in the absence (Dox−) or presence of Dox (Dox+). On day 18, a portion of the cells cultured under Dox+ was changed to Dox− conditions and further cultured (Dox+/−). FACS analysis was performed for ESA expression profiles at the indicated time points (B).

FIG. 3-2. A continuation of FIG. 3-1. (C) pLSB-Tete7SK-TuD-141/200c or pLSB-Tete7SK-TuD-NC was introduced into HCT116-TetOn III cells, and the cells were allowed to proliferate in the absence (Dox−) or presence of Dox (Dox+). On day 18, Dox was removed from a half of the Dox+ culture, and the cells were allowed to proliferate (Dox+/−). Cellular morphology was observed under a phase-contrast microscope at the indicated time points shown. The bar indicates 100 μm.

FIG. 10-1. Separation of four subpopulations ESA(+)/CD24(+), ESA(+)/CD24(−), ESA(−)/CD24(+), and ESA(−)/CD24(−) of SUM149PT cells. (A) ESA(−) cells detected in parent SUM149PT were sorted by FACS and allowed to proliferate. ESA/CD24 and ESA/CD49f expression profiles were analyzed by FACS after 28 or 15 days of sorting. (B)

Morphologies of ESA(+)/CD24(+), ESA(+)/CD24(−), ESA(−)/CD24(+), and ESA(−)/CD24(−) cells. The bar indicates 100 μm.

Figure 1:
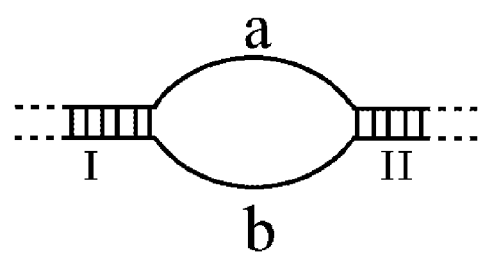
FIG. 1 is a schematic diagram showing an example of the basic structure of TuD. The numbers of base pairs of I and II are not limited to the numbers of vertical lines shown within the diagram. I and II may or may not be completely double-stranded, and may contain unpaired nucleotides such as gaps. Meanwhile, a and b are not limited to completely single-stranded chains, and may partially form double-stranded chains.
Figure 2:
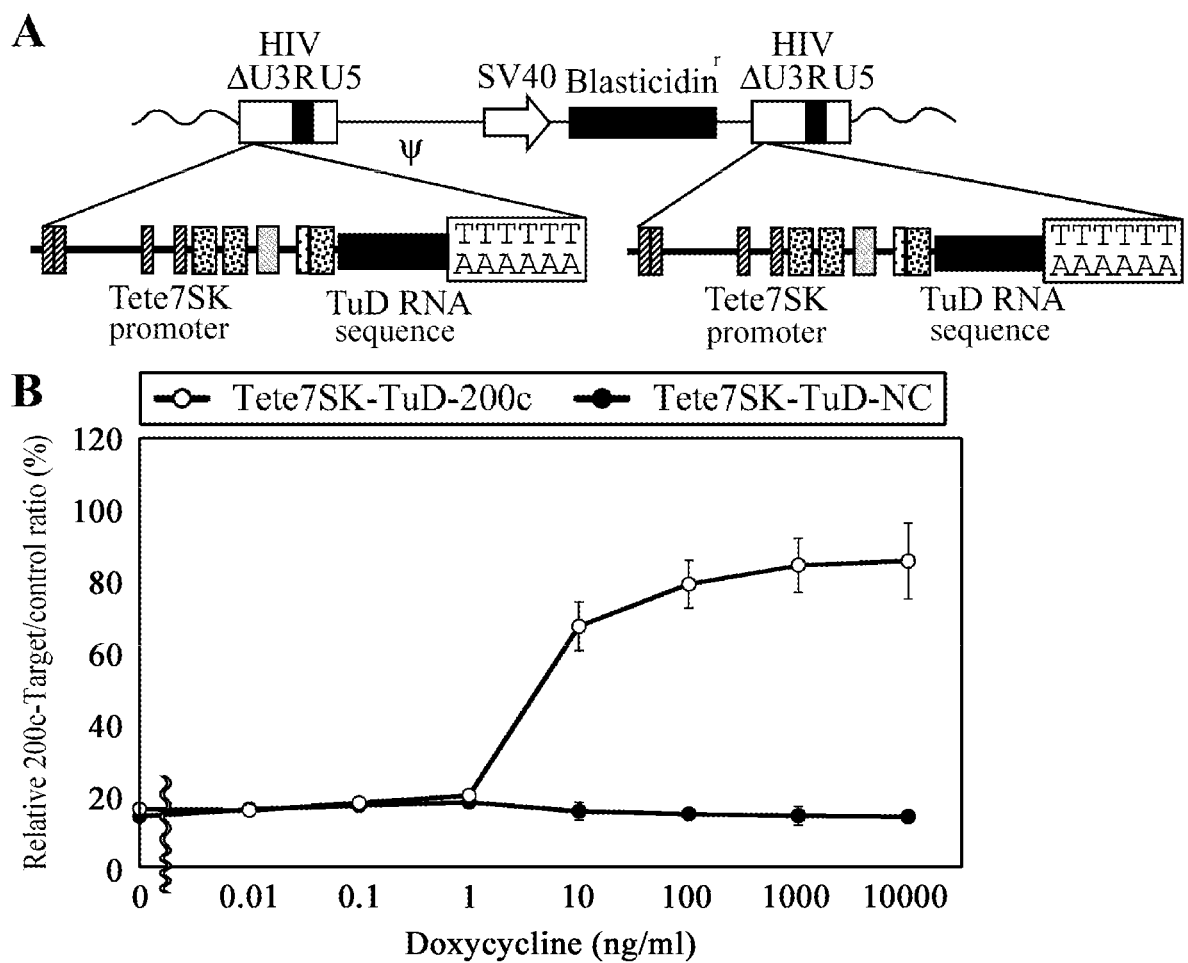
FIG. 2. Tet-inducible TuD RNA expression system. (A) The structure of a provirus of Tet-inducible TuD RNA expression lentiviral vector, pLSB-Tete7SK-TuD. (B) Doxycycline-dose dependency of the miR-200c-inhibiting activity of pLSB-Tete7SK-TuD-200c. pLSB-Tete7SK-TuD-200c or pLSB-Tete7SK-TuD-NC (negative control) was introduced into HCT116-TetON III cells, and selection was carried out using blasticidin. The cells were transfected with dual luciferase reporter vectors T200c and UT (FIG. 5), and allowed to proliferate in the presence of Dox at several doses. Dual luciferase reporter assay was performed 48 hours after transfection. The expression ratio of miR-200c-RL/FL to UT-RL/FL was represented as mean±SD (n=3).
Figures 1, 10:
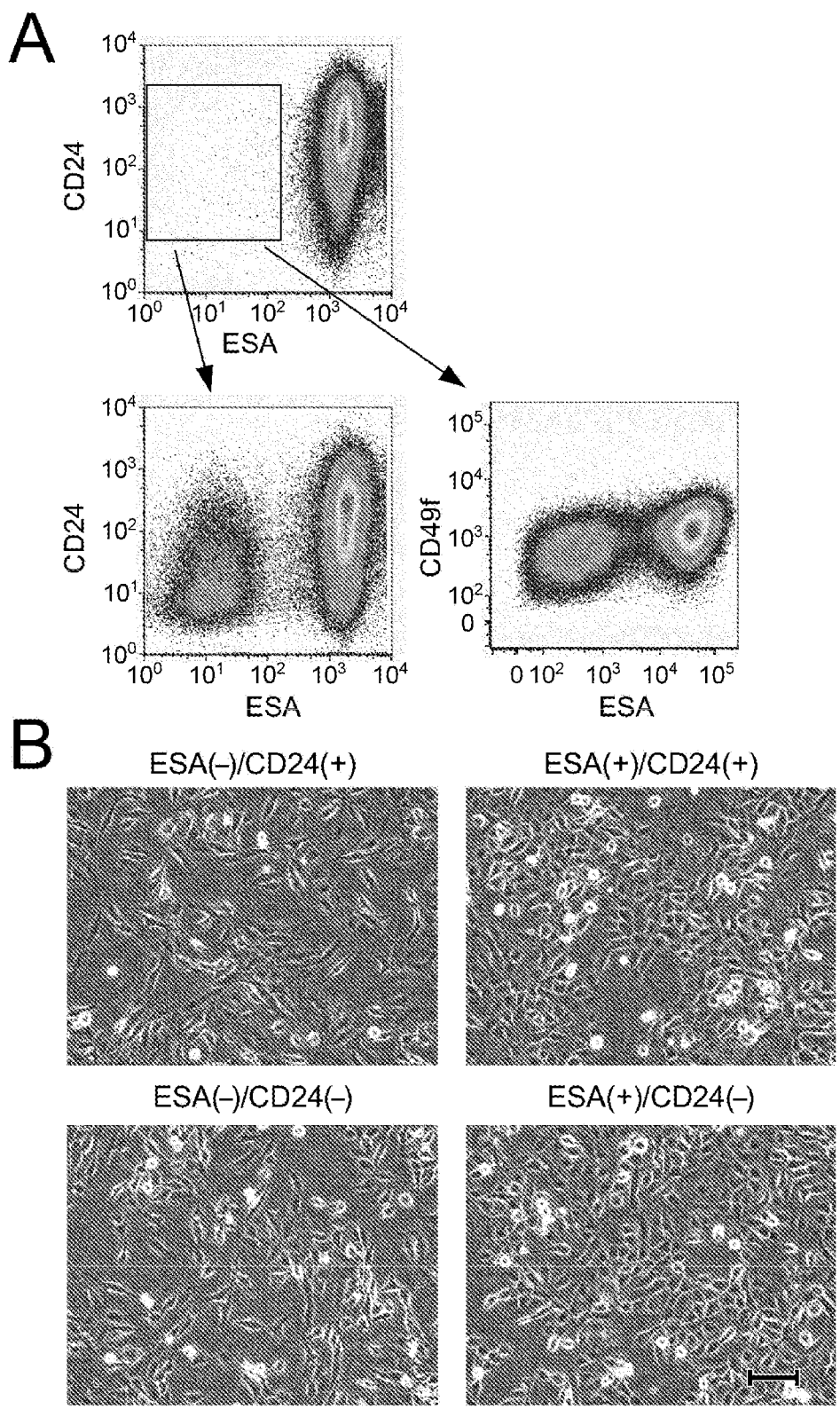
Figures 2, 10:
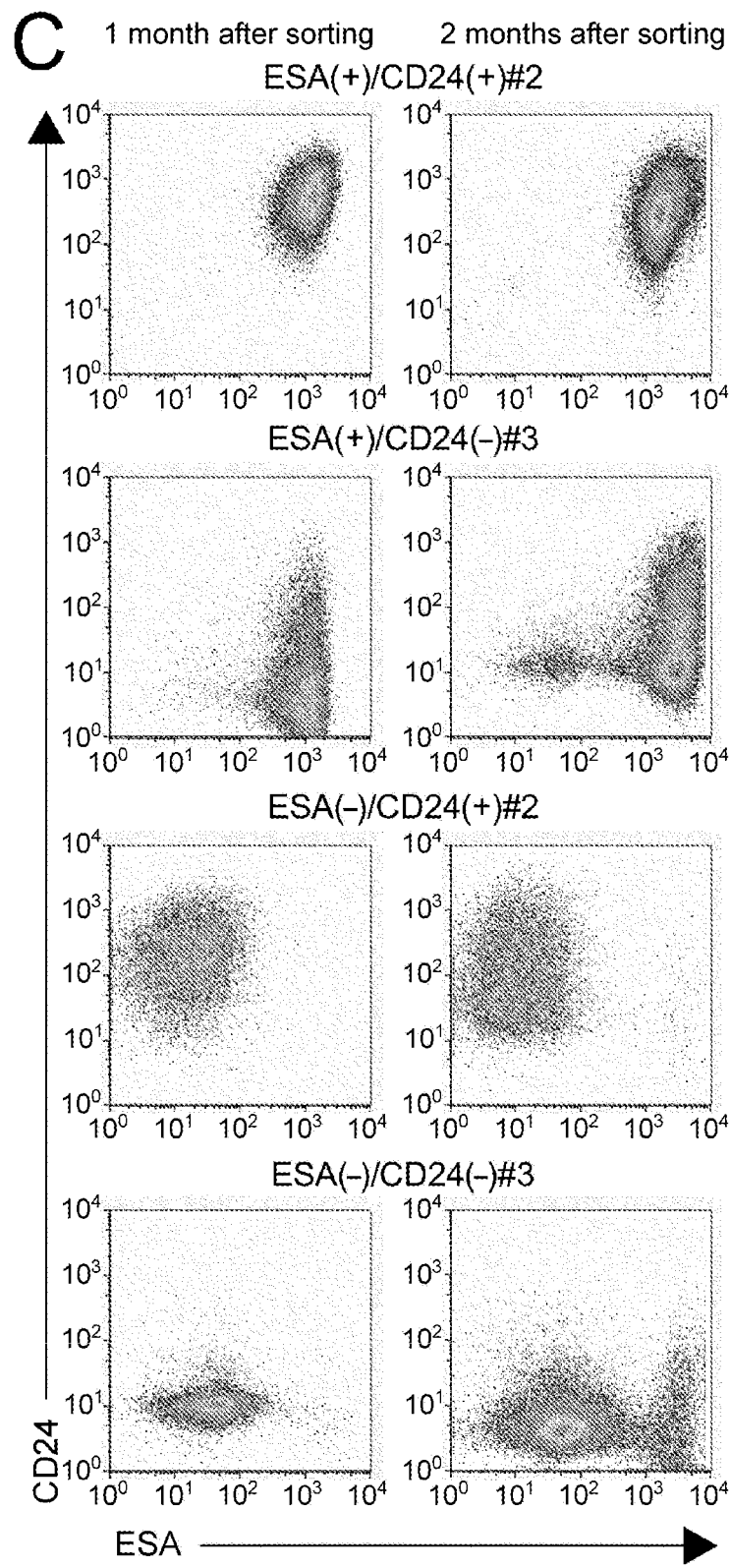

FIG. 10-2. A continuation of FIG. 10-1. (C) One or two months after single cell sorting, the ESA/CD24 expression profile of cell clones derived from each subpopulation was analyzed by FACS.

Figures 1, 11:
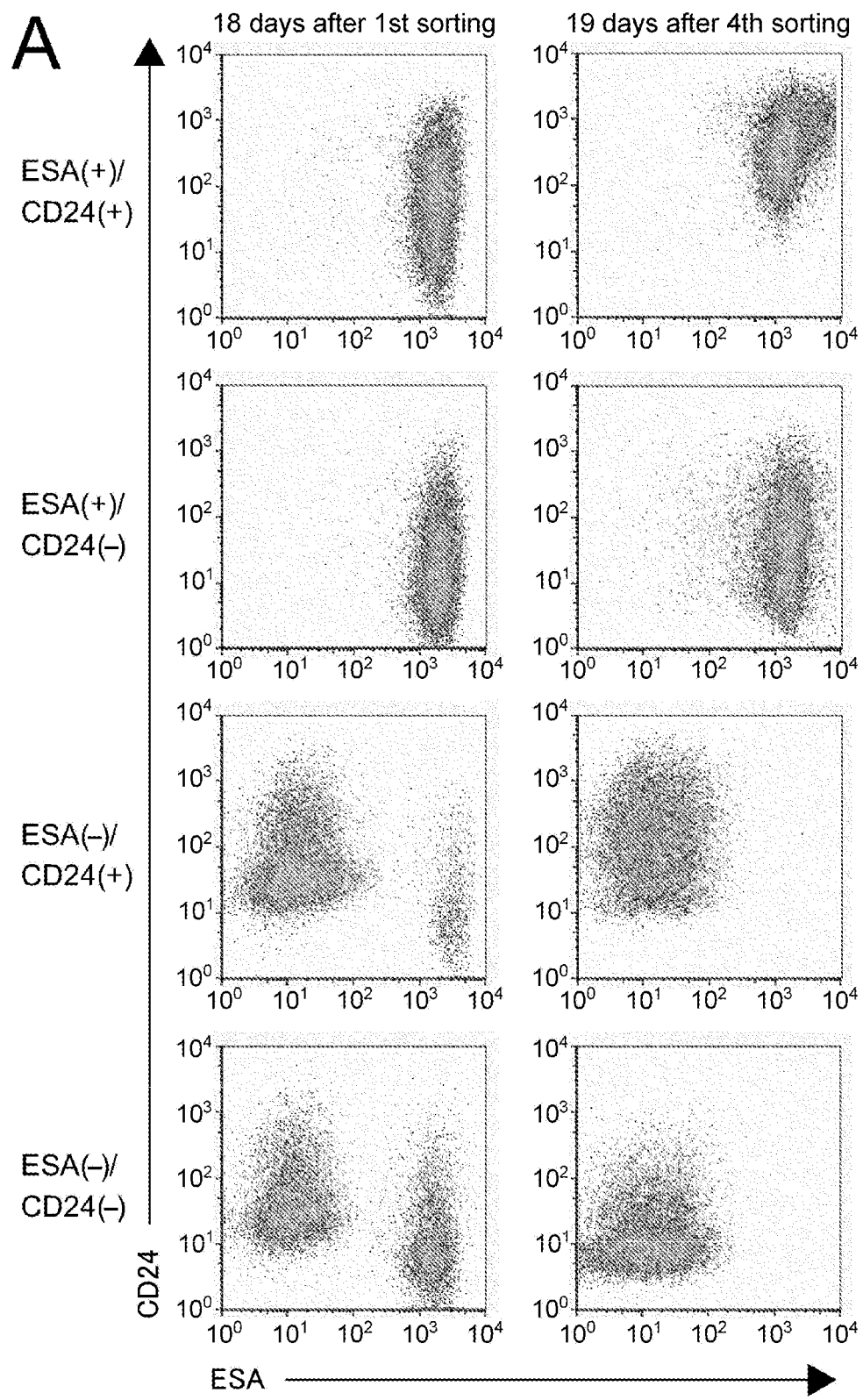
Figure 11:
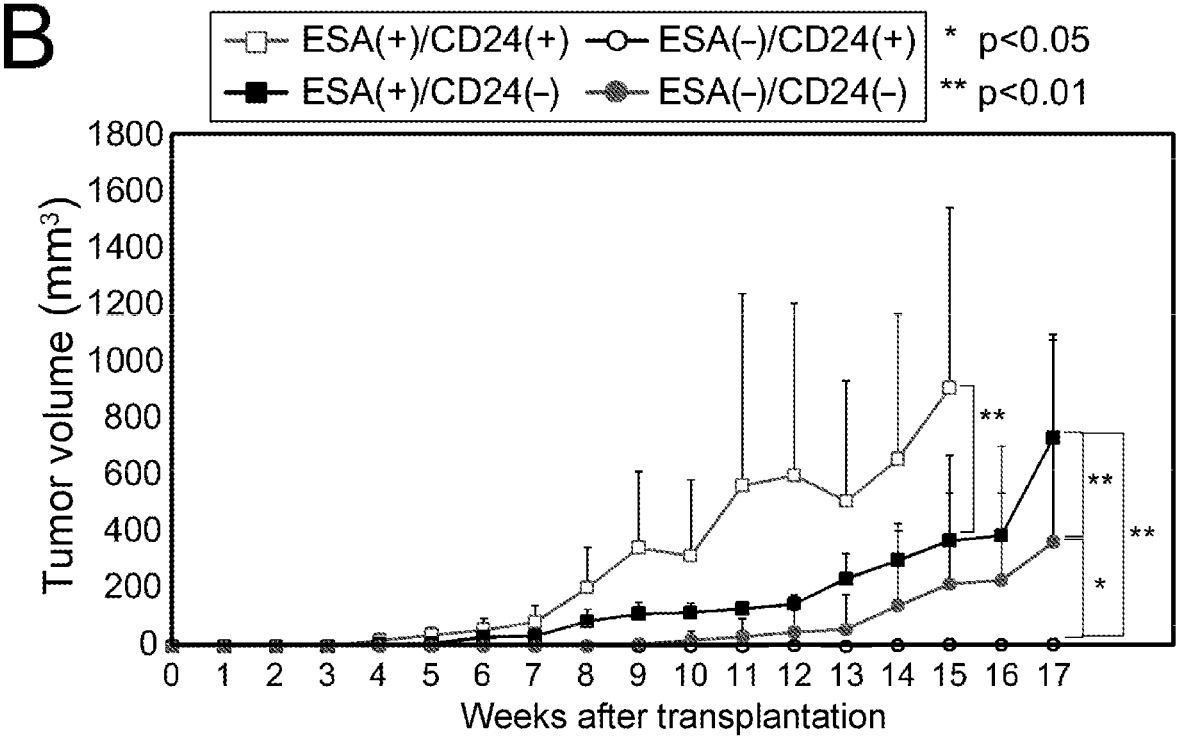
Figure 2:
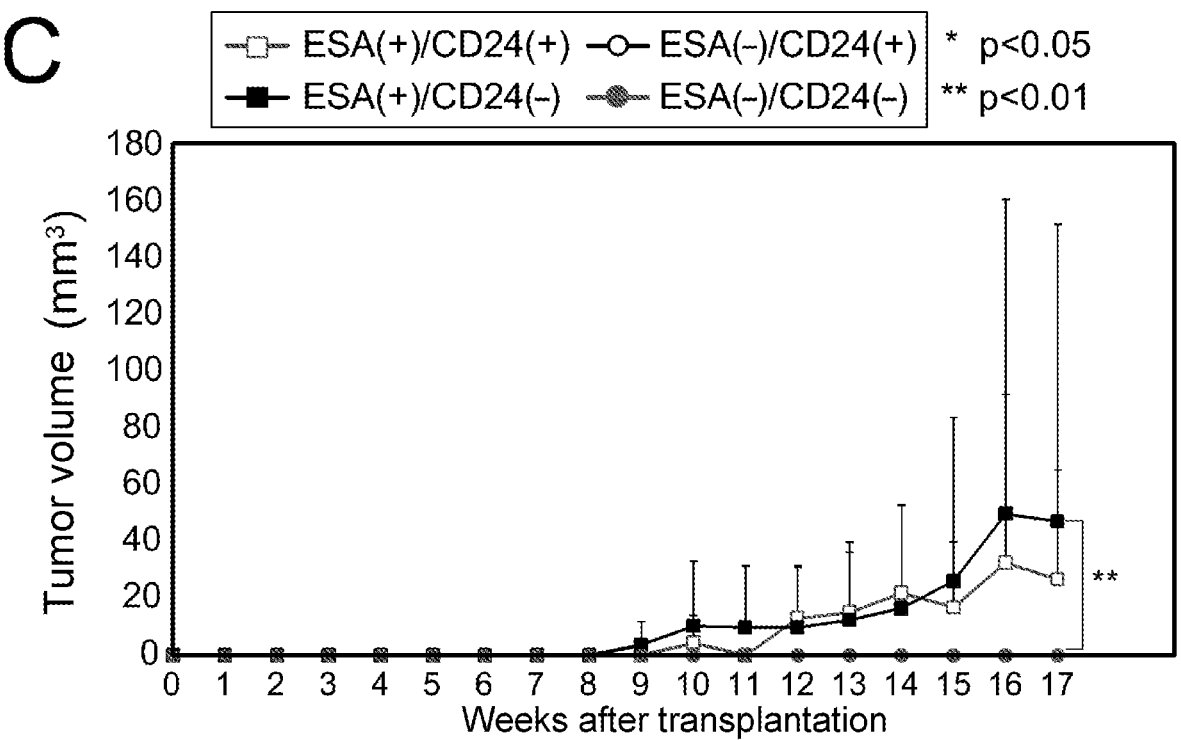

FIG. 11-1. Tumorigenicity of the four subpopulations of SUM149PT cells. (A) The ESA/CD24 expression profile of each subpopulation, which was allowed to proliferate for 18 to 19 days after a single round or four consecutive rounds of FACS sorting.

FIG. 11-2. A continuation of FIG. 11-1. Immediately after sorting of each subpopulation from a mixed culture similar to that shown in FIG. 10-1A (lower panel), 30000 cells (B) and 300 cells (C) were injected into mouse mammary fat pads. Tumor volume was measured and represented as mean+SD (n=5), and analyzed by two-way ANOVA using Tukey post-hoc test (*$P<0.05$; **$P<0.01$).

Figure 12:
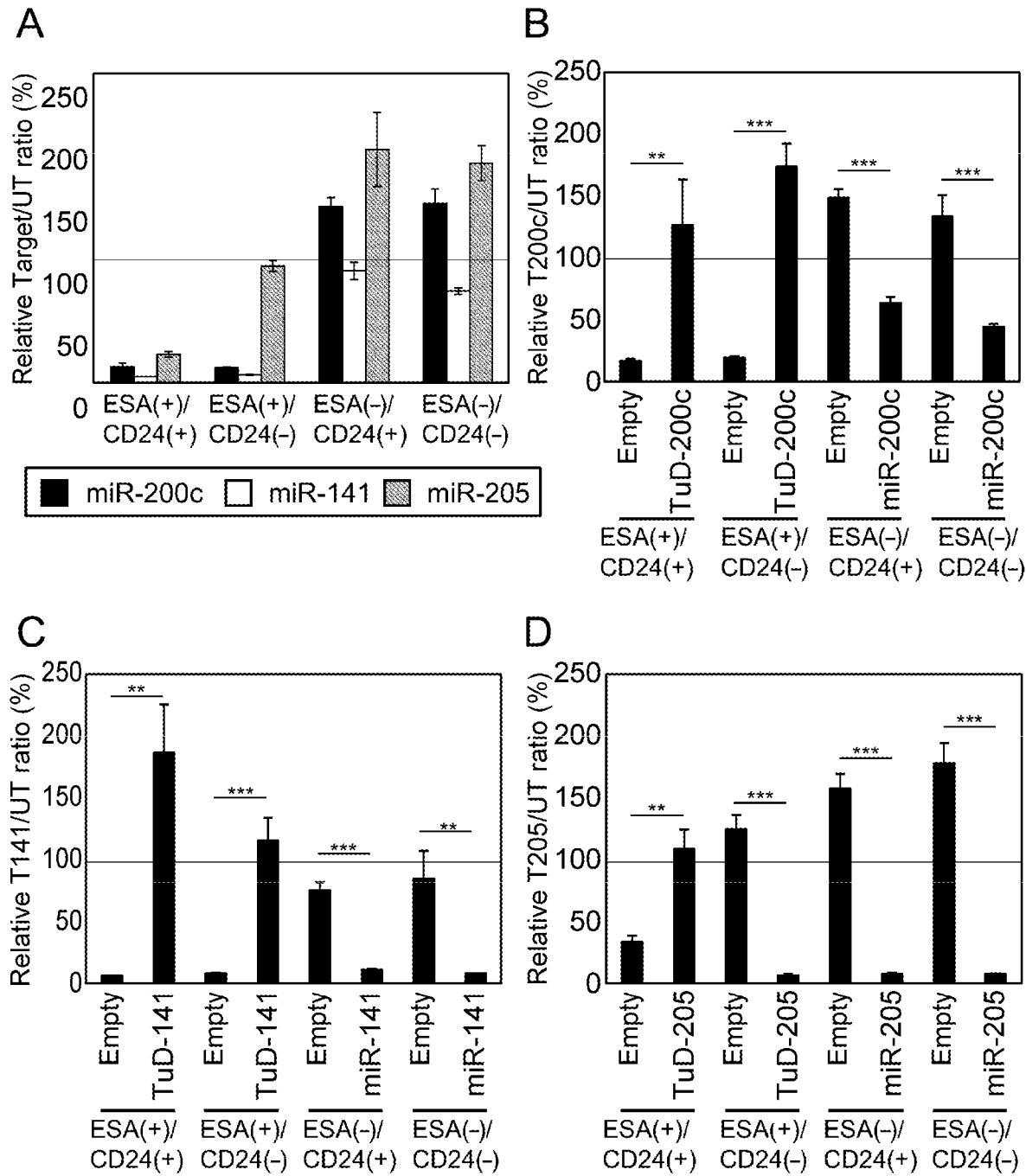

FIG. 12. Expression pattern distribution for miR-200c, -141, and -205 observed in the four subpopulations. (A) ESA(+)/CD24(+), ESA(+)/CD24(−), ESA(−)/CD24(+), and ESA(−)/CD24(−) cells were transfected with dual luciferase reporters, and luciferase activity was measured 48 hours later. (B, C, and D) A lentiviral vector carrying an expression unit for TuD RNA or miRNA was introduced into ESA(+)/CD24(+), ESA(+)/CD24(−), ESA(−)/CD24(+), and ESA(−)/CD24(−) cells, followed by drug selection. The stable vector-introduced cells were transfected with dual luciferase reporters, and luciferase assay was performed after 48 hours of incubation. The expression ratios of miR-200c-RL/FL to UT-RL/FL (A and B), miR-141-RL/FL to UT-RL/FL (A and C), and miR-205-RL/FL to UT-RL/FL (A and D) were represented as mean±SD (n=3). The data were analyzed by Student's t test ($P<0.01$; *$P<0.001$).

Figure 13:
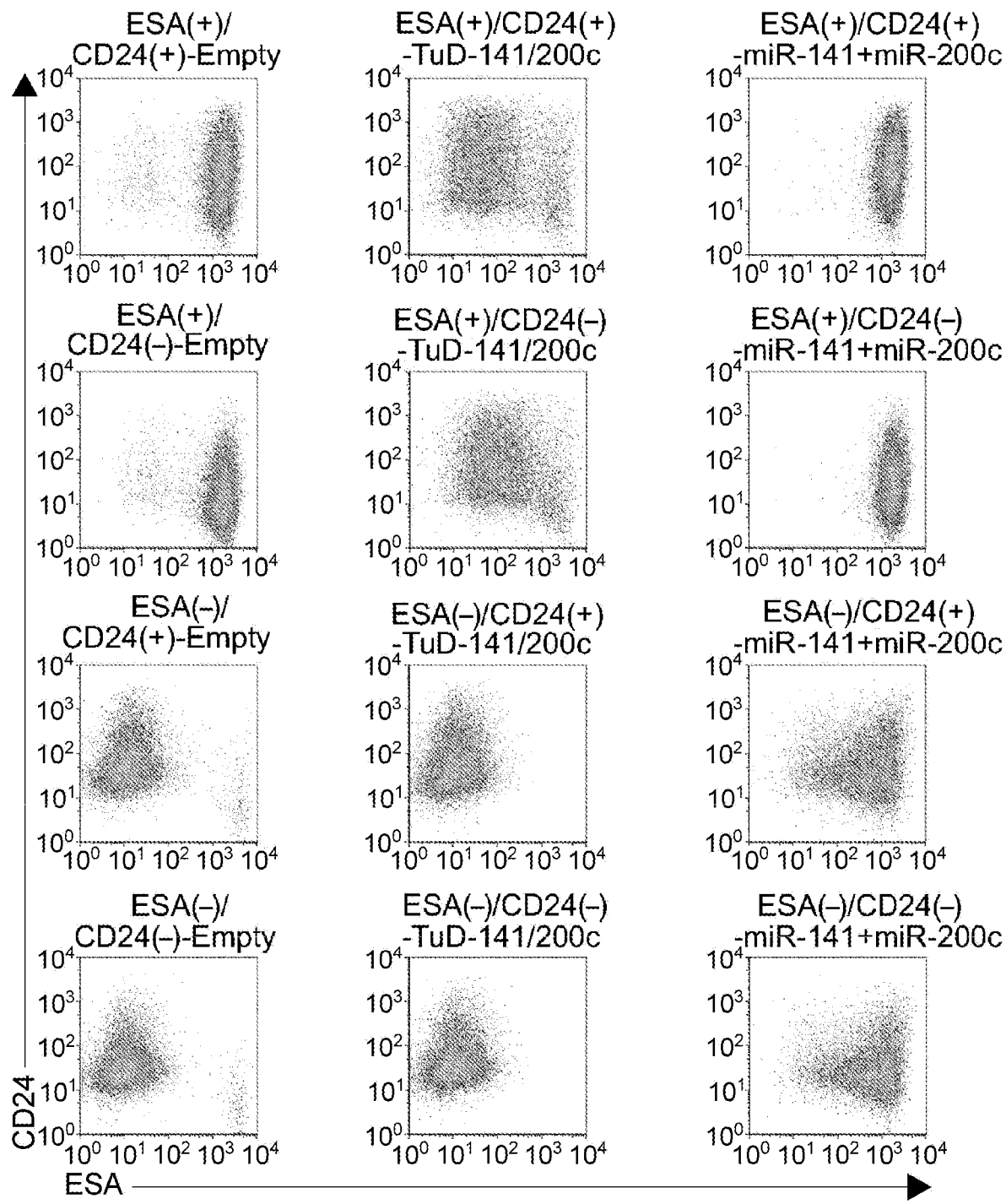

FIG. 13. Effect of introduction of TuD-141/200c or miR-141+miR-200c vector on the ESA/CD24 expression profile. The TuD-141/200c or miR-141+miR-200c vector was introduced into cells of the parallel cultures used in FIG. 10-1A (lower panel). Two days after introduction, these vector-introduced cells were sorted by FACS for ESA(+)/CD24(+), ESA(+)/CD24(−), ESA(−)/CD24(+), and ESA(−)/CD24(−) fractions, and cultured for 18 days. The ESA/CD24 expression profile in these cells was analyzed by FACS.

Figure 14:
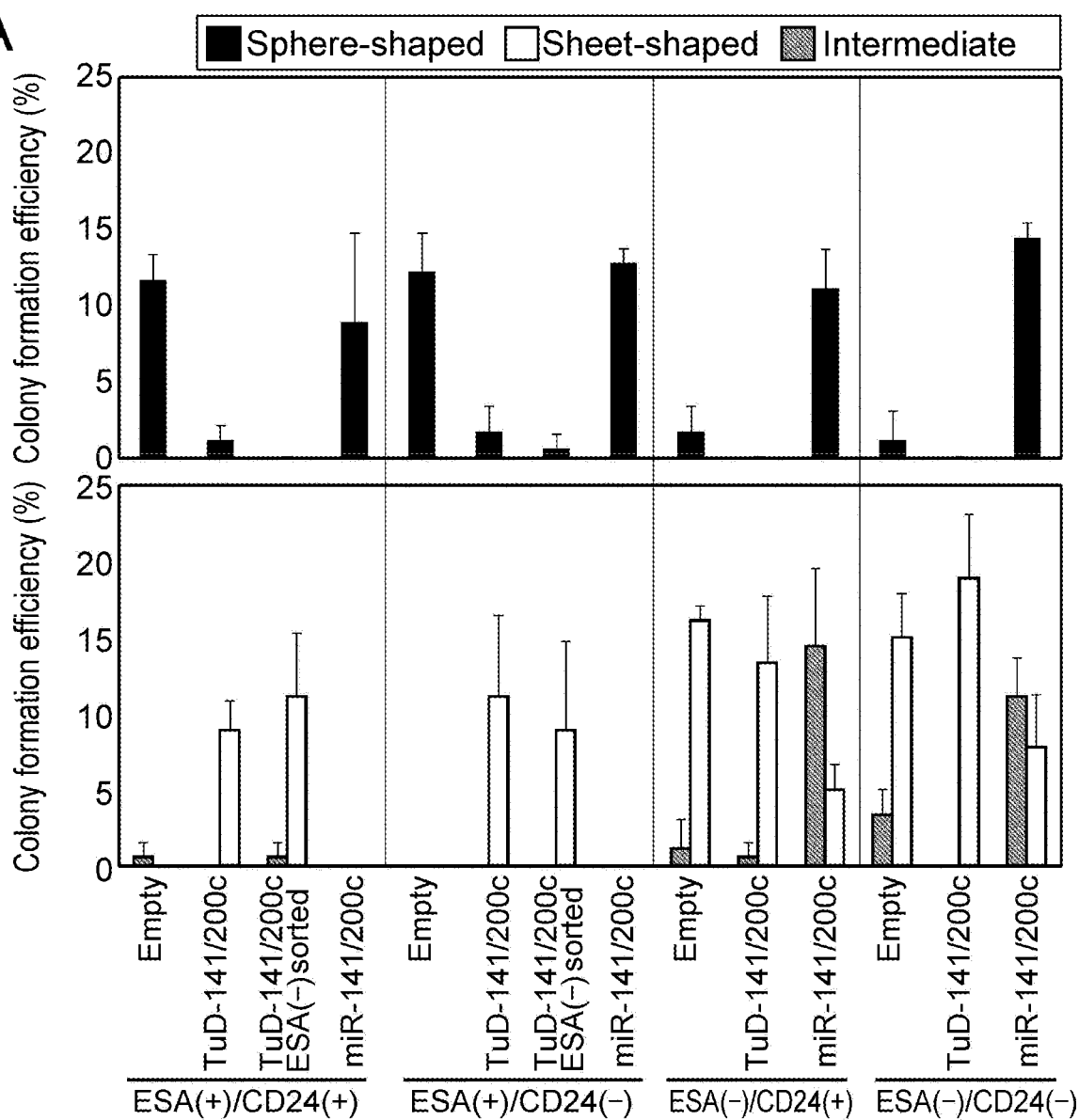
Figure 14:
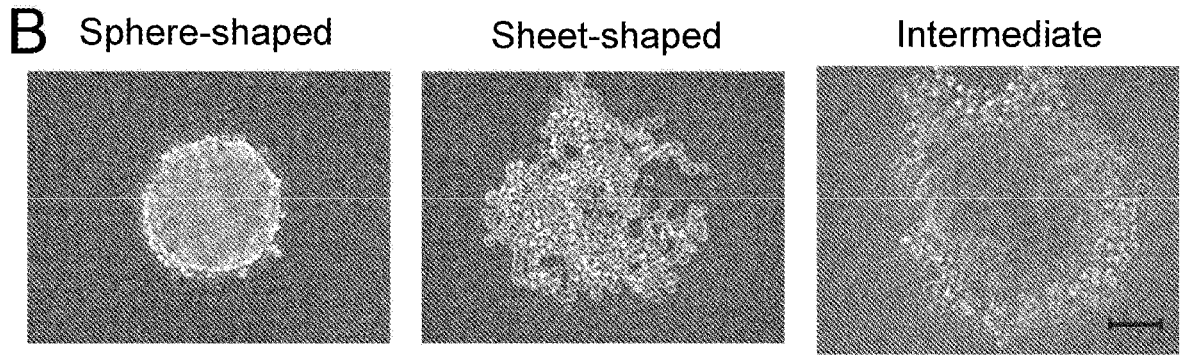

FIG. 14. Tumorsphere formation activity of the subpopulations introduced with an empty vector, TuD-141/200c vector, and miR-141/200c vector. (A) Efficiency of tumorsphere formation by a single cell sorted from the vector-introduced cells. Sphere-shaped (mammosphere), sheet-shaped, and intermediate-type colonies were counted separately, and the colony formation efficiency (%) was represented as mean±SD (n=3). (B) Morphologies of sphere-shaped, sheet-shaped, and intermediate-type colonies. The bar indicates 100 μm.

Figures 1, 15:
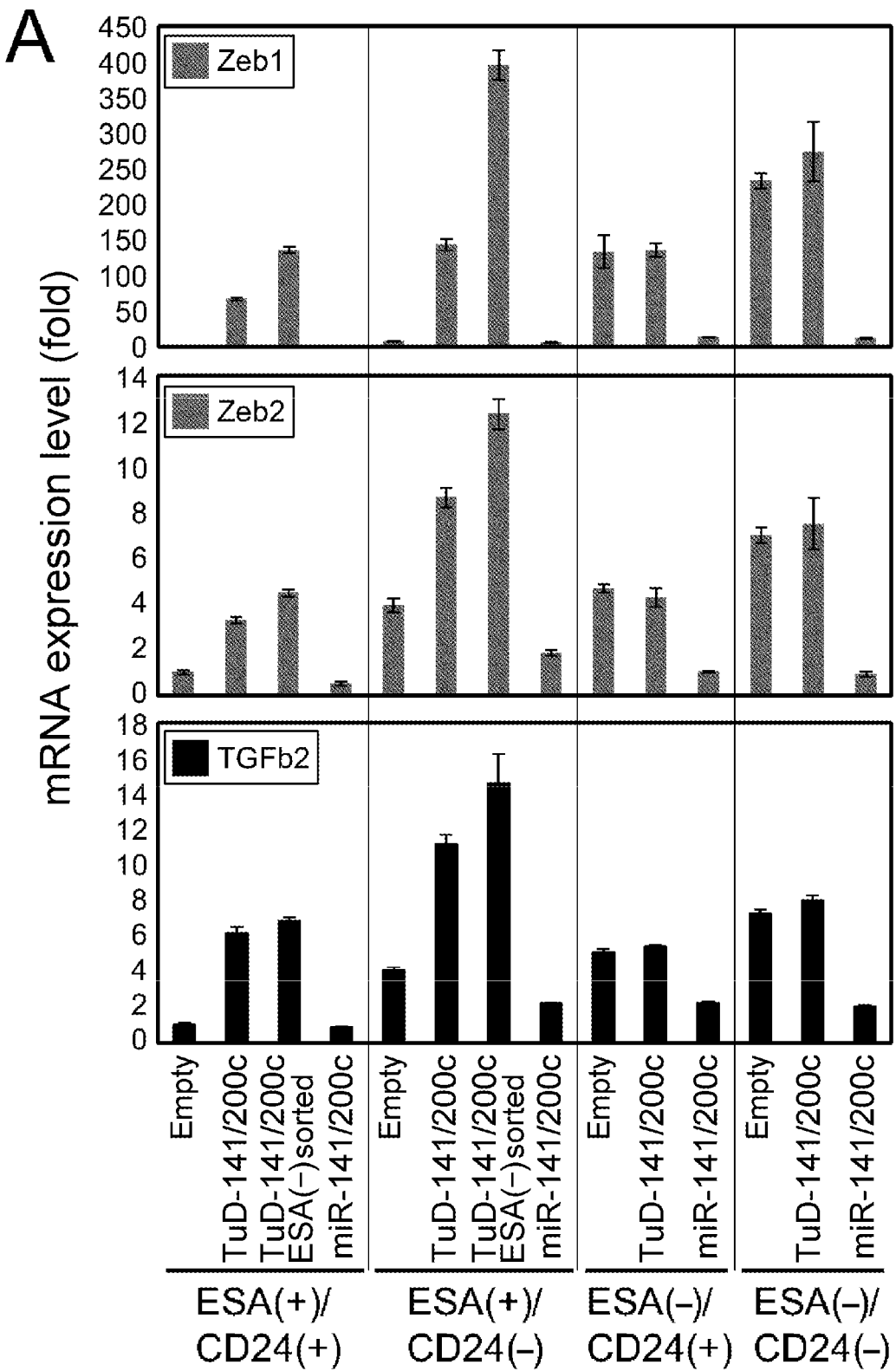
Figures 2, 15:
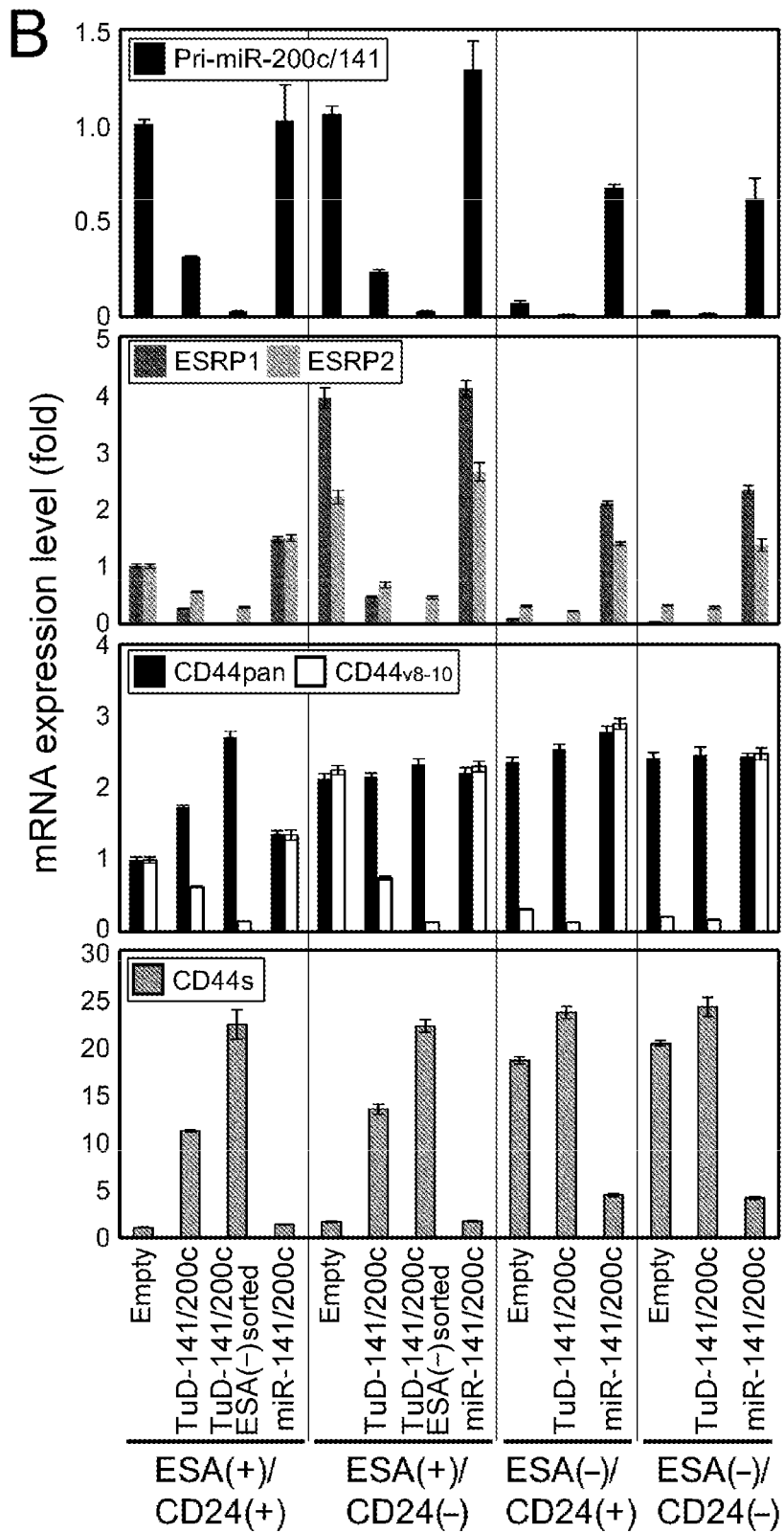

FIG. 15-1. Effect of exogenous modulation of miR-200c/141 activity on the expression levels of Zeb1 and Zeb2, which are targets of miR-200 family members as well as targets of transcription repressors. (A) The expression levels of Zeb1, Zeb2, and TGFb2 mRNA, which are direct targets of miR-200 family members, were determined by real-time RT-PCR. Normalized expression levels were represented as mean±SD (n=3) as the levels in the empty vector-introduced ESA(+)/CD24(+) cells were taken as 1.00.

FIG. 15-2. A continuation of FIG. 15-1. (B) Expression levels of pri-miR-200c/141, ESRP1, ESRP2, total CD44 (pan-CD44), CD44v8-10, and standard CD44 (CD44s) mRNA. GAPDH mRNA was used as an internal standard. The pri-miR-200c/141 PCR primers do not detect mature miR-200c and miR-141. Normalized expression levels were represented as mean±SD (n=3) as the levels in the empty vector-introduced ESA(+)/CD24(+) cells were taken as 1.0.

Figure 16:
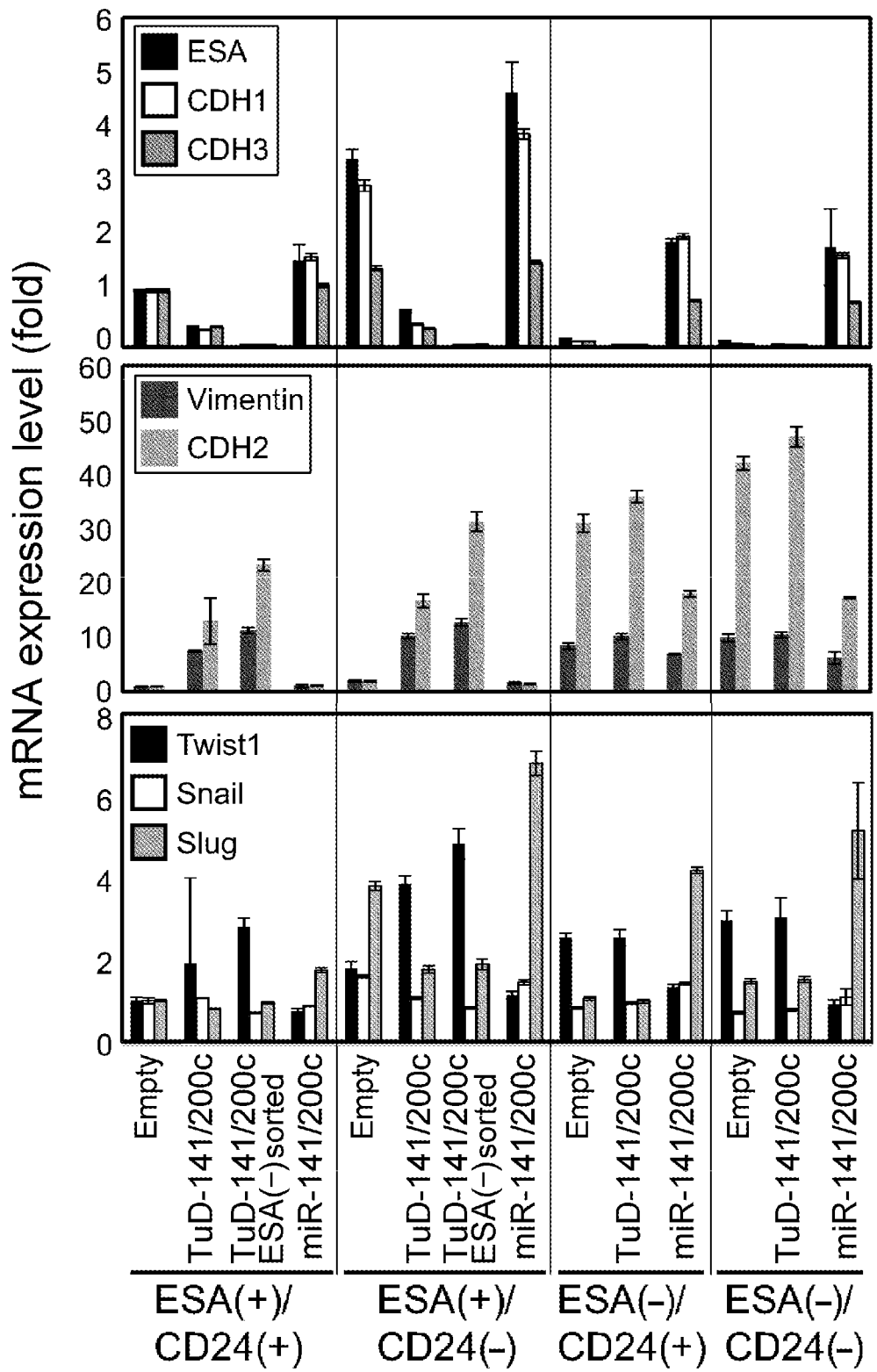

FIG. 16. Effect of exogenous modulation of miR-200c/141 activity on the mRNA levels of some EMT markers. Real-time PCR was performed to determine the expression levels of ESA, CDH1, and CDH3 (epithelial markers); Vimentin and CDH2 (mesenchymal markers); and Twist, Snail, and Slug (mesenchyme-specific transcription factors). GAPDH was used as an internal standard. Relative expression levels were represented as mean±SD (n=3) as the levels in the empty vector-introduced ESA(+)/CD24(+) cells were taken as 1.0.

Figure 17:
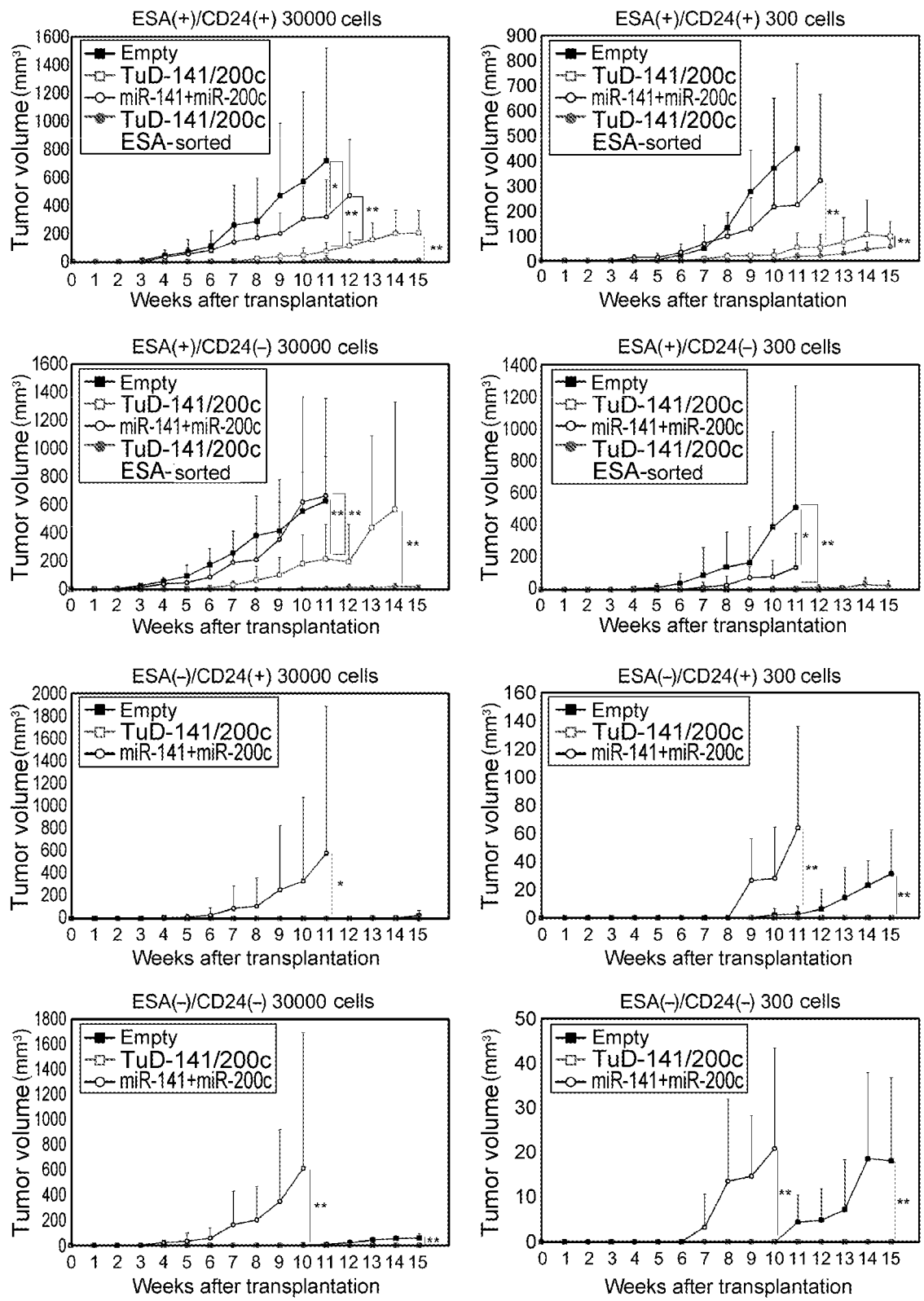

FIG. 17. Effect of TuD-141/200c and miR-141+miR-200c vectors on the tumorigenicity of the four subpopulations. 30000 or 300 vector-introduced cells were injected into mammary fat pads. Tumor volume was measured and represented as mean+SD (n=5), and analyzed by two-way ANOVA using Tukey post-hoc test (*$P<0.05$; **$P<0.01$).

Figure 18:
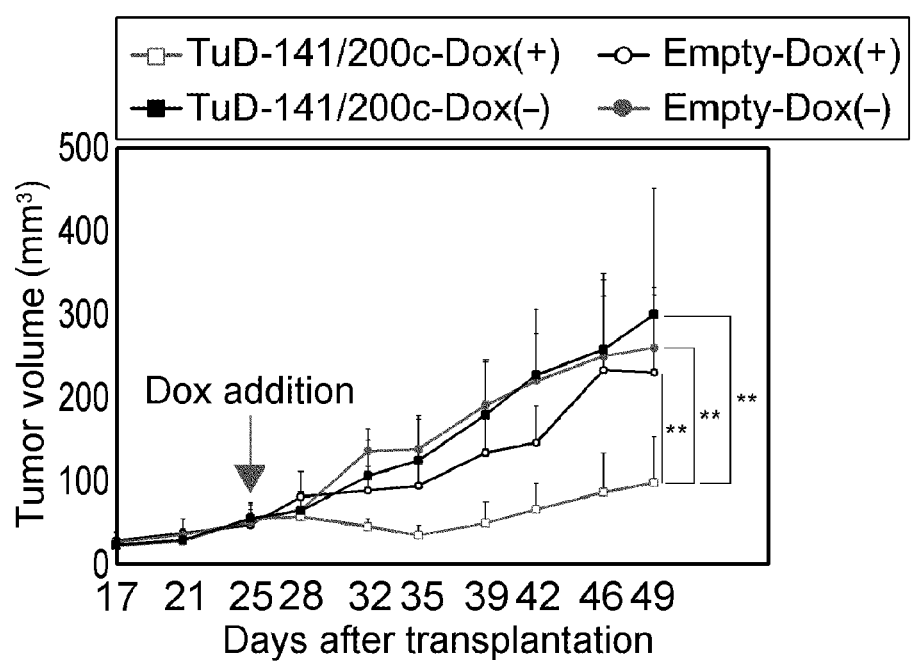

FIG. 18. Tumor shrinkage by inducing TuD-141/200c expression in SUM149PT xenografts. SUM149PT-TetOn-TuD-141/200c or SUM149PT-TetOn-Empty (500,000 cells) was prepared in the manner described in FIG. 25, and injected into mammary fat pads. Dox(+) mice were supplied with water containing 2 mg/ml doxycycline and 5% sucrose from 25 days after transplantation. Tumor volume was measured and represented as mean+SD (n=5), and analyzed by two-way ANOVA using Tukey post-hoc test (**$P<0.01$).

Figure 19:
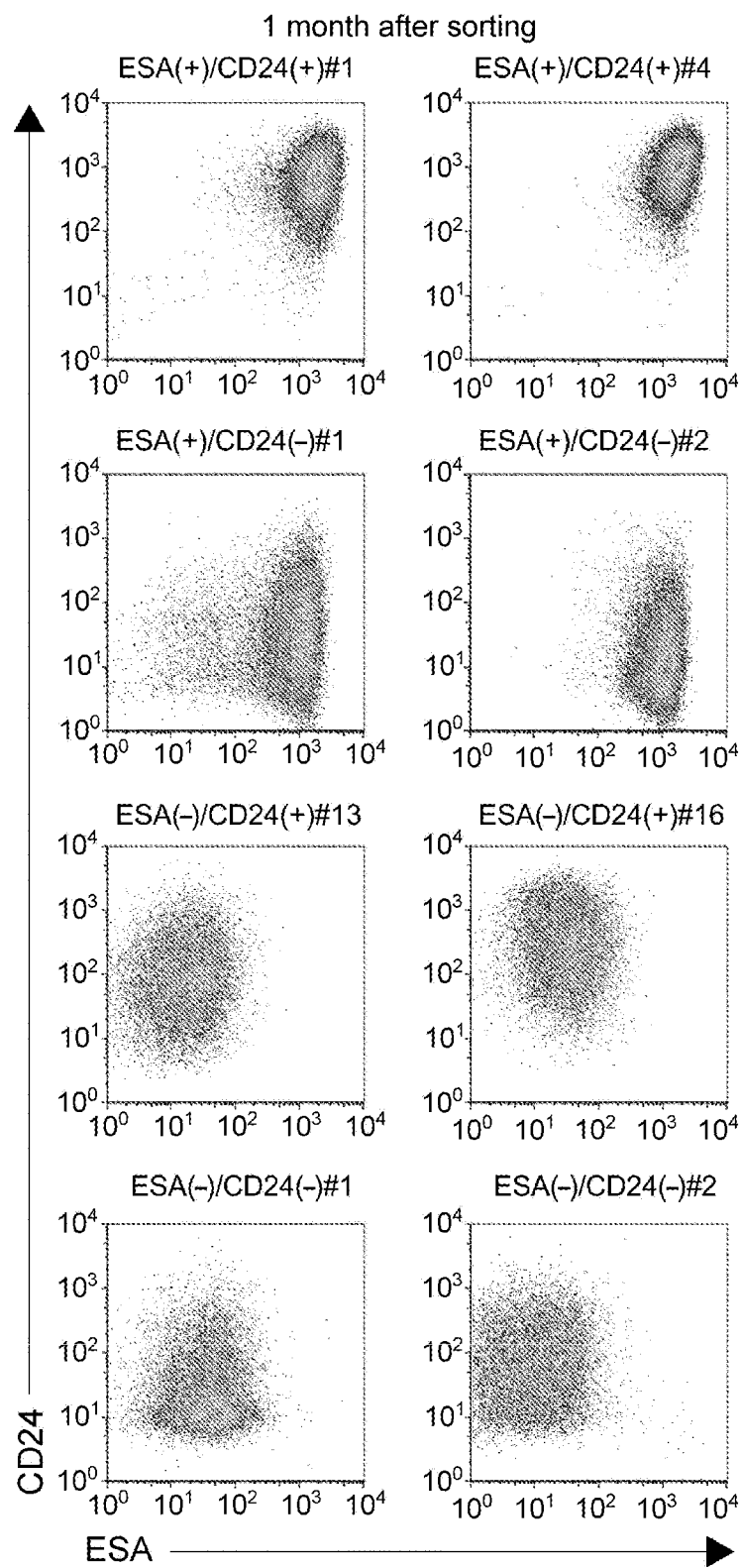

FIG. 19. ESA/CD24 expression profiles of two single colonies isolated from each of the four subpopulations. Each cell colony shown in FIG. 10-2(C) was prepared by FACS, and the expression profile was analyzed one month after single-cell sorting.

Figure 20:
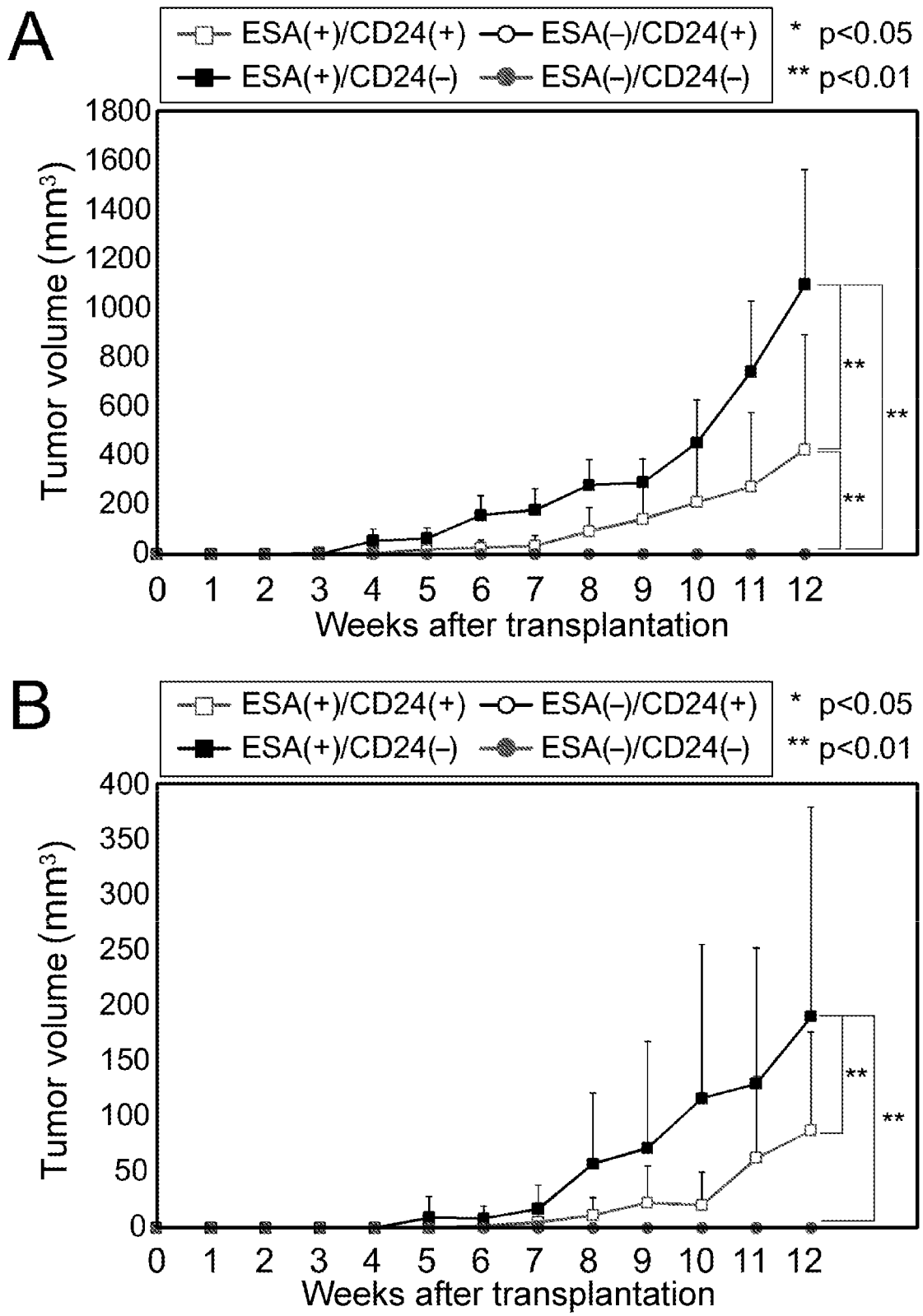

FIG. 20. Tumor formation of ESA(+)/CD24(+), ESA(+)/CD24(−), ESA(−)/CD24(+), and ESA(−)/CD24(−) cells purified through four consecutive rounds of sorting. 30000 cells (A) or 300 cells (B) from each subpopulation were injected into mammary fat pads. Tumor volume was measured and represented as mean+SD (n=4), and analyzed by two-way ANOVA using Tukey post-hoc test (*$P<0.05$; **$P<0.01$).

Figure 21:
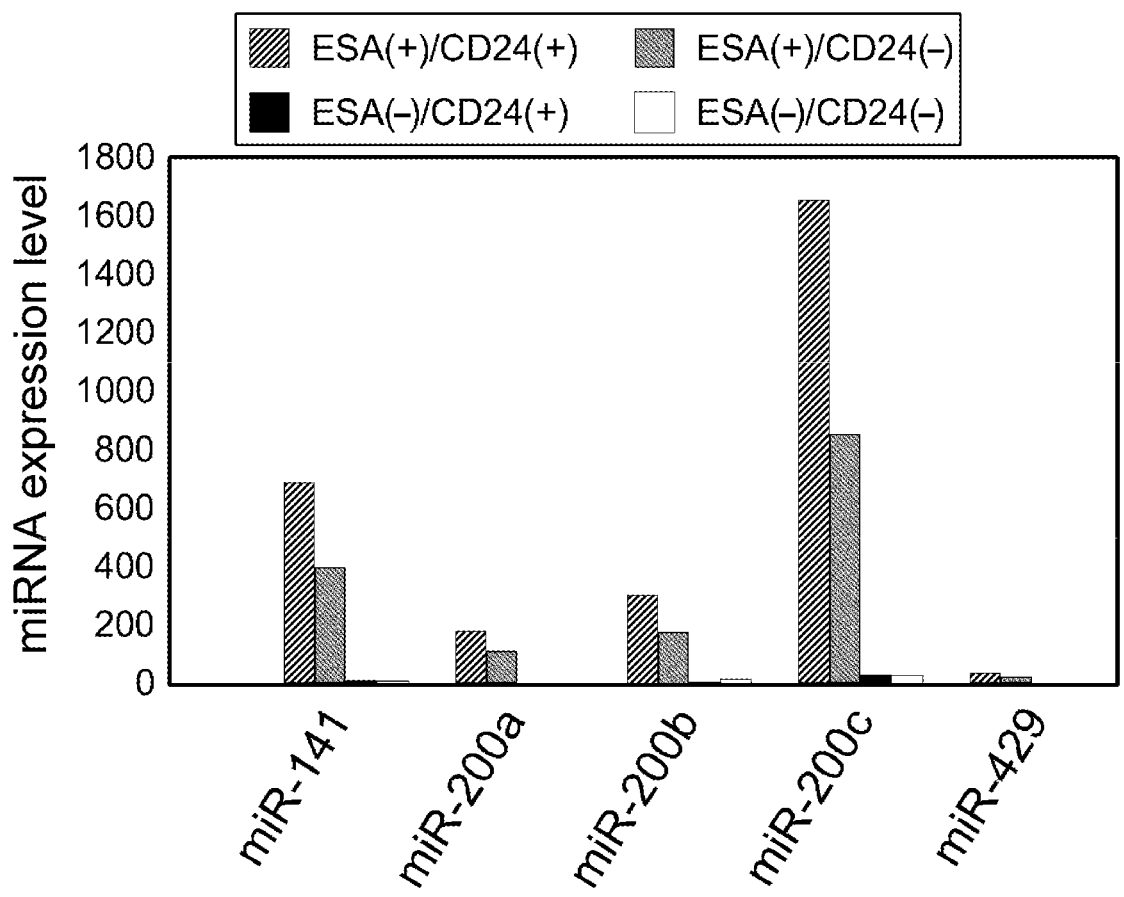

FIG. 21. Expression levels of miR-200 family members in the four subpopulations, which were determined by miRNA microarray analysis. The expression levels were represented in a relative unit.

Figure 22:
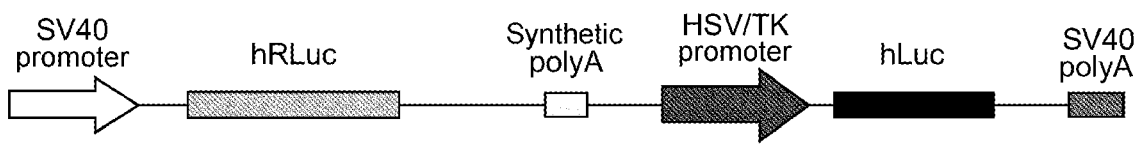
Figure 22:
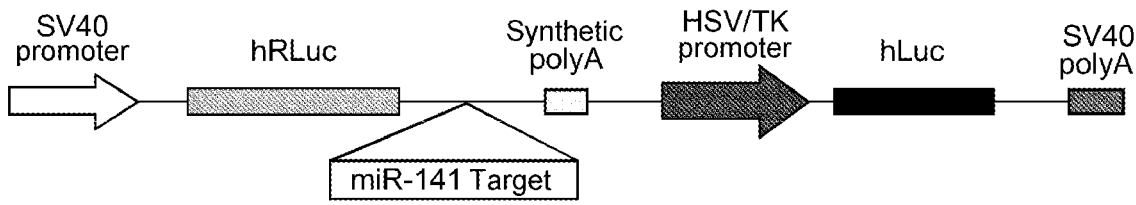
Figure 22:
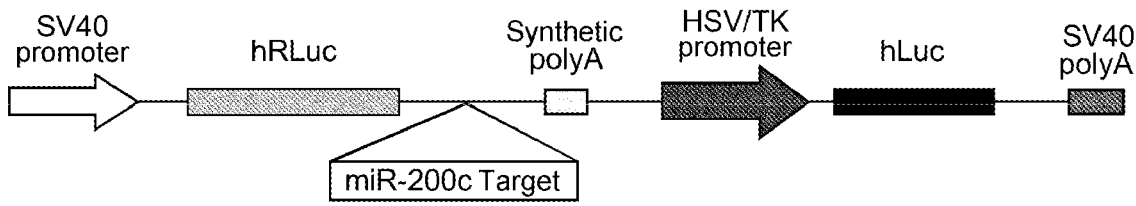

FIG. 22. Structures of the luciferase reporters used in the present experiments. Structure of dual luciferase reporter plasmids: psiCHECK2-UT (A), psiCHECK2-T141 (B), and psiCHECK2-T200c (C). psiCHECK2-T141 and -T200c have insertion sequences that are fully complementary to mature miR-141 (23 bp) and miR-200c (23 bp), respectively, immediately downstream of the Renilla luciferase gene (D).

Figure 23:
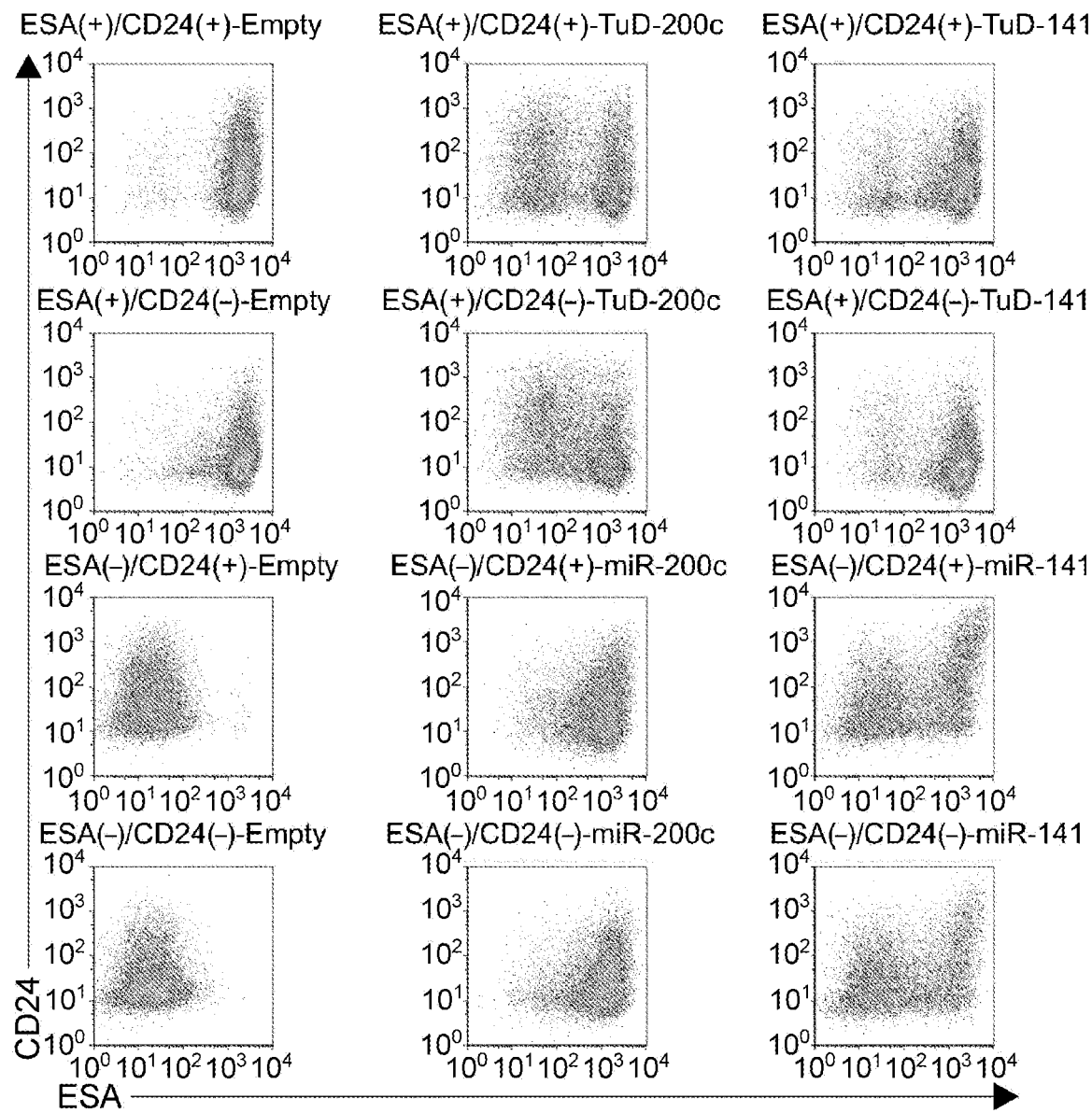

FIG. 23. Effect of modulation of miR-200c and miR-141 activities on the ESA/CD24 expression profile. (A and B) The TuD-200c, TuD-141, miR-200c, or miR-141 expression lentiviral vector was introduced into cells of the parallel cultures used in FIG. 10-1A (lower panel). Two days after introduction, ESA(+)/CD24(+), ESA(+)/CD24(−), ESA(−)/CD24(+), and ESA(−)/CD24(−) subpopulations were sorted by FACS, and cultured for 27 days. Then, their ESA/CD24 expression profiles were analyzed by FACS.

Figure 24:
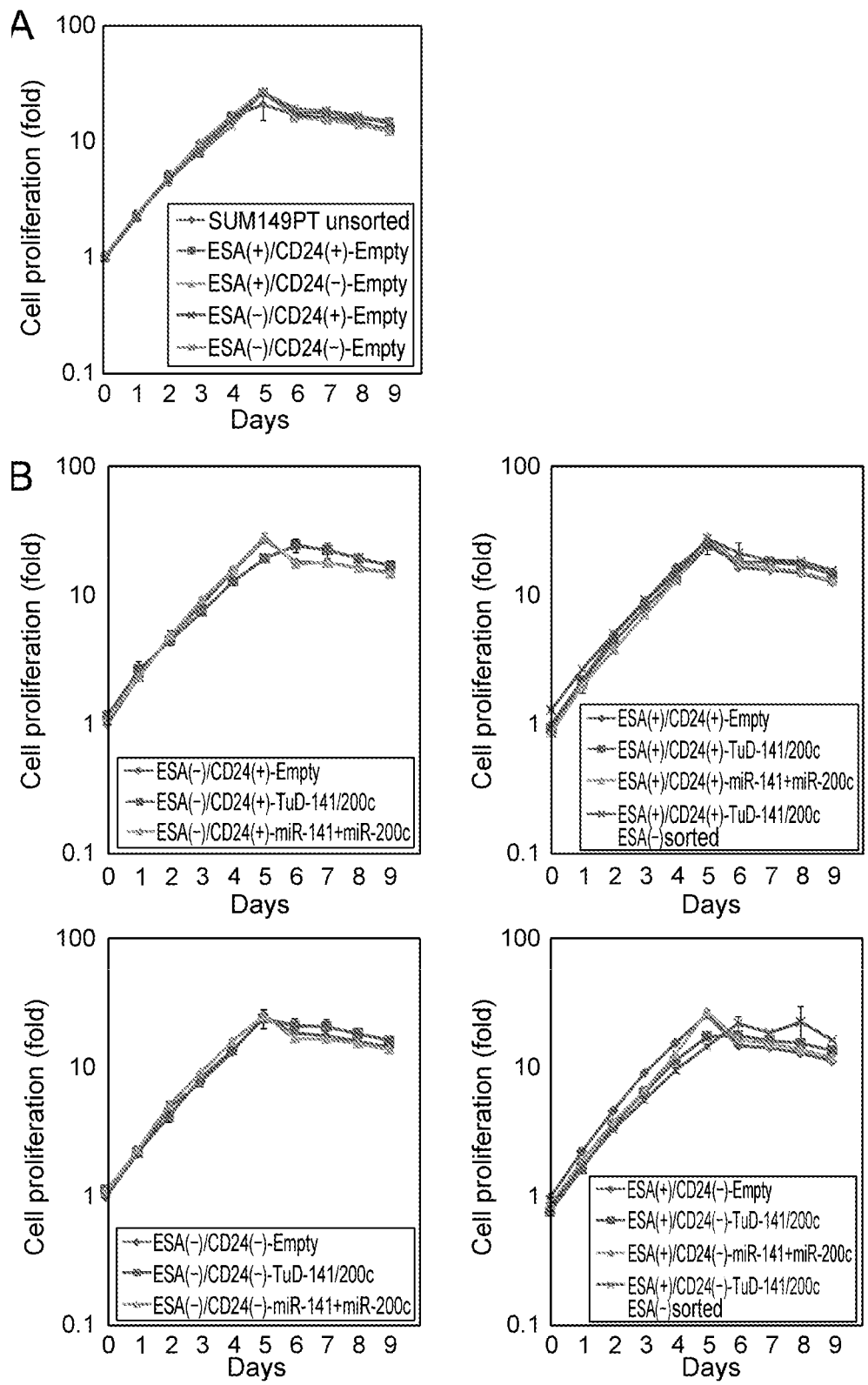

FIG. 24. Growth rate of each subpopulation and vector-introduced cells thereof (A) The cell counts of unsorted parent SUM149PT, and its ESA(+)/CD24(+), ESA(+)/CD24(−), ESA(−)/CD24(+), and ESA(−)/CD24(−) subpopulations were monitored by CellTiterGlo assay, and represented as mean±SD (n=3) after normalizing them by that of unsorted SUM149PT on day 0. (B) ESA(+)/CD24(+), ESA(+)/CD24(−), ESA(−)/CD24(+), and ESA(−)/CD24(−) cells introduced with the TuD-141/200c or miR-141+miR-200c lentiviral vector were monitored by CellTiterGlo assay, and represented as mean±SD (n=3) after normalizing them by that of the cells introduced with an empty lentiviral vector on day 0.

Figure 25:
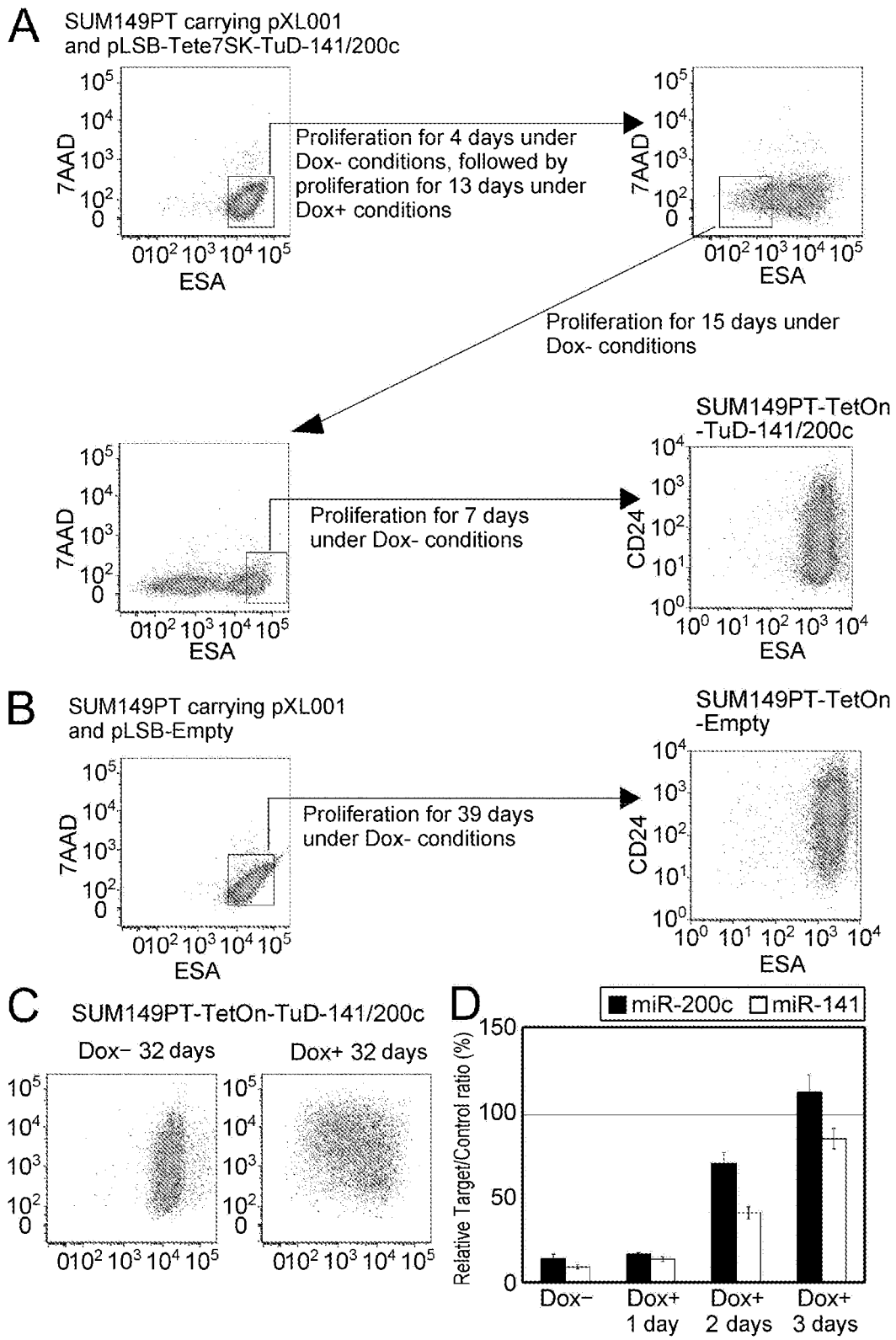

FIG. 25. Preparation of SUM149PT-TetOn-TuD-141/200c cells which are ESA(+) cells having a Tet-inducible TuD-141/200c cassette (A), and their characterization (B). (A) Schematic diagram for preparation of SUM149PT-TetOn-TuD-141/200c cells. Either pLSB-Tete7SK-TuD-141/200c or pLSB-Empty was introduced into SUM149PT cells containing pXL001, followed by blasticidin selection. (A) An ESA(+) fraction from the above-described vector-introduced cells was maintained for 13 days in the presence of Dox, and then an ESA(−) fraction was sorted and allowed to proliferate in the absence of Dox for 15 days. An ESA(+) fraction was sorted from this culture and allowed to proliferate in the absence of Dox. This cell fraction SUM149pT-TetOn-TuD-141/200c, highly responsive to Dox treatment, was injected to mice. (B) Cells introduced with pLSB-Empty were sorted, and ESA(+) cells were allowed to proliferate for 39 days. This culture, SUM149pT-TetOn-Empty, was injected to mice. (C) The parallel culture of SUM149PT-TetOn-TuD-141/200c cells used in the micro-injection shown in FIG. 18 was in vitro cultured for 32 days under either Dox(−) or Dox(+) conditions, and analyzed by FACS for their ESA/CD24 expression profiles. (D) Another parallel culture was in vitro cultured under either Dox(−) or Dox(+) conditions, and dual luciferase reporters were introduced 48 hours before the indicated time points. The expression ratios of miR-200c-RL/FL to UT-RL/FL and of miR-141-RL/FL to UT-RL/FL were represented as mean±SD (n=3).

Figure 26:
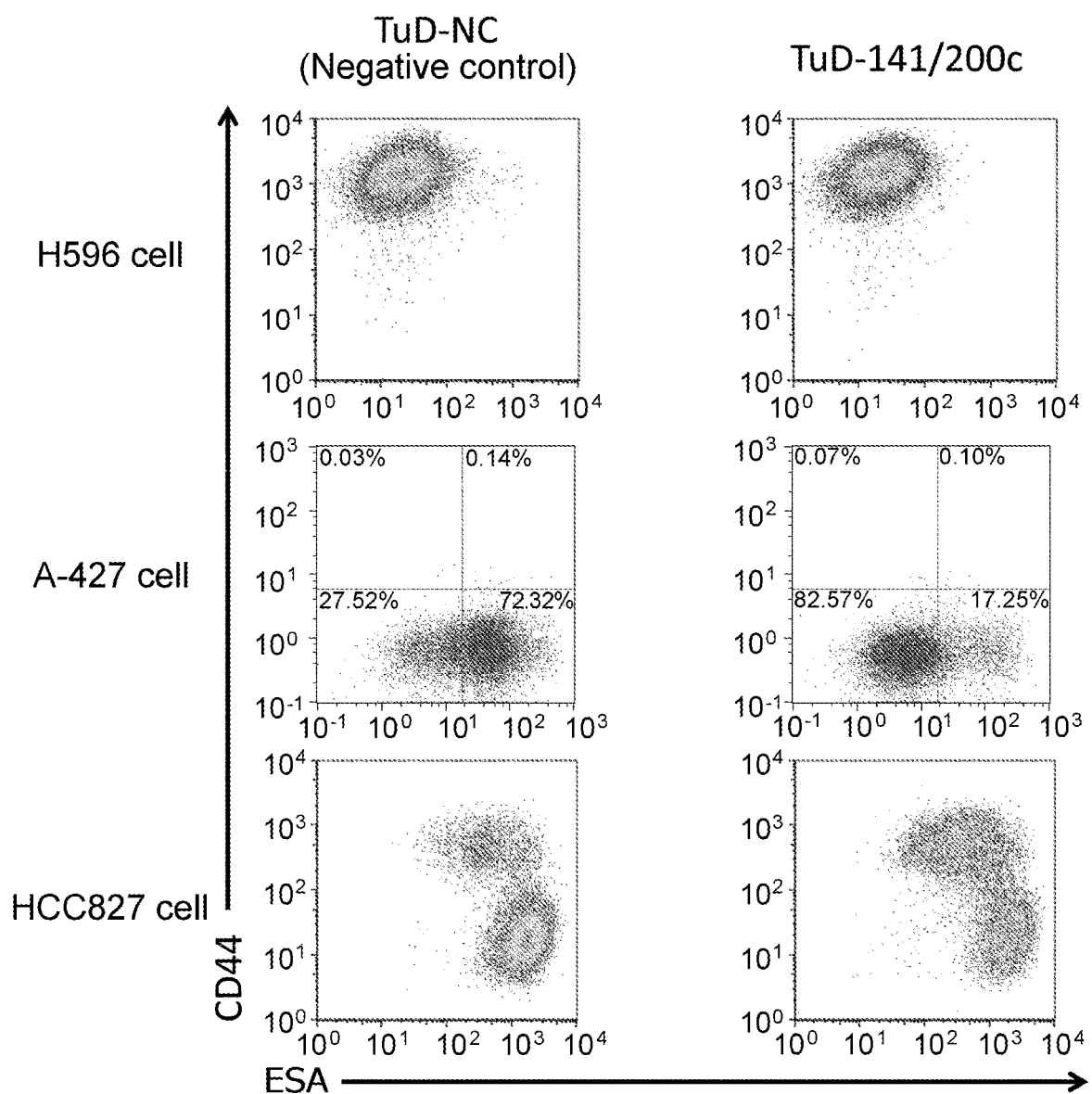

FIG. 26. Effect of introduction of the TuD-141/200c or TuD-NC (control) vector on ESA/CD44 expression profile in non-small cell lung cancer cell lines. The TuD-141/200c or TuD-NC vector was introduced into non-small cell lung cancer cell lines H596, A-427, and HCC827. Two or more weeks after introduction, the cells were analyzed by FACS or MACS for their ESA/CD44 expression profiles.

Figure 27:
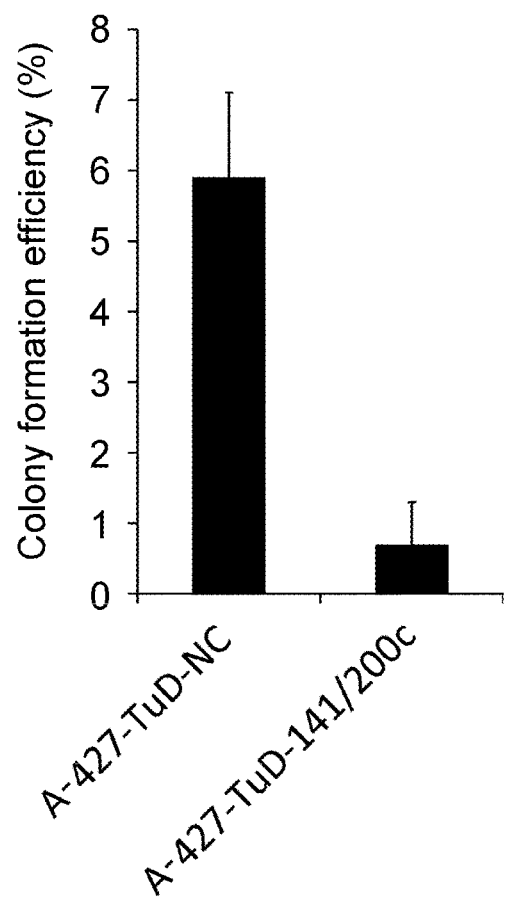

FIG. 27. Tumorsphere formation activity of non-small cell lung cancer cell line A-427 introduced with the TuD-NC (control) or TuD-141/200c vector. The tumorsphere formation efficiency of single cells sorted from A-427 cells introduced with the virus. Spherical tumorspheres were counted, and the colony formation efficiency (%) was represented as mean±SD (n=3).

Figure 28:
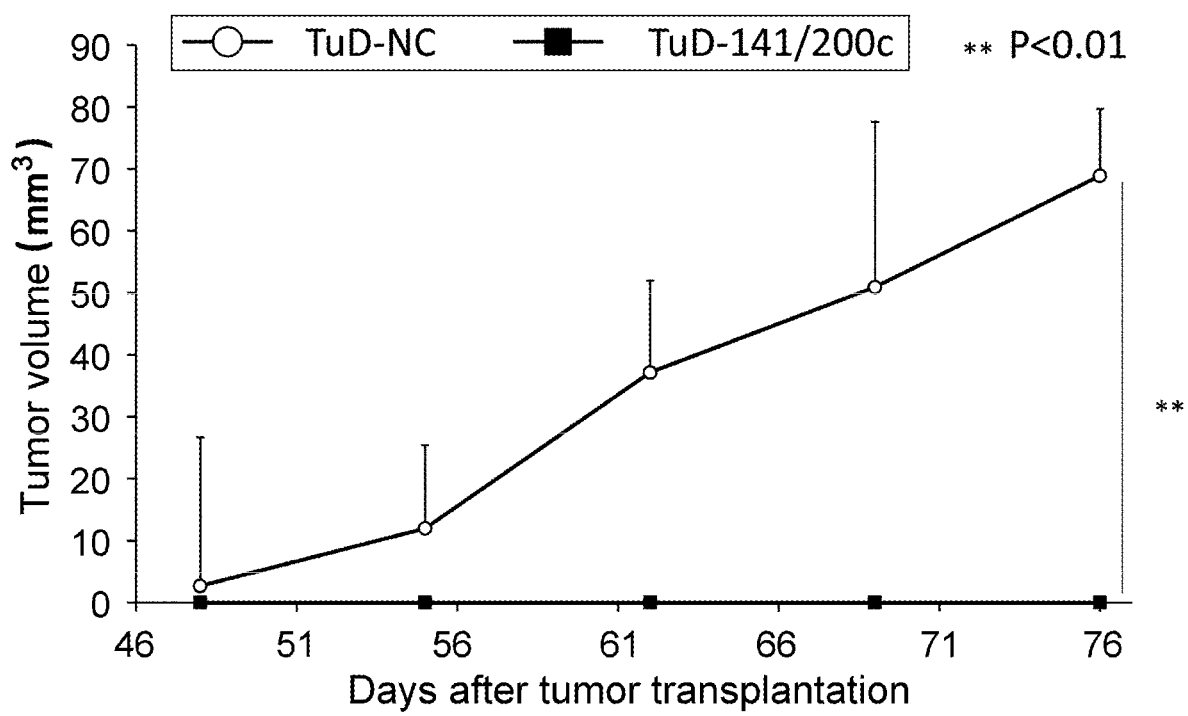

FIG. 28. Tumorigenicity of non-small cell lung cancer cell line H596 introduced with the TuD-NC (control) or TuD-141/200c vector. 10,000,000 vector-introduced cells were injected in the right flank. Tumor volume was measured and represented as mean+SD (n=5), and analyzed by two-way ANOVA using Tukey post-hoc test (**P<0.01).

MODE FOR CARRYING OUT THE INVENTION

The present invention relates to methods for suppressing tumor by inhibiting both of at least one miRNA containing 5'-AACACUG-3' as a seed sequence and at least one miRNA containing 5'-AAUACUG-3' as a seed sequence. Herein, tumor suppression may be any of suppression of tumorigenicity of tumor cells, suppression of tumor formation or growth, and regression of tumor. These can be measured using as an indicator, for example, in vivo tumor mass formation (for example, frequency of formation), the size, or growth rate when tumor cells are injected into animals.

The tumor suppression of the present invention is also characteristic in that it not only targets cancer stem cells but also can simultaneously prevent conversion from non-cancer stem cells to cancer stem cells. Thus, in the present invention, tumor suppression includes achieving both (i) suppression of tumor formation from cancer stem cells and (ii) suppression of conversion from non-cancer stem cells to cancer stem cells. Specifically, tumor suppression by the present invention not only achieves suppression of tumor formation from subpopulations with relatively increased tumorigenicity in a tumor cell population, but also exerts the effect of converting cells that belong to a subpopulation with relatively increased tumorigenicity to those of a subpopulation with relatively low tumorigenicity, and further prevents cells that belong to a subpopulation with relatively low tumorigenicity from converting to cells with relatively increased tumorigenicity. Thus, the tumor suppression of the present invention can not only suppress the tumorigenicity of highly tumorigenic cancer cells that have already occurred (for example, cancer stem cells), but also convert those cancer cells to less tumorigenic cancer cells (non-cancer stem cells) and further suppress conversion of less tumorigenic cancer cells to highly tumorigenic cancer cells. This tumor suppression of the present invention, which can not only target cancer stem cells but also simultaneously prevent the generation of cancer stem cells from non-cancer stem cells is highly useful in clinical applications. Furthermore, at early stages before and after the onset of cancer, the tumor suppression of the present invention can be expected to preventively suppress tumor formation. Thus, in preferred embodiments of the present invention, the "tumor suppression" refers to suppression in which both suppression of tumor formation from a tumor cell subpopulation with increased tumorigenicity and suppression of generation of a tumor cell subpopulation with increased tumorigenicity in a tumor cell population are achieved.

Fractionation of a tumor cell population into subpopulations can be achieved by using desired markers or such. For example, epithelial markers can be used as an indicator for fractionation into subpopulations. Epithelial markers can be selected from any of, for example, ESA (epithelial specific antigen), CDH1 (Cadherin-1), CDH3 (Cadherin-3), and ESRP1 (epithelial splicing regulatory protein 1), and more preferably include ESA, but are not limited thereto. These markers may also be used in combination. When an epithelial marker-positive subpopulation has relatively higher tumorigenicity than a negative subpopulation, the positive subpopulation is a subpopulation with relatively increased tumorigenicity (a group of cells with high tumorigenicity) and the negative subpopulation is a subpopulation with relatively low tumorigenicity (a group of cells with low tumorigenicity).

Meanwhile, a seed sequence refers to the nucleotide sequence from nucleotide positions 2 to 8 from the 5' end of a miRNA. miRNAs containing 5'-AACACUG-3' as a seed sequence include miR-200a (5'-UAACACUGUCUG-GUAACGAUGU-3', SEQ ID NO: 1) and miR-141 (5'-UAACACUGUCUGGUAAAGAUGG-3', SEQ ID NO: 2). Meanwhile, miRNAs containing 5'-AAUACUG-3' as a seed sequence include miR-200b (5'-UAAUACUGCCUG-GUAAUGAUGA-3', SEQ ID NO: 3), miR-200c (5'-UAAUACUGCCGGGUAAUGAUGGA-3', SEQ ID NO: 4), and miR-429 (5'-UAAUACUGUCUG-GUAAAACCGU-3', SEQ ID NO: 5).

Figure 5:
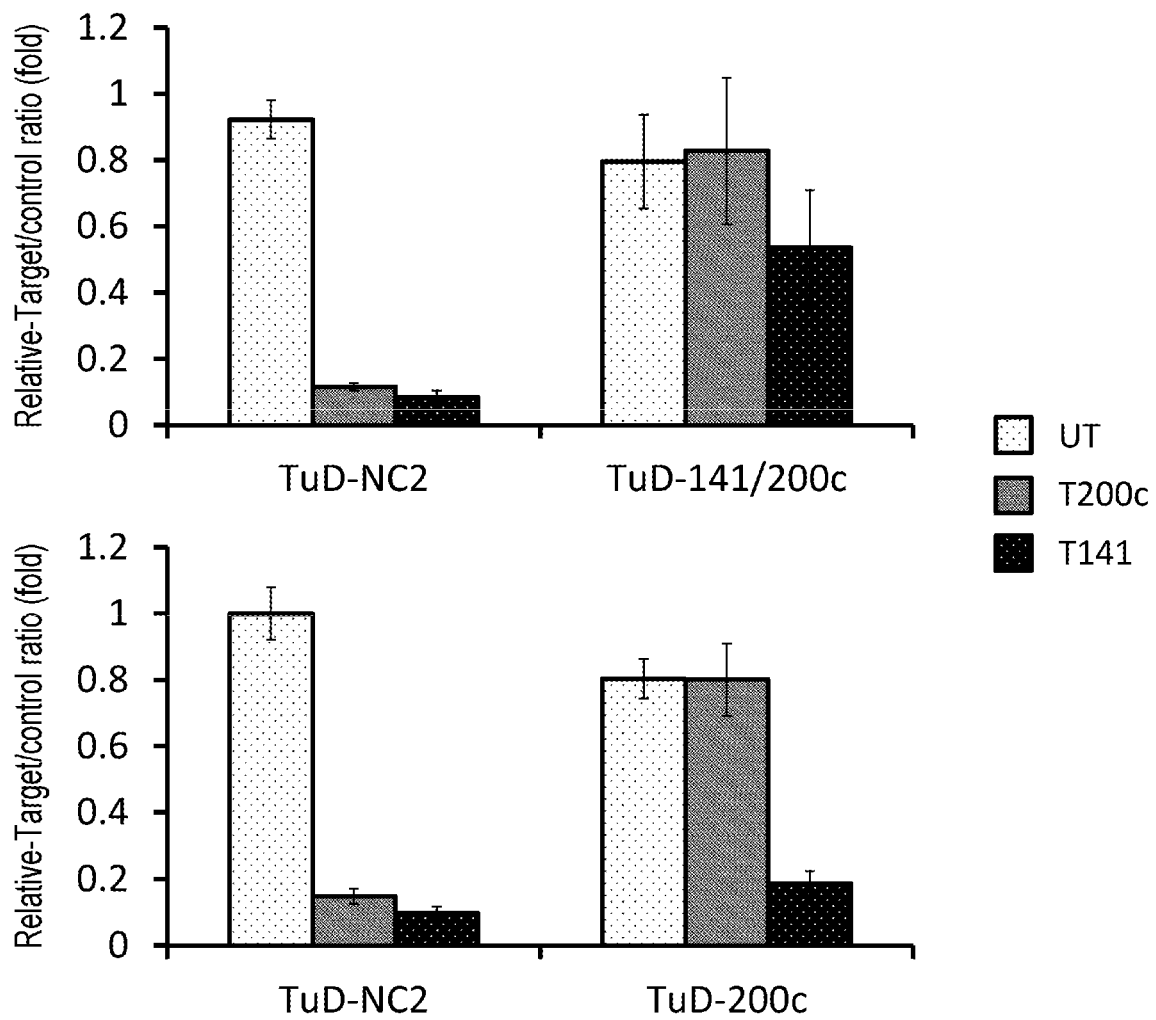
FIG. 5. Effect of TuD-200c and TuD-141/200c on miR-200c and miR-141. Lentiviral expression vectors Tete7SK-TuD-200c and Tete7SK-TuD-141/200c were introduced into HCT116-TetOnIII cells, followed by drug selection. The cells were named HCT116-TetOn-TuD-200c and HCT116-TetOn-TuD-141/200c, respectively. These cells were cultured under Dox+ for 30 days or more. The activity of both miR-200c and miR-141 was determined by measuring luciferase activity two days after reporter plasmid transfection.

As shown in Example 1-3, the use of only an inhibitor against miR-200c which contains 5'-AAUACUG-3' as a seed sequence can hardly suppress the activity of miR-141 which contains 5'-AACACUG-3' as a seed sequence (FIG. 5). This suggests that, because of the single-nucleotide difference between the two seed sequences, an inhibitor against one of the miRNAs cannot effectively inhibit the other miRNA. The present invention revealed that the marked anti-tumor activity demonstrated by the present invention can be exerted by combined use of two miRNAs which inhibit the respective miRNAs.

The above-described methods of the present invention preferably inhibit at least miR-200c and miR-141. In cells subjected to the inhibition, the activity of each miRNA is, for example, ⅓ or less, preferably for example, ¼ or less, ⅕ or less, ⅙ or less, ⅐ or less, ⅛ or less, or ⅑ or less, when compared to the activity of each miRNA without inhibition. More preferably, the activity is, for example, 10% or less, 8% or less, 5% or less, or 3% or less. More preferably, the methods of the present invention inhibit all of miR-200a, miR-200b, miR-200c, miR-141, and miR-429. The activity of each miRNA is, for example, ⅓ or less, preferably for example, ¼ or less, ⅕ or less, ⅙ or less, ⅐ or less, ⅛ or less, or ⅑ or less, when compared to the activity of each miRNA without inhibition. More preferably, the activity is, for example, 10% or less, 8% or less, 5% or less, or 3% or less. Preferably, the methods of the present invention inhibit all members of the miR-200 family. The activity can be measured, for example, by using the reporter assay described in the Examples.

The methods for inhibiting miRNAs are not particularly limited, and methods known to those skilled in the art can be used as appropriate. For example, inhibition can be achieved by using a nucleic acid or analog thereof which binds to the seed sequence of a miRNA. Such a nucleic acid or analog thereof has a sequence that is complementary to the seed sequence. Such miRNA inhibitors include appropriate inhibitors known to those skilled in the art, including, for example, antagomiR (Krutzfeldt, J. et al., 2005, Nature 438:685-689), miRNA target mimicry, and miRNA sponge (Chitwood, D. H. and Timmermans, M. C., 2007, Nat Genet 39:935-936; Ebert, M. S. et al., 2007, Nat Methods 4:721-726; Franco-Zorrilla, J. M. et al., 2007, Nat Genet 39: 1033-1037) as well as other decoys, for example, TuDs (WO2010/047216).

Furthermore, it is possible to use, for example, miRID-IAN (Thermo Scientific), miRCURY (Exiqon), miR-Zip (System Bioscience), and miRNA eraser (MBC, 2008 19(8), 3272-3282).

Moreover, when at least one miRNA containing 5'-AACACUG-3' as a seed sequence and at least one miRNA containing 5'-AAUACUG-3' as a seed sequence are inhibited, irrespective of whether both are inhibited by two different inhibitors or by a single inhibitor, it is preferable that they are inhibited by two distinct inhibition sites separately possessed by the inhibitor(s): one for inhibition of at least one miRNA containing 5'-AACACUG-3' as a seed sequence, and the other for inhibition of at least one miRNA containing 5'-AAUACUG-3' as a seed sequence. In the present invention, such miRNA inhibitors are referred to as inhibitors which inhibit both of at least one miRNA containing 5'-AACACUG-3' as a seed sequence (first miRNA) and at least one miRNA containing 5'-AAUACUG-3' as a seed sequence (second miRNA) using different inhibitory sites. In this case, the inhibitory site in the miRNA inhibitor that inhibits the first miRNA is different from the inhibitory site in the miRNA inhibitor that inhibits the second miRNA.

Specifically, for example, the inhibitory site in the miRNA inhibitor that inhibits the first miRNA contains a sequence complementary to the seed sequence of the first miRNA, while the inhibitory site in the miRNA inhibitor that inhibits the second miRNA contains a sequence complementary to the seed sequence of the second miRNA. Such inhibition includes, for example, miRNA inhibition using a miRNA inhibitor molecule containing a sequence complementary to the seed sequence of the first miRNA and a miRNA inhibitor molecule containing a sequence complementary to the seed sequence of the second miRNA. An alternative example is, as shown in Examples, miRNA inhibition achieved by using a miRNA inhibitor which contains within its molecule a miRNA inhibitory site containing a sequence complementary to the seed sequence of the first miRNA and a miRNA inhibitory site containing a sequence complementary to the seed sequence of the second miRNA.

Thus, in the present invention, a miRNA inhibitor that has two or more miRNA inhibitory sites each of which has been designed to target a different miRNA portion (for example, to target a different miRNA) is referred to as a hybrid miRNA inhibitor. A miRNA inhibitor of the present invention is preferably a hybrid miRNA inhibitor that contains an inhibitory site against at least one miRNA containing 5'-AACACUG-3' as a seed sequence and an inhibitory site against at least one miRNA containing 5'-AAUACUG-3' as a seed sequence.

Cancer to be a target of suppression in the present invention is not particularly limited, but is preferably cancer originating from epithelium or at least partly having an epithelial trait, for example, carcinoma. Cancer to be a target of suppression in the present invention is preferably cancer at least containing a population of cells expressing an epithelial marker, more preferably cancer that contains a population of cells expressing an epithelial marker as a major cell population (specifically, cancer in which the population of cells that do not express any epithelial marker accounts for less than half). The epithelial marker may be any one selected from, for example, ESA (epithelial specific antigen), CDH1 (Cadherin-1), CDH3 (Cadherin-3), and ESRP1 (epithelial splicing regulatory protein 1), and is more preferably ESA, but is not limited thereto. Alternatively, these markers may be used in combination. Such cancer contains cells expressing any (for example, ESA) of the epithelial markers (for example, ESA$^+$ cells) in a proportion of 0.3% or more, preferably 0.5% or more, 1% or more, 2% or more, 3% or more, 5% or more, 7% or more, 10% or more, 15% or more, 20% or more, 25% or more, 30% or more, 40% or more, 50% or more, 60% or more, 70% or more, 80% or more, or 90% or more. The present invention provides methods for testing cancer which comprise the step of examining whether tumor cells include epithelial marker-positive cells. Meanwhile, cancer to be a target of suppression in the present invention is preferably cancer in which inhibition of both at least one miRNA containing 5'-AACACUG-3' as a seed sequence and at least one miRNA containing 5'-AAUACUG-3' as a seed sequence promotes the epithelial-mesenchymal transition and/or suppresses the mesenchymal-epithelial transition. Furthermore, cancer to be a target of suppression in the present invention is preferably cancer in which expression of both at least one miRNA containing 5'-AACACUG-3' as a seed sequence and at least one miRNA containing 5'-AAUACUG-3' as a seed sequence promotes the mesenchymal-epithelial transition and/or suppresses the epithelial-mesenchymal transition. Moreover, cancer to be a target of suppression in the present invention is preferably cancer in which inhibition of miR- 200c and miR-141 promotes the epithelial-mesenchymal transition and/or suppresses the mesenchymal-epithelial transition. Furthermore, cancer to be a target of suppression in the present invention is preferably cancer in which expression of miR-200c and miR-141 promotes the mesenchymal-epithelial transition and/or suppresses the epithelial-mesenchymal transition.

Meanwhile, whether tumor cells at least contain a cell population expressing an epithelial marker may be examined prior to tumor suppression, although this is not essential. Specifically, in one embodiment, the methods of the present invention include those which comprise the step of examining, prior to tumor suppression, whether tumor cells at least contain a cell population expressing an epithelial marker. For example, in one embodiment, the methods of the present invention include those which comprise the step of examining, prior to tumor suppression, whether tumor cells at least contain a cell population expressing an epithelial marker, and suppressing the tumor for which the promotion has been confirmed. Furthermore, whether the epithelial-mesenchymal transition is promoted in tumor cells by inhibiting the miRNAs may be examined prior to tumor suppression, although this is not essential. Specifically, in one embodiment, the methods of the present invention include those which comprise the step of examining whether the epithelial-mesenchymal transition is promoted in tumor cells by inhibiting the miRNAs prior to tumor suppression. For example, in one embodiment, the methods of the present invention include those which comprise the step of examining whether the epithelial-mesenchymal transition is promoted by inhibiting the miRNAs in tumor cells prior to tumor suppression, and suppressing the tumor for which the promotion has been confirmed. However, the present invention is obviously not limited to such methods. The present invention also provides methods for diagnosing cancer which comprise the step of examining whether the epithelial-mesenchymal transition is promoted in tumor cells by inhibiting the miRNAs.

Meanwhile, cancer to be a target of suppression in the present invention include, for example, those which contain a subpopulation with epithelial traits ($sp^E$) and a subpopulation with mesenchymal traits ($sp^M$). Such cancers include, for example, those which contain an epithelial marker-positive cell subpopulation, and an epithelial marker-negative (or low-expressing) or mesenchymal marker-positive cell subpopulation. Preferably, cancer to be a target of suppression in the present invention contains 0.3% or more, preferably, 0.5% or more, 1% or more, 2% or more, 3% or more, 5% or more, 7% or more, 10% or more, 15% or more, 20% or more, 25% or more, or 30% or more of each of both an epithelial marker-expressing cell subpopulation and an epithelial marker-negative or low epithelial marker-expressing (or mesenchymal marker-positive) cell subpopulation. The proportion of a subpopulation may be determined directly from the collected cancer cells or after culturing the cancer cells in a desired medium including, for example, DMEM and Ham's F-12 medium. If necessary, 5-10% fetal bovine serum (FBS) or such can be added for the assay. Furthermore, it is possible to determine, prior to tumor suppression, the proportion between an epithelial marker-expressing cell subpopulation and a epithelial marker-negative or low epithelial marker-expressing (or mesenchymal marker-positive) cell subpopulation in tumor cells. However, the present invention is not limited to such inventions.

Moreover, cancer to be a target of suppression in the present invention preferably contains cancer stem cells within a subpopulation with epithelial traits ($sp^E$). A cancer stem cell refers to a cell that has the ability to form a tumorsphere in the tumorsphere formation assay described in the Examples of the present application, or to a cell that has the ability to form tumor in a tumor formation experiment using animals. A cancer stem cell that belongs to a subpopulation with epithelial traits ($sp^E$) is referred to as an epithelial-trait cancer stem cell or an epithelial cancer stem cell. The presence of cancer stem cells can be confirmed by examining whether a cell population has tumorigenicity, for example, by performing tumorsphere formation assay according to the Examples, or by grafting the cells into mice or such and testing tumor formation.

Prior to tumor suppression, the target tumor may be examined as to whether it contains epithelial-trait cancer stem cells. Specifically, in one embodiment, the methods of the present invention include those which comprise the step of examining, prior to tumor suppression, whether the target tumor contains epithelial-trait cancer stem cells. For example, in one embodiment, the methods of the present invention include those which comprise the step of examining, prior to tumor suppression, whether the target tumor contains epithelial-trait cancer stem cells, and suppressing the cancer that has been found to contain epithelial-trait cancer stem cells in accordance with the methods of the present invention described above.

Furthermore, cancer to be a target of suppression in the present invention is preferably a cancer in which the tumorigenicity of a subpopulation with epithelial traits ($sp^E$) is higher than that of the remaining populations (for example, a subpopulation with mesenchymal traits: $sp^M$) or the whole cancer cells. Herein, such a cancer is referred to as epithelial-trait subpopulation tumorigenic tumor ($sp^E$ tumorigenic tumor) or epithelial trait tumorigenic tumor. Tumorigenicity can be measured, for example, by assaying formation of tumorspheres in accordance with the description of the Examples, or by grafting cells into mice or such and detecting tumor formation or measuring tumor size. For example, a subpopulation with epithelial traits ($sp^E$) is separated from tumor cells. Tumorigenicity assay is performed with the same number of cells, using the remaining populations (for example, a subpopulation with mesenchymal traits: $sp^M$) or the whole cancer cells as a control group. When the tumorigenicity of $sp^E$ is higher, the cancer is determined to be an epithelial trait tumorigenic tumor, in which the tumorigenicity of the subpopulation with epithelial traits ($sp^E$) is higher than that of the remaining populations or the whole cancer cells. Subpopulations with epithelial traits can be isolated and identified using an appropriate epithelial marker. The epithelial marker may be arbitrarily selected from, for example, ESA, CDH1, CDH3, and ESRP1. The present invention also relates to methods for diagnosing or classifying cancer, which comprise the step of examining whether the tumorigenicity of a subpopulation with epithelial traits ($sp^E$) is greater than that of a subpopulation without epithelial traits or the whole cancer cells in a tumor.

Moreover, in the present invention, a target tumor may be examined prior to tumor suppression as to whether the tumorigenicity of a subpopulation with epithelial traits ($sp^E$) is higher than that of the remaining populations (for example, a subpopulation with mesenchymal traits: $sp^M$) or the whole cancer cells. Specifically, in one embodiment, the methods of the present invention include those which comprise the step of examining, prior to tumor suppression, whether the tumorigenicity of a subpopulation with epithelial traits ($sp^E$) is higher than that of the remaining populations (for example, a subpopulation with mesenchymal traits: sp$^M$) or the whole cancer cells in a target tumor. For example, in one embodiment, the methods of the present invention include those which comprise the step of examining, prior to tumor suppression, whether the tumorigenicity of a subpopulation with epithelial traits (sp$^E$) is higher than that of the remaining populations (for example, a subpopulation with mesenchymal traits: sp$^M$) or the whole cancer cells in a target tumor, and suppressing the tumor in which the tumorigenicity of sp$^E$ has been determined to be higher in accordance with the methods of the present invention described above.

Furthermore, cancer to be a target of suppression in the present invention is preferably a cancer that is positive for the expression of both at least one miRNA containing 5'-AACACUG-3' as a seed sequence and at least one miRNA containing 5'-AAUACUG-3' as a seed sequence (double miR-200-positive tumor subpopulation). Specifically, such cancer is a cancer that is positive for at least any one of miR-200a and miR-141 (more preferably miR-141) and is also positive for at least any one of miR-200b, miR-200c, and miR-429 (preferably miR-200c). In the present invention, a target tumor may be examined prior to tumor suppression as to whether it is a double miR-200-positive tumor subpopulation. Specifically, in one embodiment, the methods of the present invention include those which comprise the step of examining, prior to tumor suppression, whether a target tumor is positive for the expression of both at least one miRNA containing 5'-AACACUG-3' as a seed sequence and at least one miRNA containing 5'-AAUACUG-3' as a seed sequence. For example, in one embodiment, the methods of the present invention include those which comprise the step of examining, prior to tumor suppression, whether a target tumor is positive for the expression of both at least one miRNA containing 5'-AACACUG-3' as a seed sequence and at least one miRNA containing 5'-AAUACUG-3' as a seed sequence, and suppressing the tumor that has been found to be positive in accordance with the methods of the present invention described above.

Alternatively, a target cancer in the suppression of the present invention is preferably a cancer that expresses at least one member of the miR-200 family from each locus of two chromosomal loci of the miR-200 family (tumor positive for two miR-200 gene loci). Specifically, such cancer is a cancer that is positive for the expression of at least any one of miR-200a, miR-200b, and miR-429, and the expression of at least either of miR-200c and miR-141. In the present invention, it is also possible to test, prior to tumor suppression, whether a target tumor is a tumor positive for two miR-200 gene loci. Specifically, in one embodiment, the methods of the present invention include those which comprise the step of testing, prior to tumor suppression, whether a target tumor is positive for at least any one of miR-200a, miR-200b, and miR-429, and at least either of miR-200c and miR-141. For example, in one embodiment, the methods of the present invention include those which comprise the step of testing, prior to tumor suppression, whether a target tumor is positive for the expression of at least any one of miR-200a, miR-200b, and miR-429 and the expression of at least either of miR-200c and miR-141 and suppressing the confirmed tumor by a method of the present invention described herein above.

Specifically, cancer to be a target of suppression in the present invention includes colorectal cancer, lung cancer, and breast cancer. Particularly, cancer to be a target of suppression in the present invention includes tumors that are negative for any of progesterone receptor (PR), estrogen receptor (ER), and HER2 (for example, breast cancer), more preferably includes tumors that are negative for at least progesterone receptor (PR) (for example, breast cancer), and most preferably, triple-negative breast cancer that is negative for all of estrogen receptor, progesterone receptor, and HER2. Cancer to be a target of suppression in the present invention also includes, but are not limited to, prostate cancer, non-small cell lung cancer (NSCLC), and kidney cancer. Furthermore, cancer to be a target of suppression in the present invention is preferably human cancer.

The tumor suppression of the present invention is particularly useful in suppressing, for example, tumor development and growth etc., and produces a prominent suppressive effect against primary tumor, in particular. Herein, the primary tumor means that the organ or tissue from which the tumor is derived is identical to the organ or tissue where the tumor is present. The present invention is particularly useful in suppressing, for example, growth of breast cancer in the breast, growth of colorectal cancer in the colon or rectum, or growth of prostate cancer, non-small cell lung cancer, or kidney cancer in the prostate, lung, or kidney, respectively.

Meanwhile, for example, the mechanism for the growth and progression of primary tumor is known to be different from the mechanism for tumor metastasis. Metastasis requires processes such as detachment of cancer cells from the primary lesion and infiltration into vessels (blood and lymphatic vessels), migration through vessels, adhesion to vascular endothelia in the organ of metastasis, and infiltration into the organ of metastasis. Establishment of metastasis requires that cancer cells can escape from and survive the immune elimination mechanism throughout all these processes. Thus, suppression of metastasis can be achieved by inhibiting any of these processes; however, suppression of primary tumor cannot be achieved unless its proliferative ability, survivability, anti-apoptotic activity, or such is inhibited.

The present invention also relates to use of miRNA inhibitors of the present invention in suppressing tumor and in producing an agent for suppressing tumor. Specifically, the present invention relates to use of one or more inhibitors that alone or in combination inhibit at least one miRNA containing 5'-AACACUG-3' as a seed sequence and at least one miRNA containing 5'-AAUACUG-3' as a seed sequence, in suppressing tumor or in producing an agent for suppressing tumor. The present invention also relates to the miRNA inhibitors that are used to suppress tumor.

More specifically, the present invention relates to use of one or more miRNA inhibitors that alone or in combination inhibit at least one miRNA containing 5'-AACACUG-3' as a seed sequence and at least one miRNA containing 5'-AAUACUG-3' as a seed sequence, in producing an agent for suppressing tumor by administering the miRNA. The present invention also relates to use of one or more miRNA inhibitors that alone or in combination inhibit at least one miRNA containing 5'-AACACUG-3' as a seed sequence and at least one miRNA containing 5'-AAUACUG-3' as a seed sequence, in producing an agent for promoting epithelial-mesenchymal transition and/or suppressing mesenchymal-epithelial transition in tumor cells by administering the miRNA inhibitors. The miRNA inhibitor or inhibitors, alone or in combination, preferably inhibit at least miR-200c and miR-141, more preferably inhibit all members of the miR-200 family consisting of miR-200a, miR-200b, miR-200c, miR-141, and miR-429. Herein, "inhibition of miRNA" means that an inhibitor directly inhibits a target miRNA by binding to (interacting with) the target miRNA. Specifically, in the present invention, it is preferable that miRNA inhibitors directly inhibit miR-200c and miR-141 by binding thereto (interacting therewith), and more preferable that miRNA inhibitors directly inhibit all members of the miR-200 family consisting of miR-200a, miR-200b, miR-200c, miR-141, and miR-429 by interacting therewith.

The present invention also relates to tumor-suppressing agents that contain a miRNA inhibitor of the present invention and a pharmaceutically acceptable carrier. More preferably, the present invention provides tumor-suppressing agents containing a miRNA inhibitor(s) that, alone or in combination, contains a first miRNA-binding sequence that binds to at least one miRNA containing 5'-AACACUG-3' as a seed sequence and a second miRNA-binding sequence that binds to at least one miRNA containing 5'-AAUACUG-3' as a seed sequence, and a pharmaceutically acceptable carrier. Herein, the pharmaceutically acceptable carrier includes desired physiological solutions etc., for example, distilled water, phosphate-buffered physiological saline (PBS), sodium chloride solution, Ringer's solution, and culture media.

The miRNA inhibitors are not particularly limited, and include appropriate miRNA inhibitors known to those skilled in the art. For example, nucleic acids and their analogs that bind to the seed sequence of a target miRNA are suitable. Specifically, as described above, it is possible to use, for example, antagomiR (Krutzfeldt, J. et al., 2005, Nature 438: 685-689), miRNA target mimicry, miRNA sponge (Chitwood, D. H. and Timmermans, M. C., 2007, Nat Genet 39: 935-936; Ebert, M. S. et al., 2007, Nat Methods 4: 721-726; Franco-Zorrilla, J. M. et al., 2007, Nat Genet 39: 1033-1037), miRIDIAN, miRCURY, miR-Zip, miRNA eraser, other miRNA decoys, TuDs (WO2010/047216), and others.

In the present invention, TuDs (tough decoys) can be used particularly preferably as miRNA inhibitors. In the present invention, a TuD refers to a miRNA inhibitor that has a pair of strands each containing at least one miRNA-binding sequence, in which both ends of the pair of strands each containing a miRNA-binding sequence are each linked to one end of each of a pair of multiple-stranded chains (duplex chains and/or quadruplex chains) so as to be flanked by the pair of the multiple-stranded chains. The miRNA inhibitor may be constituted by RNA, or may be constituted by other nucleic acids, nucleic acid analogs, or a combination thereof.

Preferably, a miRNA inhibitor of the present invention can inhibit, by its single molecule, at least one miRNA containing 5'-AACACUG-3' as a seed sequence and at least one miRNA containing 5'-AAUACUG-3' as a seed sequence. Herein, the "molecule" refers not only to a mass of particles where atoms are linked together via covalent bonds but also a mass of substance where the particles stably bind together via hydrogen bonds. Meanwhile, "stably bind via hydrogen bonds" means, for example, binding in nucleic acids or analogs thereof with a total of eight or more base pairs, preferably with a total of 10 or more, more preferably with a total of 12 or more, and still more preferably with a total of 15 or more of base pairs.

For example, when a miRNA inhibitory molecule contains a miRNA-binding sequence to at least one miRNA containing 5'-AACACUG-3' as a seed sequence and a miRNA-binding sequence to at least one miRNA containing 5'-AAUACUG-3' as a seed sequence, one single such miRNA inhibitory molecule can inhibit both miRNAs. Such a miRNA inhibitor, which contains two different miRNA-binding sequences and thereby inhibits at least two different miRNAs by its single molecule, is referred to as a hybrid miRNA inhibitor. Each miRNA-binding sequence contains a nucleic acid or analog thereof complementary to the seed sequence of each miRNA. Specifically, miRNA inhibitors of the present invention preferably inhibit at least miR-200c and miR-141, and such miRNA inhibitors contain, for example, a miRNA-binding sequence to miR-200c and a miRNA-binding sequence to miR-141. Specifically, the miRNA inhibitors contain a sequence complementary to 5'-AACACUG-3' and a sequence complementary to 5'-AAUACUG-3'. A sequence complementary to 5'-AACACUG-3' is for example, 5'-CAGUGUU-3', and a sequence complementary to 5'-AAUACUG-3' is, for example, 5'-CAGUAUU-3'.

More specifically, miRNA-binding sequences that inhibit at least one miRNA containing 5'-AACACUG-3' as a seed sequence include miRNA-binding sequences containing 5'-CAGUGUU-3', including, for example, 5'-CCAUC-UUUACCACAUAGACAGUGUUA-3' (SEQ ID NO: 6), but are not limited thereto. Meanwhile, miRNA-binding sequences that inhibit at least one miRNA containing 5'-AAUACUG-3' as a seed sequence include miRNA-binding sequences containing 5'-CAGUAUU-3', including, for example, 5'-UCCAUCAUUACCCCACUGGC-AGUAUUA-3' (SEQ ID NO: 7), but are not limited thereto.

TuDs of the present invention include, for example, miRNA-inhibiting complexes described in CN Patent No. ZL200980152926.X (CN102264898(B)), specifically, "a miRNA-inhibitory complex comprising an RNA or analog thereof, wherein said complex comprises a double-stranded structure in which strands containing a miRNA-binding sequence are each bound to one of the two strands on one end of said double-stranded structure, and wherein said complex comprises a second multiple-stranded structure selected from a double strand or a quadruple strand, wherein the other ends of said two miRNA-binding sequence-containing strands are each bound to one of the two strands on one end of said second multiple-stranded structure, so that the miRNA-binding sequence-containing strands are placed between said double-stranded structure and said second multiple-stranded structure, whereby the complex comprises a structure shown in FIG. 1, where I represents said double-stranded structure and II represents said second multiple-stranded structure which is a double or quadruple strand, and a and b each contain at least one miRNA-binding sequence" (CN Patent ZL200980152926.X (CN102264898(B)). Herein, the vertical lines of I and II indicate that the chains are multiple-stranded; however, the numbers of base pairs are not limited to the numbers of vertical lines. Furthermore, a and b of FIG. 1 may partially form double-stranded chains as shown in FIG. 2(a).

TuDs of the present invention also include miRNA-inhibiting complexes described in EP Patent No. 2363467 (EP Patent Application No. 09821914.0), specifically, "a miRNA-inhibiting complex comprising an RNA or analog thereof, which comprises a double-stranded structure and a second multiple-stranded structure, wherein strands comprising a miRNA-binding sequence are each bound to one of the two strands on one end of said double-stranded structure, and wherein the other ends of the strands are each bound to one of two strands of the second multiple-stranded structure, so that the strands are placed between the double-stranded structure and the multiple-stranded structure" (EP2363467 (B1)).

TuDs of the present invention also include miRNA-inhibiting complexes described in JP Patent No. 4936343, specifically, "a miRNA-inhibiting complex comprising an RNA or analog thereof, which comprises a double-stranded structure in which ends of two strands containing a miRNA-binding sequence are each bound to one of the two strands on one end of said double-stranded structure via a linker of 1 to 5 nucleotides, wherein the complex comprises a second multiple-stranded structure selected from a double strand or a quadruple strand, wherein the other ends of said two strands containing a miRNA-binding sequence are each bound to one of the two strands on one end of said second multiple-stranded structure via a linker of 1 to 5 nucleotides so that the strands containing a miRNA-binding sequence are placed between said double-stranded structure and said second multiple-stranded structure, wherein said two strands containing a miRNA-binding sequence each contain a miRNA-binding sequence, whereby two miRNA-binding sequence-containing strands are present" (JP Patent No. 4936343).

TuDs of the present invention also include miRNA-inhibiting complexes described in U.S. Pat. No. 8,563,709, specifically, "a miRNA-inhibiting complex comprising an RNA or analog thereof, which comprises:
(a) a double-stranded structure,
(b) a multiple-stranded structure, and
(c) a plurality of strands that each comprise a miRNA-binding sequence, wherein the strands are each bound at one end to one of two strands on one end of said double-stranded structure, and wherein the other ends of the strands are each bound to one of two strands of the multiple-stranded structure, so that the strands are placed between the double-stranded structure and the multiple-stranded structure" (U.S. Pat. No. 8,563,709).

As described above, a miRNA inhibitor such as a TuD may be an inhibitor which can inhibit, by its single molecule, at least one miRNA containing 5'-AACACUG-3' as a seed sequence and at least one miRNA containing 5'-AAUA-CUG-3' as a seed sequence. For this purpose, the inhibitor may contain two miRNA-binding sequences in its single molecule. In the present invention, a TuD containing two miRNA-binding sequences is also referred to as a hybrid TuD. A hybrid TuD preferably contains, for example, 5'-CAGUGUU-3' and 5'-CAGUAUU-3'. Specifically, a hybrid TuD preferably contains at least two miRNA-binding sequences (MBSs): MBS containing 5'-CAGUGUU-3' and MBS containing 5'-CAGUAUU-3'.

Meanwhile, miRNA inhibitors of the present invention may be naturally-occurring nucleic acids, artificial nucleic acids, or nucleic acid analogs. Naturally-occurring nucleic acids can be produced, for example, by transcription from vectors, whereas artificial nucleic acids or nucleic acid analogs can be produced by synthesis or such. In the present invention, synthetic TuDs are also referred to as S-TuDs, and S-TuDs are included in TuDs. In the present invention, a vector that expresses a TuD is also referred to as TuD.

miRNA inhibitors of the present invention such as TuDs are useful as tumor-suppressing agents of the present invention and can be used suitably for suppressing tumor growth or for other purposes.

To illustrate more specifically, for example, miRNA inhibitors (miRNA-inhibiting complexes) of the present invention comprises a double-stranded structure, and at least one strand containing a miRNA-binding sequence (MBS) is bound to two strands of the double-stranded structure on at least one end. In the present invention, this double-stranded structure may be called "first" double-stranded structure so that it can be distinguished from additional double-stranded structures that may be comprised in the miRNA inhibitors of the present invention (see below). In the present invention, a miRNA inhibitor may be composed of a single strand or multiple strands. For example, a miRNA inhibitor composed of a double-stranded RNA in which RNA strands containing an MBS are each bound to one of two strands on one end of the double-stranded structure is preferred as a TuD. Furthermore, for example, a single RNA strand comprising at least one MBS may be linked to the two strands of the double-stranded structure on one end. In this case, the MBS-comprising RNA strand links the two strands on one end of the double-stranded structure (e.g., FIG. 1 of WO2010/047216). The RNA linking the two strands of the double-stranded structure comprises at least one MBS; however, for example, two, three, or more MBSs may be comprised (e.g., FIG. 2A of WO2010/047216).

In the present invention, a miRNA inhibitor such as a TuD may be a structure that has a double-stranded structure and which comprises at least one RNA or analog thereof. Preferably, the structure comprises one or two molecules comprising an RNA or analog thereof.

In the present invention, "miRNA-binding sequence (MBS)" refers to a sequence that binds to a miRNA. An MBS comprises at least a portion complementary to a miRNA so that it can bind to the miRNA. An MBS may or may not have a sequence completely complementary to a miRNA. An MBS may be a naturally-occurring RNA sequence targeted by a miRNA. For example, an MBS consecutively or non-consecutively comprises at least ten nucleotides, such as eleven or more, twelve or more, 13 or more, 14 or more, 15 or more, 16 or more, 17 or more, 18 or more, 19 or more, 20 or more, 21 or more, 22 or more, 23 or more, or 24 or more nucleotides that are complementary to a miRNA. The complementary nucleotides are preferably consecutive, or have a gap at three sites or less, two sites or less, or preferably one site. The gaps may be unpairing (bulges) on the MBS side and/or the miRNA side. Gaps at one site may have bulge nucleotides on only one of the strands, or unpaired nucleotides on both of the strands. Preferably, they are designed to include unpaired nucleotides at least on the MBS side. The number of nucleotides in a single bulge or mismatch is, for example, six nucleotides or less, preferably five nucleotides or less, four nucleotides or less, three nucleotides or less, two nucleotides or less, or one nucleotide on a single strand. In the present invention, an MBS that can form a bulge shows a higher miRNA-inhibiting effect than an MBS consisting of a completely complementary sequence (Example 4 of WO2010/047216). Therefore, to obtain higher miRNA-inhibiting effects, an MBS is designed to preferably form a bulge. For example, the following MBSs are not readily degraded, and their high activity can be expected: an MBS in which the nucleotides at position 10 and/or position 11 from the 3' end are not complementary to a miRNA, or an MBS comprising additional nucleotides that are not complementary to an MBS between positions 10 and 11 (i.e., the nucleotides at position 10 and/or position 11 from the 5' end of a target sequence in a miRNA (a sequence that hybridizes with an MBS), or a miRNA comprises unpaired nucleotides between the nucleotides of positions 10 and 11). In this case, for example, an MBS may be designed so that the nucleotides including those at positions 10 and 11 from the 5' end of a miRNA are unpaired. For example, an MBS may be designed so that nucleotides at positions 9 to 11, 10 to 12, or 9 to 12 are unpaired. Alternatively, an MBS may be designed so that no nucleotide becomes unpaired on the miRNA side, but the MBS has nucleotides that become unpaired between positions 10 and 11 from the 3' end on the MBS side, i.e., between the sites corresponding to positions 10 and 11 from the 5' end of a target sequence (a sequence that hybridizes with the MBS) in a miRNA. Nucleotides that become unpaired may be present on the miRNA side and/or the MBS side. Preferably, they exist at least on the MBS side. The number of nucleotides that become unpaired in each strand can be adjusted appropriately. For example, it is one to six nucleotides, preferably one to five nucleotides, or more preferably three to five nucleotides, such as three, four, or five nucleotides.

It is known that matching of nucleotides at positions 2 to 7 or positions 3 to 8 from the 5' end (called "seed region") of a miRNA is important for target recognition by the miRNA (Jackson A L et al., RNA 12(7):1179-1187, 2006; Lewis B P et al., Cell 120: 15-20, 2005; Brennecke et al. PLoS BIOLOGY 3, 0404-0418, 2005; Lewis et al. Cell 115, 787-798, 2003; Kiriakidou et al. Genes & Development 18, 1165-1178, 2004). In fact, miRNA-inhibiting RNAs can effectively inhibit miRNAs even when they carry an MBS that matches with only the seed region but has low complementarity with other regions (Example 6, FIG. 12 of WO2010/047216). In the present invention, an MBS preferably has complete complementarity to a miRNA seed region (nucleotides at positions 2 to 7 and/or positions 3 to 8 from the 5' end of a miRNA). In this case, a G:U pair (U:G pair) may be considered to be complementary. However, it is preferable to consider only G:C (C:G) and A:U (U:A) pairs as complementary. In the present invention, preferably, an MBS is completely complementary to a miRNA seed region (nucleotides at positions 2 to 7 and/or positions 3 to 8 from the 5' end of a miRNA), and it consecutively comprises at least eight nucleotides, more preferably nine nucleotides, and even more preferably ten nucleotides that are complementary to the miRNA. Furthermore, an MBS of the present invention preferably comprises a total of eleven or more nucleotides, more preferably twelve or more nucleotides, or even more preferably 13 or more nucleotides that are complementary to a miRNA.

Preferably, an MBS is a sequence that hybridizes with a miRNA sequence under physiological conditions. Physiological conditions are, for example, 150 mM NaCl and 15 mM sodium citrate at pH 7.0 and 37° C. More preferably, an MBS is a sequence that hybridizes with a miRNA sequence under stringent conditions. Stringent conditions include, for example, conditions of 1×SSC ("1×SSC" means "150 mM NaCl and 15 mM sodium citrate at pH 7.0") or 0.5×SSC at 42° C., more preferably conditions of 1×SSC or 0.5×SSC at 45° C., and even more preferably conditions of 1×SSC or 0.5×SSC at 50° C. In hybridization, for example, either one of a miRNA sequence-comprising RNA and an MBS-comprising RNA is labeled, and the other is immobilized onto a membrane, and then the two are hybridized. Hybridization may be carried out under conditions such as in a solution containing 5×SSC, 7% (W/V) SDS, 100 µg/mL denatured salmon sperm DNA, and 5×Denhardt's solution (1×Denhardt's solution contains 0.2% polyvinyl pyrrolidone, 0.2% bovine serum albumin, and 0.2% Ficoll), for example at 37° C., 45° C., or 50° C. After incubation for a sufficient time (for example, three, four, five, or six hours or more), washing is carried out under the above conditions. Then, one can determine whether a nucleic acid is hybridized under the conditions by detecting whether the labeled nucleic acid is hybridized.

Alternatively, an MBS preferably shows high homology to the complementary sequence of a miRNA sequence. "High homology" refers to a nucleotide sequence identity of, for example, 70% or more, 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 93% or more, 95% or more, 96% or more, 97% or more, 98% or more, or 99% or more. The nucleotide sequence identity can be determined using, for example, the BLAST program (Altschul, S. F. et al., J. Mol. Biol. 215: 403-410, 1990). For example, in the BLAST web page of the National Center for Biotechnology Information (NCBI), a search can be carried out using default parameters (Altschul S. F. et al., Nature Genet. 3:266-272, 1993; Madden, T. L. et al., Meth. Enzymol. 266:131-141, 1996; Altschul S. F. et al., Nucleic Acids Res. 25:3389-3402, 1997; Zhang J. & Madden T. L., Genome Res. 7:649-656, 1997). For example, an alignment of two sequences can be produced by the blast 2 sequences program (Tatiana A et al., FEMS Microbiol. Lett. 174:247-250, 1999) which compares two sequences, and the sequence identity can be determined. Gaps outside of a miRNA nucleotide sequence are ignored, and inner gaps are treated, for example, in the same manner as mismatches. The value of identity in alignment with the whole miRNA nucleotide sequence (with a total nucleotide length determined by adding the gaps inside the sequence) is calculated. However, as shown in the Examples, a mismatch between an MBS and a miRNA may increase the miRNA-inhibiting activity. Therefore, for example, it is preferable to calculate the identity by ignoring gaps inserted into a miRNA sequence inside alignment.

Alternatively, an MBS preferably comprises a sequence with one or more nucleotide insertions, substitutions, and/or deletions in a sequence complementary to a miRNA sequence. Preferably, an MBS comprises a sequence that has eight or less, seven or less, six or less, five or less, four or less, three or less, two or less, or one nucleotide insertion, substitution, and/or deletion in a sequence complementary to a miRNA sequence. More preferably, an MBS comprises a sequence that has eight or less, seven or less, six or less, five or less, four or less, three or less, two or less, or one nucleotide insertion in a sequence complementary to a miRNA sequence. It has been shown that an MBS with a mismatch sequence has higher miRNA-inhibiting activity than an MBS with a sequence completely complementary to a miRNA sequence (WO2010/047216). This is thought that because when an MBS is completely complementary to a miRNA, it may be cleaved by RISC containing the miRNA, and thus the expression level of the miRNA-inhibiting RNA is decreased. In particular, high activity can be expected from an MBS designed to have unpairing at the nucleotides of position 10 and/or position 11 from the 3' end of the MBS (i.e., the nucleotides at position 10 and/or position 11 from the 5' end of a target sequence in a miRNA that hybridizes with an MBS become unpaired when the miRNA is hybridized with the MBS), or an MBS that is designed to comprise unpaired nucleotides between the nucleotides of positions 10 and 11. Such unpairing may be, for example, a bulge on the MBS side. The number of nucleotides that form the bulge is one to six nucleotides, preferably one to five nucleotides, and more preferably three to five nucleotides (for example, three, four, or five nucleotides).

An MBS may comprise an RNA, or it may comprise a nucleic acid analog, or it may consist of a nucleic acid analog. In particular, the miRNA-inhibiting effect is expected to be increased by converting the cleaved site in an MBS (the nucleotides of position 10 and/or position 11 from the 3' end of the MBS, etc.) into nucleic acid analogs in order to prevent cleavage. Furthermore, it is also favorable to use nucleic acids that have a backbone such as phosphorothioate and 2'-O-methyl, or a sugar (Krutzfeldt, J. et al., Nucleic Acids Res. 35: 2885-2892; Davis, S. et al., 2006, Nucleic Acids Res. 34: 2294-2304).

Furthermore, the above miRNA inhibitors of the present invention such as TuDs may be miRNA inhibitors that comprise a second double-stranded structure in addition to a first double-stranded structure, and which have a structure in which the two strands in the first double-stranded structure on the end to which the MBSs are linked are each linked to one MBS-containing RNA strand, and the other ends of the RNA strands are each linked to one of the two strands of the second double-stranded structure so that the RNA strands are placed between the first double-stranded structure and the second double-stranded structure. This miRNA inhibitor has a structure that comprises at least two double-stranded structures, wherein the four RNA strands constituting the two double-stranded structures are each linked to an RNA comprising an MBS without mediation of any of the remaining three strands. More simply stated, the above miRNA inhibitor is a miRNA inhibitor in which two RNA strands comprising an MBS are each bound to one of the strands of two double-stranded structures so that the strands are placed between the two double-stranded structures (FIG. 1). The two RNA strands comprising an MBS are linked to the respective paired strands in the double-stranded structures. Therefore, the directions of the RNA strands are opposite to each other (FIG. 2, #12 to #16 of WO2010/047216). By adding an MBS to each of the two strands in this manner, higher miRNA-inhibiting activity can be exerted.

In the two RNA strands comprising an MBS present between two double-stranded structures, one or more MBSs are comprised in each strand. These MBSs may have the same or different sequences. Furthermore, they may target the same miRNA, or they may have sequences that bind to different target miRNAs. For example, one strand may comprise two or more, for example, two, three, four, or five MBSs (FIG. 2, #12 to #16 of WO2010/047216) (for example, hybrid TuD). For example, one or two MBSs may be comprised in each strand positioned between two double-stranded structures. For example, a miRNA inhibitor of the present invention such as a TuD may comprise two MBSs in total, and the two MBSs may have the same sequence or sequences that bind to the same miRNA. A TuD with a structure in which the above structure as a unit is tandemly repeated is also preferable (see Examples). The number of repeats may be suitably determined and, for example, it is 2 to 10, preferably 2 to 5 or 3 to 5, for example, 3.

Figure 3:
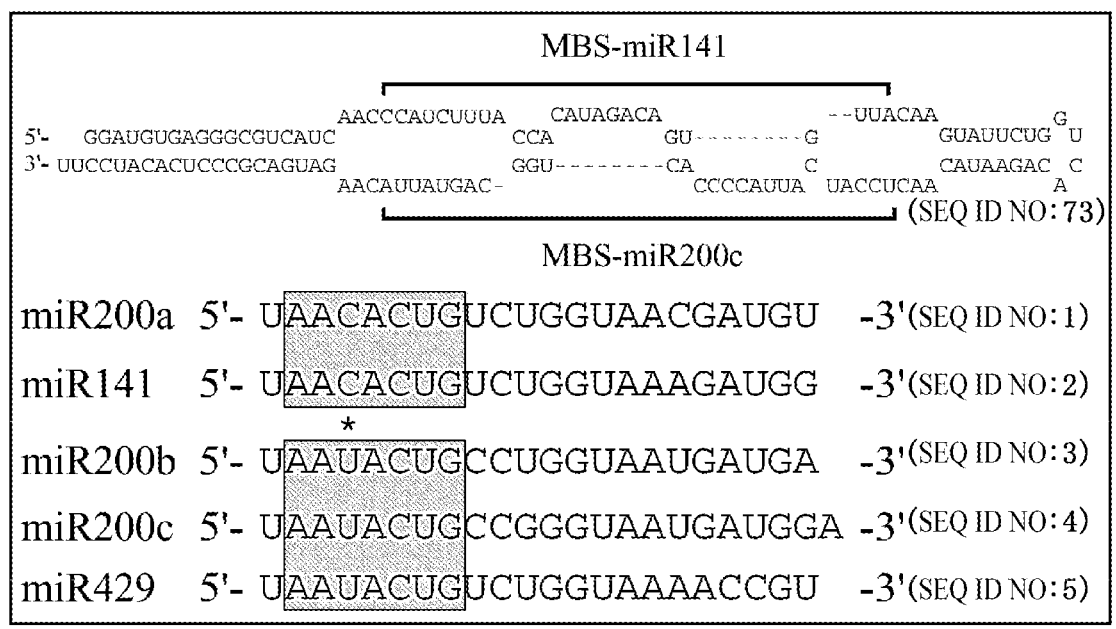
Figure 1:
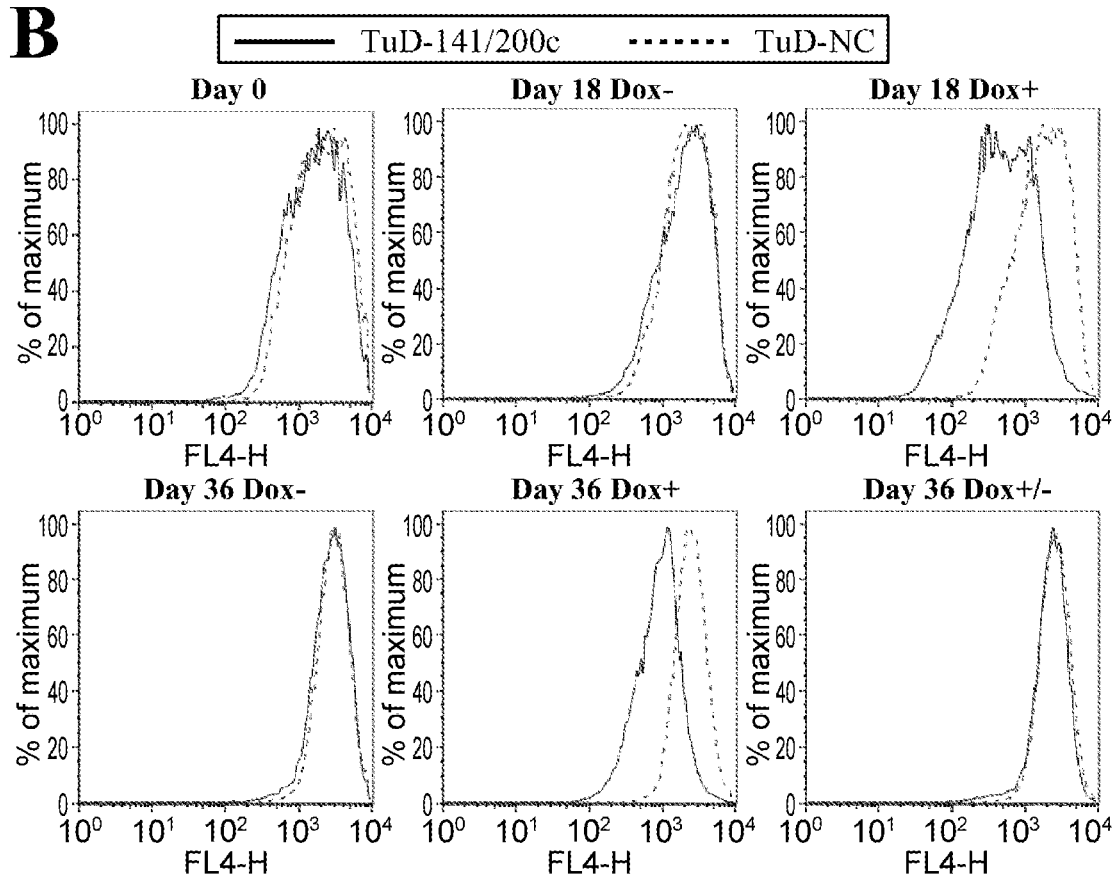

Each of the strands that are paired in a double strand comprised in a miRNA inhibitor of the present invention may be separate RNA strands as described above (i.e. not linked by covalent bonds). Alternatively, one or both ends of the double strand may be linked, and may be linear or cyclic. A miRNA inhibitor composed of a linear single-stranded RNA can be produced, for example, by a one-time RNA synthesis, or it may be expressed from a single expression unit using an expression vector or such. For example, when two double-stranded structures are included, two strands on one end (the side to which an MBS is not bound) of the second double-stranded structure can be linked by a loop so that the whole molecule becomes single-stranded. In the sequence linking the two strands, one or more MBSs may be included (FIG. 2, #2, #11, #14, and #16 of WO2010/047216). To make the sequence as compact as possible, the two strands can be linked by a short loop. For example, the two strands can be linked, for example, by one to ten nucleotides, preferably one to eight nucleotides, two to six nucleotides, three to five nucleotides, for example, four nucleotides. There is no particular limitation on the sequence, and an example is 5'-GUCA-3' (FIG. 3-1A).

There is no particular limitation on the sequences of the double-stranded structures comprised in the miRNA inhibitors of the present invention, but they preferably have a length of four base pairs or more. In particular, at least one of the double-stranded structures comprised in the miRNA inhibitors of the present invention (that is, a first double-stranded structure) has important functions in the nuclear export of the inhibitors. The chain length of this double strand may be, for example, 15 to 50 base pairs, preferably 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, or 45 nucleotides or more, or 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, or 18 nucleotides or less. In a preferred embodiment, the length of the base pairs of the double-stranded structure is, for example, 15 to 30, preferably 16 to 28, more preferably 17 to 25, and even more preferably 17 to 24, for example, 17, 18, 19, 20, 21, 22, 23, or 24. Although high activity can be exerted when the length is longer than 20 bp, dsRNAs with more than 20 bp can be potential targets for cleavage by Dicer in the cytoplasm. Therefore, to avoid this, the length of a double-stranded structure comprised in a miRNA inhibitor of the present invention can be 20 bp or less, for example, 19 bp or less, or 18 bp or less.

Examples include a double-stranded structure composed of positions 1-18 of SEQ ID NO: 73 and positions 104-121 of SEQ ID NO: 73, but are not limited thereto. In the meantime, UU can be added at the 3'-end.

When second or further double-stranded structures are comprised in miRNA inhibitors of the present invention, there is no particular limitation on the sequence and length of such double-stranded structures. For example, the length of these double-stranded structures can be made to be shorter than that of the first double-stranded structure in order to make the whole miRNA inhibitor compact. The chain length of each double strand can be adjusted appropriately, and for example, it may be 4 bp to 20 bp, for example, 5 bp to 15 bp, 5 bp to 12 bp, 5 bp to 10 bp, 6 bp to 9 bp, or 7 bp to 8 bp.

Examples include a double-stranded structure composed of positions 51-58 of SEQ ID NO: 73 (5'-GUAUUCUG-3') and positions 63-70 of SEQ ID NO: 73 (5'-CAGAAUAC-3'), but are not limited thereto.

Figure 6:
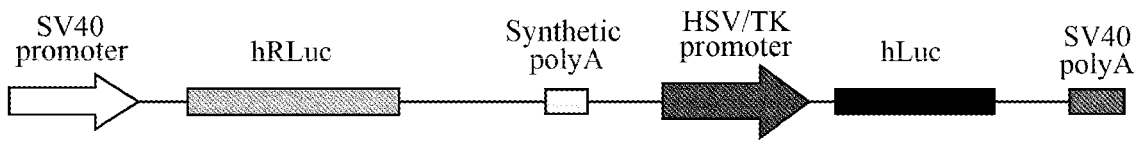
FIG. 6. The structures of luciferase reporters used in the present experiments. The structures of dual luciferase reporter plasmids, psiCHECK2-UT (A), psiCHECK2-T21 (B), psiCHECK2-T200c (C), and psiCHECK2-T141 (D). psiCHECK2-T21, -T200c, and -T141 have insertion sequences that are fully complementary to mature miR-21 (22 bp), miR-200c (23 bp), and miR-141 (23 bp), respectively, immediately downstream of the Renilla luciferase gene.
Figure 6:
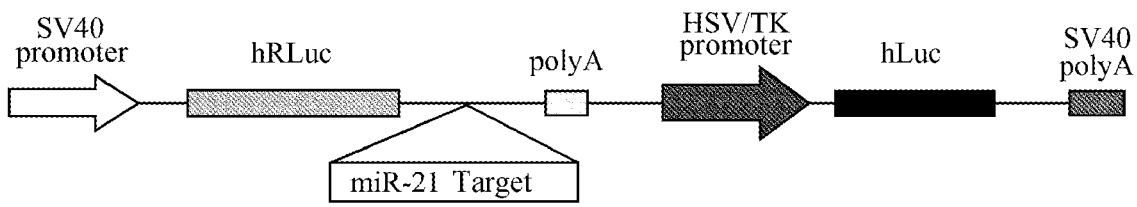
Figure 6:
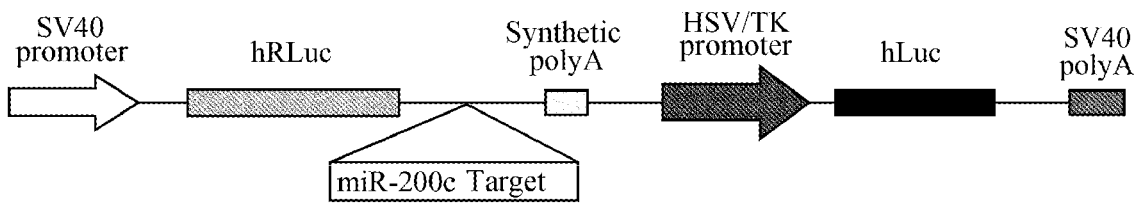
Figure 6:
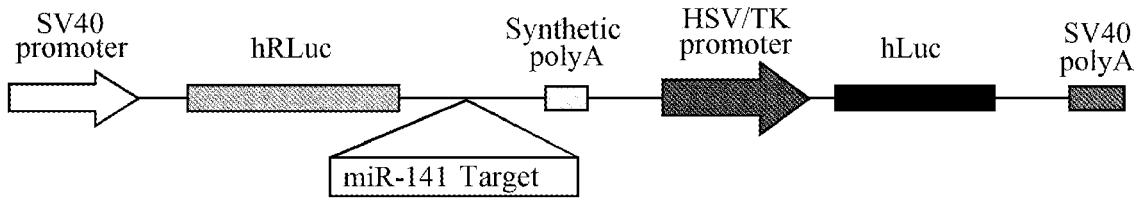

The sequences of base pairs forming the double-stranded structure can be designed appropriately so that the double strand can be formed specifically and stably in a miRNA inhibitor. For example, it is preferable to avoid a homopolymeric sequence with a long repetition of the same nucleotide (for example, eight or more nucleotides, preferably seven or more nucleotides, more preferably five or more nucleotides, even more preferably four or more nucleotides, and yet even more preferably three or more nucleotides). Furthermore, it is also preferable to avoid sequences in which sequences of several nucleotides are repeated in tandem, such as two-nucleotide repeat sequences or three to four nucleotide repeat sequences. The GC content of the double-stranded portion can be adjusted appropriately, and is for example, 12% to 85%, preferably 15% to 80%, 20% to 75%, 25% to 73%, 32% to 72%, 35% to 70%, 37% to 68%, or 40% to 65%. Other examples different from those shown above may include the sequences of stem I and stem II shown in FIG. 6A of WO2010/047216, but are not limited thereto.

MBSs and double-stranded structures may be linked directly, or they may be linked via other sequences. For example, an MBS can be linked to the end of a double-stranded structure via a suitable linker or a spacer sequence.

While significant inhibitory activity can be obtained by directly linking an MBS to the double-stranded portion, addition of a linker (or also referred to as a spacer) further increases the inhibitory effect on miRNA (Example 4 of WO2010/047216). The linker or spacer sequence between an MBS sequence and a double-stranded structure may increase the accessibility of the MBS to a miRNA present in RISC. The length of the linker or spacer may be adjusted appropriately, and examples include one to ten nucleotides, preferably one to nine nucleotides, one to eight nucleotides, one to seven nucleotides, one to six nucleotides, one to five nucleotides, one to four nucleotides, and one to three nucleotides. For example, when linking two or more MBSs, it is preferable to link them via a linker or spacer. There is no particular limitation on the sequence of the linker or spacer, and for example, it may be a sequence comprising A and/or C, or a sequence comprising more A and/or C than other nucleotides. Furthermore, it is preferable to pay attention not to make the linker or spacer sequences form stable base pairs with opposite linker or spacer sequences, or MBSs. Examples include AAC, CAA, ACC, CCA, and a sequence comprising any one of these. A pair of linker or spacer sequences that are added to both sides of an MBS may be inverted sequences (mirror-image sequences). For example, AAC may be added to the 5' side of an MBS and CAA may be added to the 3' side.

Furthermore, nucleic acids constituting miRNA inhibitors of the present invention may be modified. For example, nucleotides constituting a nucleic acid may be naturally-occurring nucleotides, modified nucleotides, artificial nucleotides, or combinations thereof. Furthermore, nucleic acids comprised in miRNA inhibitors of the present invention may comprise RNAs, or may be RNA/DNA chimeras. They may comprise other nucleic acid analogs, or any combination thereof. The nucleic acids include not only those linked by phosphodiester bonds, but also those having amide bonds or other backbones (peptide nucleic acids (PNAs) and such). The nucleic acid analogs include, for example, naturally-occurring and artificial nucleic acids, and they may be nucleic acid derivatives, nucleic acid analogs, nucleic acid relatives, and such. Such nucleic acid analogs are well known in the art, and examples include, but are not limited to, phosphorothioate, phosphoramidate, methylphosphonate, chiral methylphosphonate, 2'-O-methylribonucleotide, and peptide nucleic acid (PNA). The PNA backbones may include a backbone comprising aminoethylglycine, polyamide, polyethyl, polythioamide, polysulfinamide, polysulfonamide, or a combination thereof (Krutzfeldt, J. et al., Nucleic Acids Res. 35: 2885-2892; Davis, S. et al., 2006, Nucleic Acids Res. 34: 2294-2304; Boutla, A. et al., 2003), Nucleic Acids Res. 31: 4973-4980; Hutvagner, G. et al., 2004, PLoS Biol. 2: E98; Chan, J. A. et al., 2005, Cancer Res. 65: 6029-6033; Esau, C. et al., 2004, J. Biol. Chem. 279: 52361-52365; Esau, C. et al., 2006, Cell Metab. 3: 87-98).

Modification of nucleic acids may be carried out to inhibit degradation by endonucleases. Particularly preferred modifications include 2' or 3' glycosylation, for example, 2'-O-methyated (2'-O-Me) nucleotides, or 2'-deoxynucleotides, or 2'-fluoro, difluorotoluyl, 5-Me-2'-pyrimidine, 5-allylaminopyrimidine, 2'-O-methoxyethyl (2'-O-MOE), 2'-O-aminopropyl (2'-O-AP), 2'-O—N-methylacetamide (2'-O-NMA), 2'-O-dimethylaminoethyloxyethyl (2'-DMAEOE), 2'-O-dimethylaminoethyl (2'-DMAOE), 2'-O-dimethylaminopropyl (2'-O-AP), 2'-hydroxynucleotide, phosphorothioate, 4'-thionucleotide, 2'-O-trifluoromethylnucleotide, 2'-O-ethyl-trifluoromethoxynucleotide, 2'-O-difluoromethoxyethoxynucleotide, or 2'-ara-fluoro nucleotide, locked nucleic acid (LNA), ethylene nucleic acids such as 2'-O, 4'-C-ethylene bridged nucleic acid (ENA), other bridged nucleic acid (BNA), hexitol nucleic acid (HNA), morpholino nucleic acid, tricyclo-DNA (tcDNA), polyether nucleic acid (U.S. Pat. No. 5,908,845), cyclohexene nucleic acid (CeNA), and combinations thereof. Furthermore, difluorotoluyl (DFT) modifications such as 2,4-difluorotoluyl uracil, or substitution of guanidine with inosine may be carried out.

Furthermore, the nucleic acids may comprise a conjugate on the end. Examples of the conjugate include lipophilic substances, terpenes, protein-binding substances, vitamins, carbohydrates, retinoids, and peptides. Specific examples include C5-aminoalkyl dT, naproxen, nitroindol, folic acid, colonic acid, ibuprofen, retinoid, polyethyleneglycol (PEG), C5 pyrimidine linker, glyceride lipids (for example, dialkylglyceride derivative), vitamin E, cholesterol, thiocholesterol, dU-cholesterol, alkyl chains, aryl groups, heterocyclic complexes, and modified sugars (D-ribose, deoxyribose, glucose, and such). The conjugates and the nucleic acids can be linked, for example, via any linker, and specific examples include pyrrolidine linkers, serinol linkers, aminooxy or hydroxyprolinol linker, and such.

miRNA inhibitors can be designed to be composed of a linear single-stranded nucleic acid (FIG. 2 of WO2010/047216). In particular, a complex in which all MBSs are concentrated on one side (the right side in FIG. 2 of WO2010/047216) of a certain double-stranded structure (stem I of FIG. 2 of WO2010/047216), and strands of the double-stranded structure each has a closed structure on that side (that is, they are connected by a sequence containing an MBS), and the two ends of a single-stranded RNA are present on opposite sides of the double-stranded structure, is preferred (FIG. 2 of WO2010/047216). Additional double-stranded structures (stems II, III, and such of FIG. 2 of WO2010/047216) may be comprised in the MBS-containing sequences. The length of the single-stranded RNA can be determined appropriately, and is, for example, 500 nucleotides or less, preferably 450 nucleotides or less, 420 nucleotides or less, 400 nucleotides or less, 380 nucleotides or less, 360 nucleotides or less, 340 nucleotides or less, 320 nucleotides or less, 300 nucleotides or less, 280 nucleotides or less, 260 nucleotides or less, 240 nucleotides or less, 220 nucleotides or less, 200 nucleotides or less, 180 nucleotides or less, 160 nucleotides or less, 140 nucleotides or less, 120 nucleotides or less, 100 nucleotides or less, or 80 nucleotides or less. For example, the length of a single-stranded RNA forming a complex having two double-stranded structures and two MBSs is, for example, 60 to 300 nucleotides, preferably 70 to 250 nucleotides, 80 to 200 nucleotides, 90 to 180 nucleotides, or 100 to 150 nucleotides. The length of a first double-stranded structure (the double-stranded structure close to the two ends of a single-stranded RNA) may be, for example, 15 to 30 bp, preferably 16 to 28 bp, more preferably 17 to 25 bp, even more preferably 17 to 24 bp, such as 17 bp, 18 bp, 19 bp, 20 bp, 21 bp, 22 bp, 23 bp, or 24 bp. A second double-stranded structure (an additional double-stranded structure comprised in MBS-containing sequences) may be made shorter than the first double-stranded structure to make the whole molecule compact, and the length may be, for example, 4 bp to 20 bp, such as 5 bp to 15 bp, 5 bp to 12 bp, 5 bp to 10 bp, 6 bp to 9 bp, or 7 bp to 8 bp.

Furthermore, the present invention relates to RNAs constituting the miRNA inhibitors of the present invention (herein, RNAs include naturally-occurring RNAs and nucleic acid analogs), and nucleic acids that encode the RNAs (DNAs or RNAs). When a miRNA inhibitor is composed of a single continuous RNA strand, the miRNA inhibitor of the present invention can be constructed by intramolecular annealing of the RNA. Alternatively, when the miRNA inhibitor is composed of two or more RNA molecules, the miRNA inhibitor of the present invention can be constructed by annealing these RNAs. The RNAs can be synthesized appropriately. For example, a desired RNA can be produced by RNA chemical synthesis. Alternatively, an RNA can be expressed by an expression vector that expresses the RNA. There is no particular limitation on the expression vectors. For example, one can use desired expression vectors expressed in bacteria such as *Escherichia coli*, eukaryotic cells such as yeast, insect cells, plant cells, or animal cells. For example, one can think of inhibiting miRNA function using a vector for expression in cells of higher eukaryotes such as plants, insects, and animals, and expressing the RNA in these cells. There is no particular limitation on the promoters for transcribing RNAs. Pol I promoters, Pol II promoters, Pol III promoters, promoters of bacteriophages, and such may be used. When a bacteriophage transcriptase and a vector comprising its promoter are introduced simultaneously and then used, for example, an RNA polymerase and a promoter of T4 phage or T7 phage can be utilized. Furthermore, examples of the polymerase II (Pol II) promoters include the CMV promoter, the β-globin promoter, and such. In order to express a relatively short RNA of several hundred bases or less, it is preferable to use a polymerase III (Pol III) promoter expected to show a higher level of expression than Pol II. Examples of the Pol III promoters include the U6 promoter, H1 promoter, tRNA promoter, 7SK promoter, 7SL promoter, Y3 promoter, 5S rRNA promoter, Ad2 VAI, and VAII promoter (Das, G. et al., 1988, EMBO J. 7:503-512; Hernandez, N., 1992, pp. 281-313, In S. L. McKnight and K. R. Yamamoto (ed.), Transcriptional regulation, vol. 1. Cold Spring Harbor Laboratory, Cold Spring Harbor, N.Y.; Kunkel, G. R., 1991, Biochim. Biophys. Acta 1088:1-9; Lobo, S. M., and N. Hernandez, 1989, Cell 58:55-67; Mattaj, I. W. et al., 1988, Cell 55:435-442; Geiduschek, E. P. and G. A. Kassavetis, 1992, pp. 247-280, In Transcriptional regulation. Monograph 22 (ed. S. L. McKnight and K. R. Yamamoto), Cold Spring Harbor Laboratory Press, Cold Spring Harbor, N.Y.). In particular, Class 3 promoters found in various snRNA and cytoplasmic RNA genes can be exemplified, and examples include promoters of the U6, 7SK, hY1, hY3, H1, and MRP/ThRNA gene (Hernandez, N., 1992, pp. 281-313, In Transcriptional regulation. Monograph 22 (ed. S. McKnight and K. R. Yamamoto), Cold Spring Harbor Laboratory Press, Cold Spring Harbor, N.Y.). For example, human U6, human H1, mouse U6 promoters, and such can be favorably used. When using a Pol III promoter, for example, a poly (T) tract of about four to seven nucleotides can be added downstream of a DNA encoding the RNA to be transcribed to function as a transcription terminator.

Furthermore, expression can be induced by using an inducible promoter. Inducible promoters include, for example, tetracycline-inducible promoters, but are not limited thereto. Tetracycline operator sequences (TetO sequences) in tetracycline-inducible promoters include, for example, the sequence of positions 128 to 146 of SEQ ID NO: 10, but are not limited thereto.

A TetO sequence can be appropriately placed in a promoter, and a single copy or multiple copies of the sequence may be placed. When multiple copies are placed, they may be arranged in tandem at one site or dispersedly at multiple sites. For example, when a TetO sequence is placed in a PolIII promoter, the sequence (one to three copies, preferably two copies) is preferably placed between the proximal sequence element (PSE) and the octamer motif just prior thereto (on the 5' side). More preferably, a TetO sequence (one or two copies, preferably one copy) is placed just after the TATA box (on the 3' side). PolIII promoters in which two copies of TetO sequence are placed between PSE and the octamer motif just prior thereto (on the 5' side) and one copy of TetO sequence is placed just after the TATA box (on the 3' side) are tetracycline-inducible promoters with remarkably excellent tetracycline responsiveness. Furthermore, the tetracycline-inducible promoters include those which contain additional TetO sequences, for example, those which contain one to five copies, preferably one to three copies of TetO sequence in a region around another octamer motif upstream of the octamer motif just prior to (on the 5' side of) PSE. It is possible to use a desired PolIII promoter, and a suitable PolIII promoter is, for example, human 7SK RNA promoter. The 7SK RNA promoter may be a naturally-derived promoter (SEQ ID NO: 74) or a modified one (e7SK; SEQ ID NO: 75). Preferred examples include, but are not limited to, for example, those which comprise SEQ ID NO: 76 (Tet-e7SK6) or SEQ ID NO: 77 (Tet-e7SK10).

Transcription units thus constructed can be used for expression as they are, or they can be used after integration into another vector system. There is no particular limitation on the vector, and expression plasmids and desired viral vectors and such can be used. Examples of viral vectors include, but are not limited to, retroviral vectors, adenovirus vectors, adeno-associated virus vectors, and such (Miller, A. D. et al. (1991) J. Virol. 65, 2220-2224; Miyake, S. et al. (1994) Proc. Natl. Acad. Sci. USA, 91, 8802-8806; Samulski, R. J. et al. (1989) J. Virol. 63, 3822-3828). For example, a transcription unit comprising a Pol III promoter can be integrated into the LTR of a retrovirus (including a lentivirus), and then used. By integration into a retroviral vector, genes can be transfected into target cells with high efficiency. In addition, since transgenes are incorporated into the chromosome, miRNAs can be stably inhibited for a long time. There is no particular limitation on the retroviruses used, and they include, for example, ecotropic viral vectors (Kitamura, T. et al. (1995) Proc. Natl. Acad. Sci. USA. 92, 9146-9150), amphotropic viral vectors, viral vectors pseudotyped with VSV-G and such (Arai, T. et al. (1998) J. Virol. 72, 1115-1121), lentiviral vectors such as HIV vectors, SIV vectors, and FIV vectors (Shimada, T. et al. (1991) J. Clin. Inv. 88, 1043-1047). For example, MoMLV-based retroviral vectors or HIV-based lentiviral vectors can be used. When integrating a transcription unit into an LTR, for example, it can be integrated into the ΔU3 region of an LTR having a deletion at the U3 region (ΔU3) (FIG. 2). In a preferred embodiment, the vectors can express miRNA-inhibiting RNAs and inhibit miRNA function for one week or more, preferably two weeks or more, three weeks or more, four weeks or more, or one month or more after introduction into cells.

The present invention also relates to nucleic acids (for example, DNAs) for producing nucleic acids encoding RNAs that constitute miRNA inhibitors of the present invention, which at least encode a miRNA-binding sequence to at least one miRNA containing 5'-AACACUG-3' as a seed sequence and a miRNA-binding sequence to at least one miRNA containing 5'-AAUACUG-3' as a seed sequence, and/or complementary strands thereof. The nucleic acids preferably contain, for example, 5'-CAGUGUU-3' and 5'-CAGUAUU-3', specifically, contain at least two miRNA-binding sequences: a miRNA-binding sequence containing 5'-CAGUGUU-3' and a miRNA-binding sequence containing 5'-CAGUAUU-3'. The present invention also relates to compositions for producing nucleic acids (for example, DNAs) encoding RNAs that constitute miRNA inhibitors of the present invention, which contain nucleic acids at least encoding a miRNA-binding sequence to at least one miRNA containing 5'-AACACUG-3' as a seed sequence and a miRNA-binding sequence to at least one miRNA containing 5'-AAUACUG-3' as a seed sequence, and/or complementary strands thereof.

The miRNA inhibitors of the present invention or RNAs constituting the inhibitors (herein, the RNAs include naturally-occurring RNAs and analogs), or vectors expressing the RNAs can be made into compositions for inhibiting miRNAs. Since compositions of the present invention can specifically and efficiently inhibit target miRNAs, they are useful for functional regulation of genes by inhibiting miRNAs. The compositions of the present invention can be combined with a desired pharmaceutically acceptable carrier or medium as necessary. Desired pharmaceutically acceptable carriers include desired solutions conventionally used for suspending nucleic acids, such as distilled water, phosphate-buffered saline solution (PBS), sodium chloride solution, Ringer's solution, and culture solution. Furthermore, plant oils, suspending agents, surfactants, stabilizers, biocides, and such may be included. Preservatives or other additives may also be added. Furthermore, the compositions of the present invention can be combined with carriers including organic substances such as biopolymers, inorganic substances such as hydroxyapatite, specifically, collagen matrix, polylactic acid polymer or copolymer, polyethylene glycol polymer or copolymer, chemical derivatives thereof, etc. The compositions of the present invention can be used as desired reagents or pharmaceutical compositions. Furthermore, the present invention provides use of the compositions of the present invention, miRNA inhibitors of the present invention, or RNAs constituting the inhibitors or vectors that express the RNAs, for inhibiting miRNAs. The present invention also provides miRNA inhibitors comprising any one of the above. Moreover, the present invention also provides use of the compositions of the present invention, miRNA inhibitors of the present invention, or RNAs constituting the inhibitors or vectors that express the RNAs, for suppressing tumor. The present invention also provides tumor-suppressing agents comprising any one of the above.

Introduction of an inhibitor into cells can be carried out in vitro, ex vivo, or in vivo. The route of administration can be appropriately selected so that a sufficient amount of the inhibitor can reach tumor. Preferably, the inhibitor is administered directly to tumor. As necessary, the inhibitor can be combined with a suitable DDS and introduced via intratumoral injection, intravenous injection, or such. When administered via cells, introduction into suitable culture cells, cells collected from the animal to be inoculated, or such, is carried out. Methods for introducing nucleic acids include the calcium phosphate coprecipitation method, lipofection, DEAE dextran method, method of directly injecting a DNA solution into a tissue using an injection needle or such, and introduction using a gene gun. Viral vectors and such may also be used for administration. The dosage differs depending on the disease, body weight, age, gender, and symptoms of the patient, purpose of administration, form of administered composition, administration method, transgene, and such. However, the dosage may be adjusted appropriately depending on the animal to be administered, site of administration, number of doses, and such, and those skilled in the art can determine it appropriately. The route of administration can be suitably selected. Preferably, the targets of administration are mammals including human and nonhuman mammals. Specific examples include humans, non-human primates such as monkeys, rodents such as mice and rats, rabbits, goats, sheep, pigs, bovine, dogs, cats, and other mammals.

EXAMPLES

Herein below, the present invention will be specifically described with reference to the Examples, but it is not to be construed as being limited thereto. All references cited herein are incorporated into this description.

[Example 1] Induction of Epithelial-Mesenchymal Transition by Functional Inhibition of the miR-200 Family <Materials and Methods>
Cell Culture Cells of human colon adenocarcinoma cell line HCT116 (obtained from ATCC) were cultured at 37° C. in DMEM supplemented with 10% fetal bovine serum (FBS). In tetracycline-induction experiments, cells were cultured at 37° C. in DMEM supplemented with 10% FBS compatible for the Tet system (Tet-approved FBS (Clontech)) in the presence or absence of Dox (Doxycycline (Sigma)).

Plasmid Construction

To construct H1 promoter type-, e7SK (enhanced 7SK) promoter type-, and Tete7SK (Tetracycline-responsive e7SK) promoter type-TuD shuttle vectors, the DNA fragments listed in Table 1 were synthesized by Genscript (NJ, USA). These PolIII-TuD shuttle fragments were digested with BamHI and EcoRI, and cloned into BamHI-EcoRI site of pCR2.1 to prepare pH1-TuD-shuttle, pe7SK-TuD-shuttle, and pTete7SK-TuD-shuttle vectors. Two other PolIII-TuD-shuttle vectors, pmU6-TuD-shuttle and ph7SK-TuD-shuttle, have already been described (Nucleic Acids Res. 37: e43, 2009; Nucleic Acids Res. 40: e58, 2012).

TABLE 1

| Primer | Sequence |
| --- | --- |
| BamHI-<br>H1-TuD-<br>shuttle-<br>EcoRI | 5'-GGATCCGAACGCTGACGTCATCAACCCGCTCCAAGGAATCGCGGGCCCAGTGTCACTAGGCGGGAACACCCAGC<br>GCGCGTGCGCCCTGGCAGGAAGATGGCTGTGAGGGACAGGGGAGTGGCGCCCTGCAATATTTGCATGTCGCTAT<br>GTGTTCTGGGAAATCACCATAAACGTGAAATGTCTTTGGATTTGGGAATCTTATAAGTTCTGTATGAGACCACAGG<br>ATGTGAGGGCGTCATCGGAGACGACACCATCCACAGCCAGCGTCTCGATGACGCCCTCACATCCTTTTTTGAA-3' |
| BamHI-<br>e7SK-<br>TuD-<br>shuttle-<br>EcoRI | 5'-GGATCCTGCAGTATTTGCATATGCAAATAAGGTGGTGGATCGATTCTGGATAGTGTCAAAACAGCCGGAAATCAA<br>GTCCGTTTATCTCAAACATTTGCATTTTGGGAATAAATGATATTTGCATTGCTGGTTAAATTAGATTTTAGTTAAATTT<br>CCTGCTGAAGCTCTAGTACGATAAGCAACTTGACCTAAGTGTAAAGTTGAGATTTCCTTCAGGTTTATATAGCTTGT<br>GCGCCGCCTGGGTACCTCGGATGTGAGGGCGTCATCGGAGACGACACCATCCACAGCCAGCGTCTCGATGACGCC<br>CTCACATCCTTTTTTGAATTC-3' |

TABLE 1-continued

| Primer | Sequence |
|---|---|
| BamHI- | 5'-GGATCCTGCAGTATTTGCATATGCAAATAAGGTGGTGGATCGATTCTGGATAGTGTCAAAACAGCCGGAAATCAA |
| Tete7SK- | GTCCGTTTATCTCAAACATTTGCATITTGGGAATAAATGATATTTGCATTGCTCCCTATCAGTGATAGAGATTAAATT |
| TuD- | TCCTTCCCTATCAGTGATAGAGAAAGCAACTTGACCTAAGTGTAAAGTTGAGATTTCCTTCAGGTTTATATAGCTCC |
| shuttle- | CTATCAGTGATAGAGACTCGGATGTGAGGGCGTCATCGGAGACGACACCATCCACAGCCAGCGTCTCGATGACG |
| EcoRI | CCCTCACATCCTTTTTTGAATTC-3' |

(SEQ IN NOs: 8 TO 10 from the top)

To construct lentivirus, pLenti6/V5-GW/lacZ (Life Technologies) was digested with AgeI, followed by the treatment with Klenow fragment, and then was digested with KpnI. pLSP (Nucleic Acids Res. 37: e43, 2009) was digested with ClaI, followed by the treatment with Klenow fragment, and then was digested with KpnI. These 0.9-kb and 5.1-kb fragments were ligated by a ligase to generate pLSB. To construct Tet-inducible TuD RNA expression lentiviral vectors, BamHI-EcoRI fragments of pTete7SK-TuD-200c, pTete7SK-TuD-141/200c, and pTete7SK-TuD-NC were subcloned into the lentiviral vector pLSB to prepare pLSB-Tete7SK-TuD-200c, pLSB-Tete7SK-TuD-141/200c, and pLSB-Tete7SK-TuD-NC, respectively. To construct luciferase reporter plasmids, the pairs of oligonucleotides listed in Table 2 were allowed to anneal with each other and cloned into XhoI-NotI site of psiCHECK2 (Promega) to prepare psiCHECK2-T21, psiCHECK2-T200c, and psiCHECK2-T141, respectively.

TABLE 2

| Primer | | Sequence |
|---|---|---|
| psiCHECK2-T21 | s+ | 5'-TCGAGTCAACATCAGTCTGATAAGCTAGC-3' |
| psiCHECK2-T21 | a+ | 5'-GGCCGCTAGCTTATCAGACTGATGTTGAC-3' |
| psiCHECK2-T200c | s | 5'-TCGAGTCCATCATTACCCGGCAGTATTAGC-3' |
| psiCHECK2-T200c | a | 5'-GGCCGCTAATACTGCCGGGTAATGATGGAC-3' |
| psiCHECK2-T141 | s | 5'-TCGAGCCATCTTTACCAGACAGTGTTAGC-3' |
| psiCHECK2-T141 | a | 5'-GGCCGCTAACACTGTCTGGTAAAGATGGC-3' | s+; Sense strand
a+; Antisense strand
(SEQ ID NOs: 11 to 16 from the top)

Establishment of Tetracycline-Inducible Cell Lines

HCT116 cells were seeded at 1×10⁵ cells/well in a 6-well plate and introduced with pXL001 (for PolIII system; Addgene plasmid 26122) virus stock (<1×10⁴ TU) in the presence of 8 µg/ml Polybrene. Puromycin (1 µg/ml) selection was started 24 hours after introduction. After 10 days of selection, puromycin was removed from the culture medium. Some stable clones were isolated by FACS sorting using FACS Aria (BD), and a clone selected therefrom was named HCT116-TetONIII. The HCT116-TetOnIII cells were seeded at 1×10⁵ cells/well in a 6-well plate in DMEM supplemented with 10% FBS. 24 hours later, a virus stock (3×10⁵ TU) of pLSB-Tete7SK-TuD-141/200c or pLSB-Tete7SK-TuD-NC was introduced into the cells in the presence of 8 µg/ml Polybrene to prepare HCT116-TetOn-TuD-141/200c cells and HCT116-TetOn-TuD-NC cells, respectively. Another 24 hours later, the culture media were replaced with DMEM supplemented with 10% FBS and blasticidin (10 µg/ml). Following seven days of selection, blasticidin was removed from the culture media.

Transfection and Luciferase Assay

On the day before transfection, cells were seeded at a density of 1×10⁵ cells/well in a 24-well plate in DMEM supplemented with 10% FBS. HCT116-TetOnIII cells were transfected in triplicate with PEI-MAX (Polysciences Inc.), 200 ng of dual luciferase target reporter plasmid (FIG. 6) and 10 ng to 300 ng of TuD RNA expression plasmid. HCT-116-Tet-On-TuD141/200c cells and HCT-116-Tet-On-TuDNC cells were transfected in triplicate with PEI-MAX and 200 ng of dual luciferase target reporter plasmid. All assays were performed using Dual-Luciferase Assay (Promega, Madison, Wis.) with Glomax (Promega) 48 hours after transfection.

[Example 1-1] PolIII-Driven TuD Expression Vector

Figure 7:
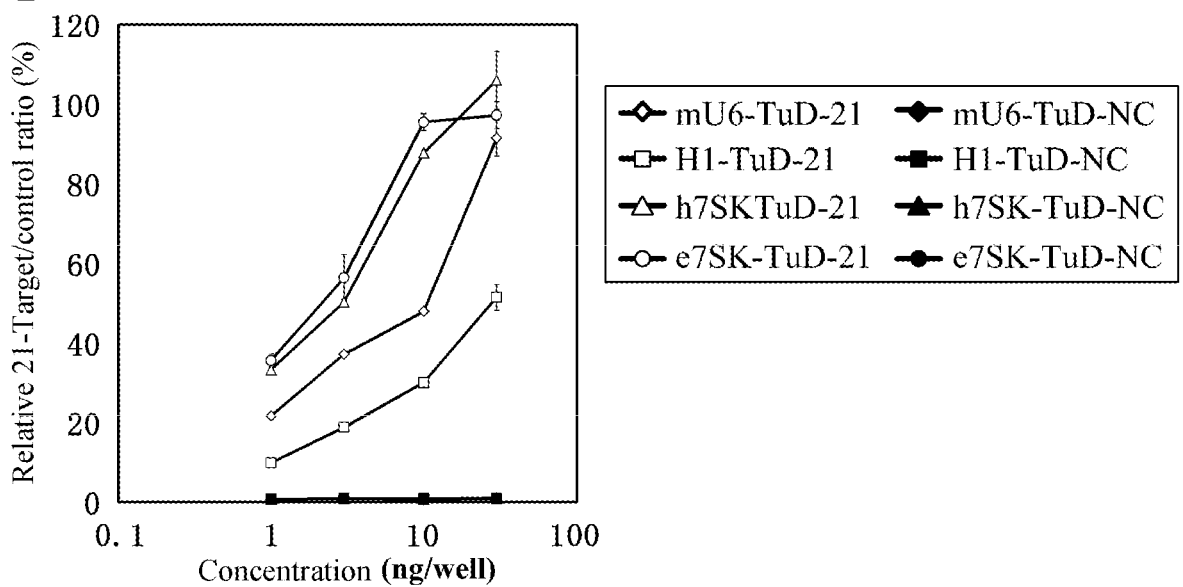
FIG. 7. A comparison of polIII promoters in terms of TuD RNA expression. (A) The sequences of h7SK and e7SK promoters. The positions of the TATA box, octamer motif, PSE, and CACCC box are shown. Modified sequences in the e7SK promoter are shown by bold letters. Two arrows in the e7SK promoter represent inverted repeats of the octamer motif generated by modification. (B) The miRNA-inhibitory activity of TuD RNA expression vectors that are driven by the polIII promoters. HCT116 cells were transfected with luciferase reporter vectors and TuD RNA expression vectors at several doses. Dual luciferase assay was performed 48 hours after transfection. The expression ratio of miR-21-RL/FL to UT-RL/FL was represented as mean±SD (n=3).

PolIII-driven promoters tested were: mouse U6 promoter, human HI promoter, and human 7SK promoter and modified form thereof (e7SK) (FIG. 7A). Among these promoters, e7SK promoter located upstream of the sequence that produces TuD-21 showed the greatest miRNA inhibitory activity. When the same reporter system described above was used, the RNA interference induced by endogenous miR-21 was cancelled almost completely (FIG. 7B). Then, the present inventors used e7SK promoter as a parent vector that serves as a basis for the construction of controllable vectors. Furthermore, the expression of interferon-responsive genes such as OAS1, OAS2, MX1, IRF9, and IFITM1 was not detected when PolIII or these TuD expression plasmids having PolIII promoters were transfected. Therefore, it was shown that, similarly as reported by the transfection of S-TuD (synthetic TuD) RNA, none of these TuD transcripts induces unintended immunostimulation.

[Example 1-2] Development of Tetracycline-Inducible TuD RNA Expression System

Figure 8:
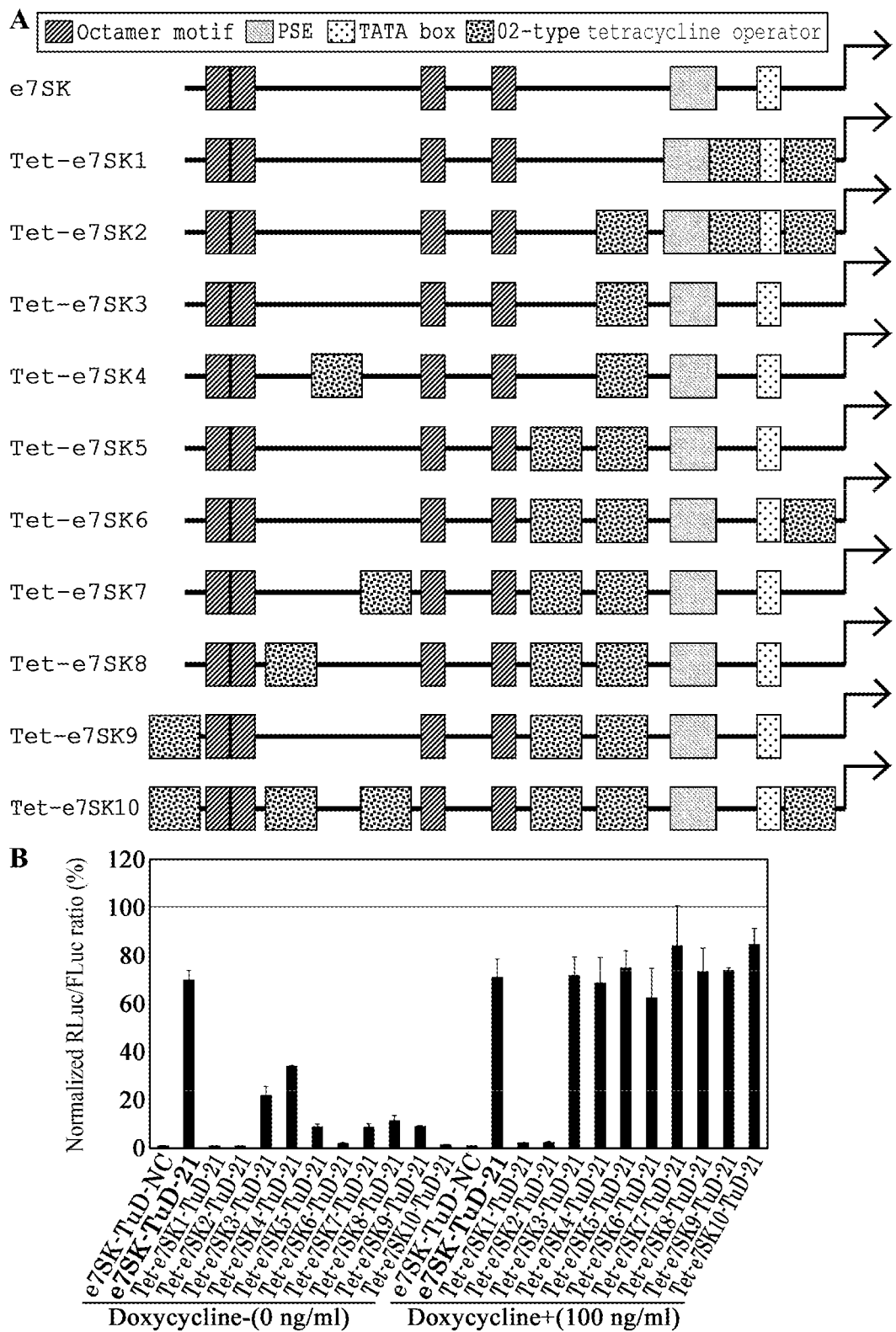
FIG. 8. Tet-inducible polIII promoters that were constructed and tested in the present experiments. (A) Schematic diagram of the parent e7SK promoter and derivatives thereof which have a O2-type tetracycline operator as an insert. Arrows indicate the transcription start site. (B) HCT116-TetOn III cells were transfected with luciferase reporters and each TuD RNA expression vector driven by the promoter shown in (A), and allowed to proliferate in the presence or absence of Doxycycline. Dual luciferase assay was performed 48 hours after transfection. The expression level ratio of miR-21-RL/FL to UT-RL/FL was represented as mean±SD (n=3).

To develop a Tet-inducible PolIII promoter-driven TuD RNA expression system, 10 types of e7SK promoter derivatives (#1 to #10) comprising a tetracycline-responsive sequence were constructed and the optimal number and location of the sequence were screened (FIG. 8A). Furthermore, cells introduced with tTR-KRAB expression lentiviral vector (pXL001) were cloned and named HCT116-TetOnIII. When TuD-21 expression plasmids carrying each of the 10 types of promoters were transfected, Tet #6 promoter (SEQ ID NO: 76) and Tet #10 promoter (SEQ ID NO: 77) did not inhibit miR-21 under the condition of Dox-, while in the presence of Dox, the promoters retained a full inhibiting effect (FIG. 8B). The #6 promoter was named Tete7SK promoter and used in subsequent analyses.

Tete7SK promoter was located upstream of the DNA sequence that produces TuD-200c, and was inserted into a lentiviral vector (FIG. 2A). The vector was introduced into HCT116-TetOnIII cells. When evaluating with reporter assay, miRNA-inhibiting effect was not observed in the absence of Dox. Meanwhile, when Dox was used at a concentration of 10 nM to 1 µM, endogenous miR-200c activity was observed to be suppressed almost completely (FIG. 2B). Since no cytopathic or cytostatic effect was observed in this Dox range, the system was considered to be applicable for the analysis of all-or-none switching of endogenous miRNA. Thus, 0.1 µM Dox was used to induce TuD expression in subsequent analyses.

[Example 1-3] Induction of EMT and MET by Regulatory Inhibition of the miR-200 Family Activity The members of the miR-200 family are a key regulator of EMT. miRNA microarray analysis of the cell line HCT116 has shown that two miR-200 gene loci are transcribed at a basal level whereas the production of miR-200c/-141 (transcribed from chromosome 12) is extremely greater than that of the other miR-200 members (transcribed from chromosome 1). Recently, it has been reported that miR-200a and miR-200b have distinct target specificity due to a single nucleotide difference in their core sequences (2 to 8 bp from the 5' end) and nevertheless they share a considerable number of target genes. Taking into account that the core sequence of miR-200c is in common with those of miR-200b and miR-429 and that the core sequence of miR-200a is identical to that of miR-141 (FIG. 3-1A) and in order to efficiently inhibit all members of the miR-200 family, a hybrid type TuD in which two microRNA-binding sites are each complementary to miR-200c and miR-141 was designed (FIG. 3-1A). This is because each MBS in the TuD molecule can efficiently inhibit miRNAs having the same core sequence as that of target miRNA.

Lentiviral expression vector Tete7SK-TuD-141/200c was introduced into HCT116-TetOnIII cells, followed by drug selection, and the cells were named HCT116-TetOn-TuD-141/200c. The cell culture was carried out by allowing the cells to proliferate further in the absence of Dox (Dox−), or by adding Dox on day 0 (Dox+). On day 18, Dox was removed from a half of the Dox+ culture (Dox+/−) while the other half was allowed to further proliferate in the presence of Dox (Dox+).

Figure 9:
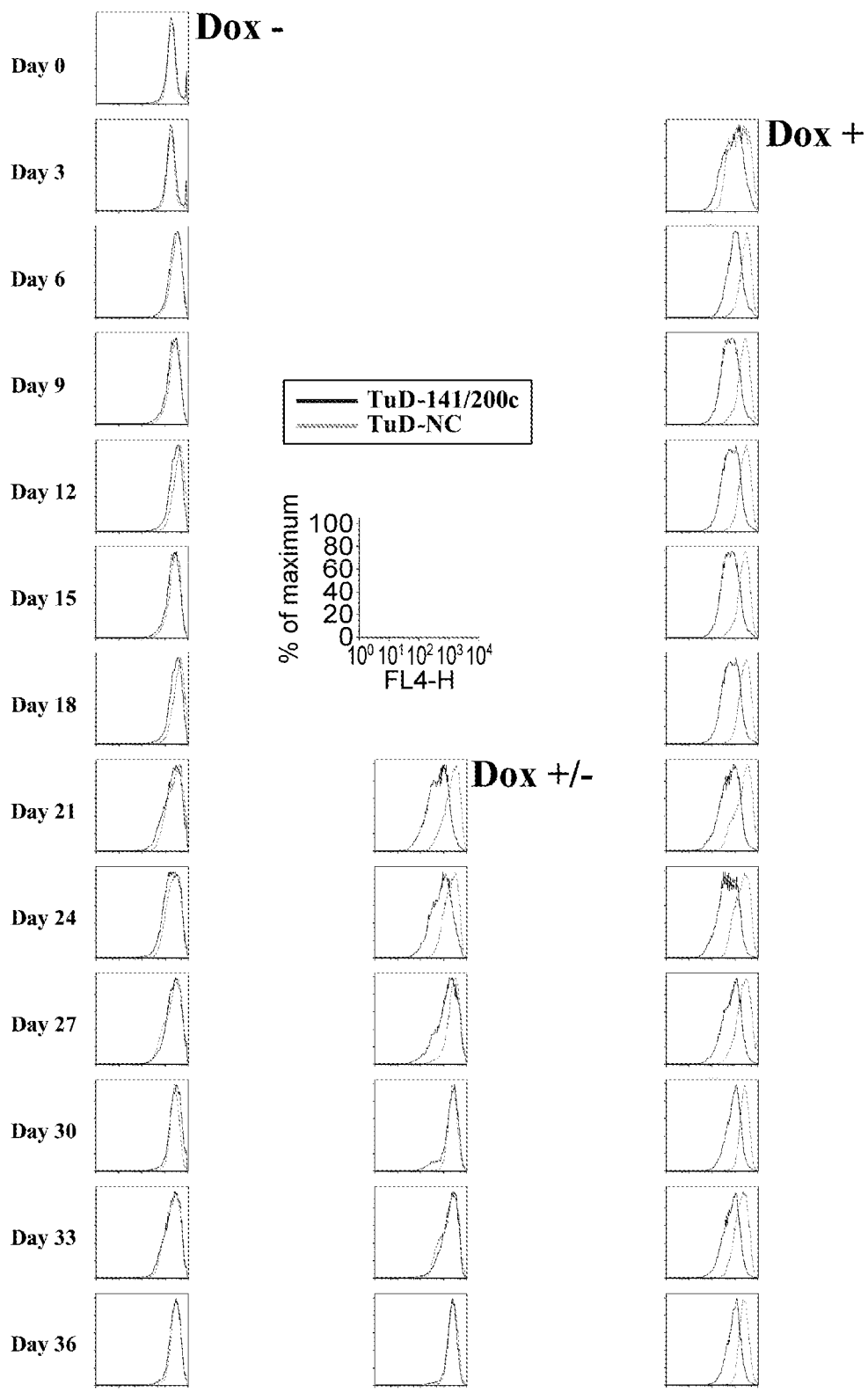
FIG. 9. FACS analysis of ESA expression profiles in the HCT116-TetOn-TuD-141/200c cells and HCT116-TetOn-TuD-NC cells. Dox−, Dox+, and Dox+/− cultures were prepared in accordance with the description of FIG. 3-1B. Black and gray lines represent the ESA expression profiles of the HCT-116-TetOn-TuD-141/200c cells and HCT-116-TetOn-TuD-NC cells, respectively.

Every three days in the course of culture, ESA expression profile of the cells was assessed by FACS (FIGS. 3-1B and 9) and their cellular morphology was observed (FIG. 3-2C). The Dox+ cells began to lose their cuboidal structure and showed an elongated mesenchymal-like morphology around day 6. The total peak of the ESA expression profile in Dox+ was shifted to a peak of about ¼ of that observed in Dox− on day 9. This shows that EMT occurred over the whole population of the culture. In the Dox+/− cells, their morphology and the level of ESA expression detected by FACS fully returned to the Dox− state by day 30 (12 days after Dox removal).

Figure 4:
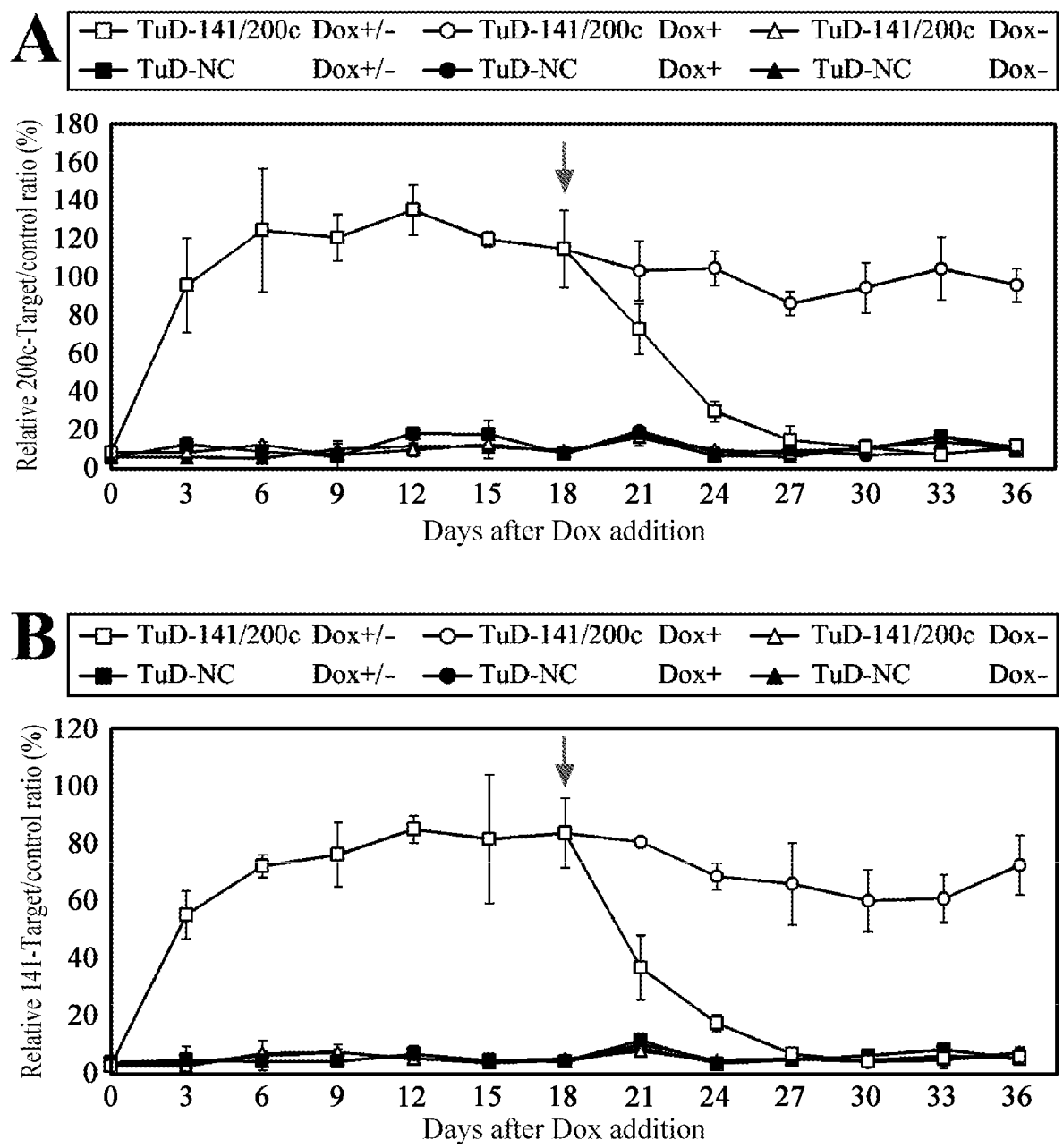
FIG. 4. Time-course analysis of the activities of endogenous miR-200c (A) and miR-141 (B). The parallel cultures used in FIG. 3-1B were transfected with dual luciferase reporters 48 hours before the indicated time points. The expression ratio of miR-200c-RL/FL to UT-RL/FL, and the expression ratio of miR-141-RL/FL to UT-RL/FL were represented as mean±SD (n=3). The arrow indicates the time point when Dox was removed.

The activity of both miR-200c and miR-141 was determined by measuring the luciferase activity of reporter plasmids transfected two days before the indicated time point (FIGS. 4A and B, respectively). On day 6, the reporter activity for either miR-200c or miR-141 in the Dox+ cells reached a level similar to that which does not have a target sequence (untargeted, UT), showing that the RNA interference by either miR-200c or miR-141 was almost fully suppressed. In contrast, the activities of miR-200c and miR-141 almost recovered to the original levels by day 27 (9 days after Dox removal). The in vivo half-life of TuD-141/200c was roughly estimated to be about 2.2 days based on the reduction in kinetics of the reporter activity after DOX removal.

Lentiviral expression vector Tete7SK-TuD-200c was introduced into HCT116-TetOnIII cells, followed by drug selection, and the cells were named HCT116-TetOn-TuD-200c. The cells were cultured under Dox+ for 30 or more days. The activity of both miR-200c and miR-141 was determined by measuring luciferase activity two days after the transfection of reporter plasmids (FIG. 5). The reporter activity for miR-200c reached a level similar to that which does not have a target sequence, demonstrating that the RNA interference by miR-200c was almost fully suppressed.

On the other hand, the reporter activity for miR-141 remained low as compared to that which does not have a target sequence, showing that the RNA interference by miR-141 was hardly suppressed. The findings described above demonstrate that TuD-200c suppresses the activity of miR-200c as compared to TuD-141/200c, but it does not suppress miR-141 which is in another family whose seed sequence is different at a single nucleotide.

[Example 2] Suppression of Breast Tumor by Functional Inhibition of the miR-200 Family <Materials and Methods>
Cell Culture Triple negative-breast cancer cell line SUM149PT (also referred to as SUM149) was obtained from Asterand, and cultured at 37° C. in Ham's F-12 medium supplemented with 5% fetal bovine serum (FBS), 10 mM HEPES, 5 µg/ml Insulin, 1 µg/ml Hydrocortisone, and 5 µg/ml Gentamicin (SUM149PT medium). In tetracycline induction experiments, cells were cultured at 37° C. in the presence or absence of 1 µg/ml Doxycycline (Sigma-Aldrich) in Ham's F-12 medium supplemented with 5% Tet-approved FBS (Clontech), 10 mM HEPES, 5 µg/ml Insulin, 1 µg/ml Hydrocortisone, and 5 µg/ml Gentamicin.

Antibody Staining and FACS Analysis

SUM149PT cells were stained with αESA-APC (324208, BioLegend), αCD24-PE (311106, BioLegend), αCD44-FITC (338804, BioLegend), αESA-PE (324206, BioLegend), and αCD49f-FITC (313606, BioLegend), and analyzed by FACS Calibur (BD).

RNA Preparation and miArray for miRNA

Total RNA was prepared from SUM149PT cells using miRVana (Life Technologies). The RNA samples were analyzed by 3D-Gene miArray for human miRNA in Toray Industries Inc.

Plasmid Construction

To construct lentiviral vector plasmids, pLSP (Haraguchi T. et al., Nucleic Acids Res. 2009; 37(6): e43) was digested with ClaI, followed by the treatment with Klenow fragment, and then was digested with KpnI. Furthermore, pLenti6/V5-GW/lacZ (Life Technologies) was digested with AgeI, followed by the treatment with Klenow fragment, and then was digested with KpnI. These 5.1-kb and 0.9-kb fragments were ligated to give pLSB.

To construct PolIII promoter-driven TuD RNA expression plasmids, a series of oligonucleotide pairs (Table 3) was allowed to anneal and cloned into PolIII-type-TuD-shuttle vectors (ph7SK-TuD-shuttle (Haraguchi T. et al., Nucleic Acids Res. 2012; 40(8): e58) and pTete7SK-TuD-shuttle) digested with BsmBI to prepare PolIII-driven TuD RNA expression cassettes. These cassettes were subcloned into BamHI-EcoRI site of pLSP or pLSB to give PolIII-driven TuD RNA expression lentiviral vector plasmids.

TABLE 3

| Primer | | Sequence |
|---|---|---|
| TuD-141 | s+ | 5'-CATCAACCCATCTTTACCACATAGACAGTGTTACAAGTATTCTGGTCACAGAATACAACCCATCTTTACCACATAGACAGTGTTACAAG-3' |
| TuD-141 | a+ | 5'-TCATCTTGTAACACTGTCTATGTGGTAAAGATGGGTTGTATTCTGTGACCAGAATACTTGTAACACTGTCTATGTGGTAAAGATGGGTT-3' |
| TuD-200c | s | 5'-CATCAACTCCATCATTACCCCACTGGCAGTATTACAAGTATTCTGGTCACAGAATACAACTCCATCATTACCCCACTGGCAGTATTACAAG-3' |
| TuD-200c | a | 5'-TCATCTTGTAATACTGCCAGTGGGGTAATGATGGAGTTGTATTCTGTGACCAGAATACTTGTAATACTGCCAGTGGGGTAATGATGGAGTT-3' |
| TuD-205 | s | 5'-CATCAACCAGACTCCGGTGAAGAGAATGAAGGACAAGTATTCTGGTCACAGAATACAACCAGACTCCGGTGAAGAGAATGAAGGACAAG-3' |
| TuD-205 | a | 5'-TCATCTTGTCCTTCATTCTCTTCACCGGAGTCTGGTTGTATTCTGTGACCAGAATACTTGTCCTTCATTCTCTTCACCGGAGTCTGGTT-3' |
| TuD-141/200c | s | 5'-CATCAACCCATCTTTACCACATAGACAGTGTTACAAGTATTCTGGTCACAGAATACAACTCCATCATTACCCCACTGGCAGTATTACAAG-3' |
| TuD-141/200c | a | 5'-TCATCTTGTAATACTGCCAGTGGGGTAATGATGGAGTTGTATTCTGTGACCAGAATACTTGTAACACTGTCTATGTGGTAAAGATGGGTT-3' | s+; Sense strand
a+; Antisense strand
(SEQ ID NOs: 17 to 24 from the top)

To construct miR-200c expression cassette, an oligonucleotide pair (Table 4) was subjected to PCR without template and the product was subcloned into pCR2.1 (Life Technologies). The BbsI-EcoRI fragment from the plasmid was subcloned into BbsI-EcoRI site of pmU6 (Proc. Natl Acad. Sci. USA, 99, 6047-6052) to give mU6-driven miR-200c expression cassette. To construct mU6-driven miR-141 and miR-205 expression cassettes, the DNA fragments listed in Table 5 were synthesized by Genscript. These cassettes were subcloned into BamHI-EcoRI site of pLSP to give mU6-driven miRNA expression lentiviral vector plasmids: pLSP-miR141, pLSP-miR200c, and pLSP-miR205. This pLSP-miR141 was digested with EcoRI, followed by the treatment with Klenow fragment, and then was digested with NheI. pLSP-miR200c was digested with BamHI, followed by the treatment with Klenow fragment, and then was digested with NheI. These 0.4-kb and 6.5-kb fragments were ligated to give pLSP-miR141+miR200c.

TABLE 4

| Primer | Sequence |
|---|---|
| miR-200cF+ | 5'-GAAGACTGTTTGATCCTGGGCCTGAAGCTGCCTGACCCAAGGTGGGCGGGCTGGGCGGGGCCCTCGTCTTACCCAGCAGTGTTTGGGTGCGGTTGGGAGTCTCT-3' |
| miR-200cR+ | 5'-GAATTCTAAGGGCTGGGGACCTGAGGCGATGGATGTTGCTGACACAGGGACAGGGGCCTCCATCATTACCCGGCAGTATTAGAGACTCCCAACCGCACCCA-3' |

F+; Forward primer
R+; Reverse primer
(SEQ ID NOs: 25 and 26, respectively)

TABLE 5

| Primer | Sequence |
|---|---|
| BamHI-mU6-pri-miR141-EcoRI | 5'-GGATCCGACGCCGCCATCTCTAGGCCCGCGCCGGCCCCCTCGCACAGACTTGTGGGAGAAGCTCGGCTACTCCCCTGCCCCGGTTAATTTGCATATAATATTTCCTAGTAACTATAGAGGCTTAATGTGCGATAAAAGACAGATAATCTGTTCTTTTTAATACTAGCTACATTTTACATGATAGGCTTGGATTTCTATAAGAGATACAAATACTAAATTATTATTTTAAAAACAGCACAAAAGGAAACTCACCCTAACTGTAAAGTAATTGTGTGTTTTGAGACTATAAATATCCCTTGGAGAAAAGCCTTGTTTGTAGCAACTGGTGAGCGCGCACCGTAGTTCTCTGTCGGCCGGCCCTGGGTCCATCTTCCAGTACAGTGTTGGATGGTCTAATTGTGAAGCTCCTAACACTGTCTGGTAAAGATGGCTCCCGGGTGGGTTCTCTCGGCAGTAACCTTCAGGGAGCCCTGAAGACCAGAATTC-3' |
| BamHI-mU6-pri-miR205-EcoRI | 5'-GGATCCGACGCCGCCATCTCTAGGCCCGCGCCGGCCCCCTCGCACAGACTTGTGGGAGAAGCTCGGCTACTCCCCTGCCCCGGTTAATTTGCATATAATATTTCCTAGTAACTATAGAGGCTTAATGTGCGATAAAAGACAGATAATCTGTTCTTTTTAATACTAGCTACATTTTACATGATAGGCTTGGATTTCTATAAGAGATACAAATACTAAATTATTATTTTAAAAACAGCACAAAAGGAAACTCACCCTAACTGTAAAGTAATTGTGTGTTTTGAGACTATAAATATCCCTTGGAGAAAAGCCTTGTTTGCATCCCCACCCTCTGAGAAAAAGATCCTCAGACAATCCATGTGCTTCTCTTGCCTTCATTCCACCGGAGTCTGTCTCATACCCAACCAGATTTCAGTGGAGTGAAGTTCAGGAGGCATGGAGCTGACAACCATGAGGCCTCGGCAGCCACCGCCACCACGAATTC-3' |

(SEQ ID NOs: 27 and 28, respectively)

To construct luciferase reporter plasmids, the oligonucleotide pairs listed in Table 6 were allowed to anneal and cloned into XhoI-NotI site of psiCHECK2 (Promega) to give psiCHECK2-T141, psiCHECK2-T200c, and psiCHECK2-T205. To construct luciferase reporter plasmids for in vivo imaging system, pTK4.12 (Haraguchi T. et al., Nucleic Acids Res. 2009; 37(6): e43) was partially digested with ClaI and then digested with HindIII. These 0.4-kb ClaI-HindIII fragment and 4.0-kb fragment of pLSP were ligated. The plasmid was digested with XhoI, followed by the treatment with Klenow fragment, and then was digested with XbaI. Furthermore, pIRESneo was digested with Bg/11, followed by the treatment with Klenow fragment, and then was digested with XbaI. These 4.3-kb and 1.5-kb fragments were ligated. The product was digested with ClaI and XbaI, and the 3.5-kb fragment was cloned into ClaI-XbaI site of pLSP to give pLenti-SV40-FLuc-IRES-Neo.

TABLE 6

| Primer | Sequence |
|---|---|
| psiCHECK2-T141 s | 5'-TCGAGCCATCTTTACCAGACAGTGTTAGC-3' |
| psiCHECK2-T141 a | 5'-GGCCGCTAACACTGTCTGGTAAAGATGGC-3' |
| psiCHECK2-T200c s | 5'-TCGAGTCCATCATTACCCGGCAGTATTAGC-3' |
| psiCHECK2-T200c a | 5'-GGCCGCTAATACTGCCGGGTAATGATGGAC-3' |
| psiCHECK2-T205 s | 5'-TCGAGCAGACTCCGGTGGAATGAAGGAGC-3' |
| psiCHECK2-T205 a | 5'-GGCCGCTCCTTCATTCCACCGGAGTCTGC-3' |

(SEQ ID NOs: 29 to 34 from the top)

Virus Introduction

SUM149PT cells were seeded at $1 \times 10^5$ cells/well in a 6-well plate in SUM149PT medium. 24 hours later, the cells were introduced with TuD RNA virus stock ($3 \times 10^5$ TU) or miRNA virus stock ($3 \times 10^5$ TU) in the presence of 8 μg/ml Polybrene. Another 24 hours later, the medium was replaced with SUM149PT medium supplemented with puromycin (1 μg/ml) or blasticidin (10 μg/ml). Following 10 days of selection, blasticidin was removed from the medium.

Transfection and Luciferase Assay

On the day before transfection, cells were seeded at $1 \times 10^5$ cells/well in a 24-well plate in SUM149PT medium. SUM149PT cells were transfected in triplicate with 200 ng of dual luciferase target reporter plasmid using PEI-MAX (FIG. 22). All assays were performed 48 hours after the transfection using Dual-Luciferase Assay (Promega) with Glomax (Promega).

Tumorsphere Assay

SUM149PT cells were sorted by FACS Aria (BD), and seeded at a single cell/well in an ultra-low attachment round bottom 96-well plate (Corning) in MammoCult Medium (STEMCELL Technologies). Hydrocortisone was added every three days.

RNA Preparation and Quantitative RT-PCR

Total RNA was prepared from cells using Direct-zol (Zymo Research). Then, the first strand cDNA was synthesized using PrimeScript RT reagent Kit with gDNA Eraser (TAKARA). Real-time RT-PCR was performed with StepOne real-time PCR system (Life Technologies) using SYBR Select Master Mix (Life Technologies) as a reporter. The data were normalized to GAPDH expression. Primer sequences used in the real-time RT-PCR are listed in Table 7.

TABLE 7

| Primer | | Sequence |
|---|---|---|
| Zeb1 | F+ | 5'-CACACCAGAAGCCAGTGGTC-3' |
| Zeb1 | R+ | 5'-AACTGCACAGGGAGCAACTA-3' |
| Zeb2 | F | 5'-ACATCAAGTACCGCCACGAG-3' |
| Zeb2 | R | 5'-GCATTTGGTGCTGATCTGTCC-3' |
| TGFβ2 | F | 5'-GCCTGAACAACGGATTGAGC-3' |
| TGFβ2 | R | 5'-ATCGAAGGAGAGCCATTCGC-3' |
| Pri-miR-200c/141 | F | 5'-GCAGTAACCTTCAGGGAGCC-3' |
| Pri-miR-200c/141 | R | 5'-GATTCGTCCCCCATCCAGAG-3' |
| ESRP1 | F | 5'-TGTAAGTGAGGAGCACCGAG-3' |
| ESRP1 | R | 5'-TGGAGAGAAACTGGGCTACC-3' |
| ESRP2 | F | 5'-GATTGCAGGGGGCACATCACTA-3' |
| ESRP2 | R | 5'-CAAAGAGGGCGAAGGCATCA-3' |
| pan-CD44 | F | 5'-TGGCGCAGATCGATTTGAATA-3' |
| pan-CD44 | R | 5'-CCGTCCGAGAGATGCTGTAG-3' |
| CD44v8-10 | F | 5'-TCTTTCAATGACAACGCAGCA-3' |
| CD44v8-10 | R | 5'-TTGGGTCTCTTCTTCCACCTG-3' |
| CD44s | F | 5'-TACACCCCATCCCAGACGAA-3' |
| CD44s | R | 5'-GAATGTGTCTTGGTCTCTGGTAGC-3' |
| ESA | F | 5'-GCTGGAATTGTTGTGCTGGTTA-3' |
| ESA | R | 5'-AAGATGTCTTCGTCCCACGC-3' |
| CDH1 | F | 5'-ACGCCGAGAGCTACACGTTC-3' |
| CDH1 | R | 5'-TGAATCGGGTGTCGAGGGAA-3' |
| CDH2 | F | 5'-ATTTCCATCCTGCGCGTGAA-3' |
| CDH2 | R | 5'-AAAAGTTGTTTGGCCTGGCG-3' |
| CDH3 | F | 5'-CACCAACCATCATCCCGACA-3' |
| CDH3 | R | 5'-TCTGTGTTAGCCGCCTTCAG-3' |
| Vimentin | F | 5'-AGGAGGAAATGGCTCGTCAC-3' |
| Vimentin | R | 5'-AGGCAGAGAAATCCTGCTCTC-3' |
| Twist1 | F | 5'-GGAGTCCGCAGTCTTACGAG-3' |
| Twist1 | R | 5'-TGGAGGACCTGGTAGAGGAA-3' |
| Snail | F | 5'-GGACCCACACTGGCGAGAAG-3' |
| Snail | R | 5'-ACATTCGGGAGAAGGTCCGA-3' |
| Slug | F | 5'-CGAACTGGACACACATACAGTGA-3' |
| Slug | R | 5'-GGAATGGAGCAGCGGTAGTC-3' |
| CD24 | F | 5'-ACTTTCCTCCTGAGGCTTTGG-3' |

TABLE 7-continued

| Primer | | Sequence |
|---|---|---|
| CD24 | R | 5'-TGCTTGGATCTGGGGGTAGA-3' |
| GAPDH | F | 5'-ACTTTGTCAAGCTCATTTCCTG-3' |
| GAPDH | R | 5'-CTCTCTTCCTCTTGTGCTCTTG-3' |

F+; Forward primer
R+; Reverse primer
(SEQ ID NOs: 35 to 72 from the top)

Cell Proliferation Assay

SUM149PT cells were seeded at 1×10³ cells/well in a 96-well plate in SUM149PT medium. The metabolic activity of cells was assessed every 24 hours with GLOMAX according to manufacturer's instructions using CellTiter GLO (Promega), which is a luminescent ATP-based assay system.

Establishment of Tetracycline-Inducible Cell Lines

SUM149PT cells were seeded at 1×10⁵ cells/well in a 6-well plate and introduced with a virus stock (<1×10⁴ TU) of pXL001 (Addgene plasmid 26122) in the presence of 8 µg/ml Polybrene. Puromycin selection (1 µg/ml) was started 24 hours after the introduction. Following 10 days of selection, Puromycin was removed from the medium. These cells were seeded at 1×10⁵ cells/well in a 6-well plate and introduced with a virus stock (3×10⁵ TU) of pLSB or pLSB-Tete7SK-TuD-141/200c in the presence of 8 µg/ml Polybrene. Blasticidin selection (10 µg/ml) was started 24 hours after the introduction. Following 10 days of selection, blasticidin was removed from the medium. An ESA+ fraction of the cells was sorted by FACS Aria (BD) without Doxycycline. Cells sorted from pLSB-introduced cells were named SUM149PT-TetOn-Empty. Four days after sorting, the cells introduced with pLSB-Tete7SK-TuD-141/200c were cultured in the presence of Doxycycline (1 µg/ml) for 13 days, and ESA− cells were selected by FACS sorting. Then, these cells were cultured without Doxycycline for 15 days, and ESA+ cells were selected by FACS sorting. The cells were named SUM149PT-TetOn-TuD-141/200c.

Animal Experiments

Female BALB/c nude mice were purchased from Japan SLC, and all experiments were carried out using 6-week-old mice. Cells were suspended in SUM149PT medium and combined with an equal volume of Matrigel (BD). The cells were injected into mammary fat pads. Tumor volume was measured with a digital caliper. VivoGlo Luciferin (Promega) was injected at 150 mg/kg subcutaneously to mice which were transplanted with SUM149PT cells introduced with luciferase expression virus vectors. Luminescent images of the whole body were photographed by IVIS 100 (Xenogen).

In in vivo tetracycline induction experiments, 5×10⁵ cells were injected into mammary fat pads. The mice were maintained by ad libitum feeding with water (control) or water containing 2 mg/ml Doxycycline and 5% sucrose from 25 days after transplantation. Doxycycline water was filled in opaque bottles and changed twice a week.

Statistical Analysis

Data of luciferase reporter was analyzed by two-sided Student's t test. Tumor volume data were analyzed by two-way ANOVA using Tukey post-hoc test. P value is considered significant when p value<0.05. In line graphs of tumor volume, data are shown as mean+SD. In other graphs, data are shown as mean±SD.

[Example 2-1] Separation of Tumor Cell Subpopulations Using Surface Markers ESA and CD24

First, the expression level of ESA and CD24 in original cell cultures of triple negative-breast cancer line SUM149PT was assessed by FACS. The result showed that 99% or more of SUM149PT cells were ESA(+) cells and CD24 expression showed a broad distribution (FIG. 10-1A). ESA(−) cells from the cells were sorted and cultured for 28 days, followed by FACS analysis. The proportion of ESA(−) cells was increased to 20%. The CD24 expression level in the cells also showed a broad distribution, irrespective of the state of ESA expression (FIG. 10-1A). Since ESA/CD49f and CD44/CD24 can also be used as a marker to separate the subpopulations of SUM149PT, the same cell cultures as shown in FIG. 10-1A were sorted using these two pairs of surface markers. CD49f (FIG. 10-1A) and CD44 (data not shown) did not significantly separated cell populations under the condition described in Examples herein. Thus, the present inventors decided to use ESA/CD24 markers for the separation in subsequent analyses. When ESA(+)/CD24(+), ESA(+)/CD24(−), ESA(−)/CD24(+), and ESA(−)/CD24(−) cells were isolated from the cells by cell sorting and allowed to proliferate, the four types of subpopulations exhibited different cellular morphologies (FIG. 10-1B). In particular, ESA(+) cells showed a cuboidal shape whereas ESA(−) had more elongated and spindle-shape.

A single cell was isolated from each FACS fraction and cultured for one month, and this yielded clonal cultures with an ESA/CD24 expression pattern assessed by FACS to be almost identical to that of the originally isolated cell (three clones for each fraction) (FIGS. 10-2C and 19). Importantly, when each cell clone was cultured for a period longer than two months, cell types with different phenotypes, which can be found in other subpopulations with a different CD24 or ESA expression level, began to increase (FIG. 10-2C). Since these cells are each derived from a single cell, the transition cannot be interpreted as due to contamination during the sorting process. These results suggest that SUM149PT cells can exist in any of the four cellular states depending on expression conditions of ESA and CD24, which states are stochastically interchangeable at various frequencies.

[Example 2-2] High Tumorigenicity of ESA(+) Cells

To avoid potential problems when analyzing clonal cells, 10⁴ or more cells were collected from each of subpopulations ESA(+)/CD24(+), ESA(+)/CD24(−), ESA(−)/CD24(+), and ESA(−)/CD24(−) separated by FACS (FIG. 11-1A) from cultures similar to those shown in FIG. 10-1A (lower panel). When SUM149PT cells are injected into mouse mammary glands, the cells form non-metastatic primary tumor in vivo. Then, cells from these four subpopulations prepared above were injected into mammary fat pads of nude mice. Within four weeks after injection of 30,000 cells of ESA(+) subpopulation, the host mice developed visible breast cancer (FIG. 11-2B). On the other hand, ESA(−)/CD24(−) cells formed small tumor at later stages and ESA(−)/CD24(+) cells formed no tumor. When 300 cells were injected, ESA(+) cells still formed tumor whereas ESA(−) cells formed no tumor (FIG. 11-2C). It was unexpected that a major cell fraction with epithelial characteristics in original SUM149PT, not a minor cell population with mesenchymal characteristics, exhibited traits of cancer-initiating cells (cancer stem cells).

ESA(+)/CD24(+), ESA(+)/CD24(−), ESA(−)/CD24(+), and ESA(−)/CD24(−) subpopulations were purified through four consecutive rounds of FACS every six weeks, and injected into mouse mammary fat pads in the same manner as described on the subpopulations directly sorted from the original mixed cultures (see FIG. 10-1A). Unlike the subpopulations sorted only once from the original mixed cultures, both of the long-term cultured ESA(−) subpopulations had completely lost their tumorigenicity at the injection of either 300 or 30,000 cells (FIGS. 20A, B). When compared to the cultures purified consecutively four times, ESA(−) cells (ESA(−)/CD24(−) in particular) sorted from the original mixed cultures (FIG. 10-1A) had a much higher frequency of transition from ESA(−) to ESA(+) (FIG. 11-1A). This suggests that the ESA(+) cells converted from ESA(−) are functional stem-like cells that contribute to tumor formation by this fraction.

It is noteworthy further that the tumorigenicity of ESA (+)/CD24(−) subpopulation prepared by consecutive sorting was much higher than that of ESA(+)/CD24(+) obtained by consecutive sorting. These observations suggest that the rapid transition from ESA(+)/CD24(+) to ESA(+)/CD24(−) observed in the subpopulations directly sorted from the original mixed cultures may make the fraction of cancer-initiating cells less detectable and that cancer-initiating cells (cancer stem cells) are mainly included in ESA(+)/CD24(−) subpopulation. The subsequent Examples focus on subpopulations directly sorted from the original mixed cultures to reproduce/observe the cellular properties and behaviors in their dynamic interconversion.

[Example 2-3] Enhancement of miRNA in ESA(+) Cells

Based on the assumption that a particular subset of miRNAs modulates the equilibrium among phenotypes in subcellular populations, these four subpopulations were analyzed for their miRNA expression pattern immediately after cell sorting. The expression level of all members of miR-200 family (miR-200a, miR-200b, miR-200c, miR-141, and miR-429) was clearly different among subpopulations (FIG. 21). All members of the miR-200 family were expressed at much higher levels in ESA(+) cells than in ESA(−) cells, irrespective of the state of CD24 expression. All of the five members of miR-200 family are known to be produced from either of the two chromosomal loci: miR-200b, miR-200a, and miR-429 are clustered on chromosome 1 while miR-200c and miR-141 form a group on chromosome 12, and each cluster is expressed as a polycistronic transcript. Since the expression level of miR-200c and miR-141 was higher than that of the others (FIG. 21), the miR-200c/miR-141 locus was considered to be a major site for the production of miR-200 family members in the cell line. Meanwhile, the expression of the two loci seemed to be regulated in the same manner among the subpopulations. Importantly, the seed sequence is different between [miR-141, -200a] and [miR-200c, -200b, -429], and their mRNA-binding properties are different from each other in the miR-200 family. Thus, miR-141 and miR-200c were used to modulate the two subgroups of the seed sequences.

The four subpopulations were transfected with luciferase reporters designed for the respective miRNAs (T141 and T200, FIG. 22) to confirm that the reporter activities are consistent with the amounts of the miRNAs (FIG. 12A). From the observations described above, the expression of the miR-200 family was predicted to support the cellular transition from ESA(−) to ESA(+) if these miRNAs had a causative effect on the cellular equilibrium.

To modulate the endogenous activities of miR-205, -141, and -200c in each of the four subpopulations, a miRNA expression lentiviral vector or TuD RNA expression lentiviral vector was introduced into a mixed cell population similar to that shown in FIG. 10-1A (lower panel). Two days after the introduction, the vector-introduced cells were sorted into four subpopulations. To assess the effect of the vectors, all stable vector-introduced cells were allowed to proliferate for 19 days and then transfected with the same luciferase reporters as described above (FIGS. 12B, C, D). Introduction of miR-205 vector into ESA(+)/CD24(−), ESA(−)/CD24(+), and ESA(−)/CD24(−) increased the activity of miR-205 (reduced the luciferase activity) relative to that into ESA(+)/CD24(+), while introduction of TuD-205 into ESA (+)/CD24(+) reduced the activity of miR-205 to a level comparable to that into ESA(+)/CD24(−). Introduction of miR-141 or miR-200c expression vector increased the miRNA activity in ESA(−) cells to a level comparable to or slightly lower than the corresponding endogenous level in ESA(+) cells. Meanwhile, the corresponding TuD RNA expression lentiviral vector, when introduced into ESA(+) cells, efficiently inhibited the activity of each miRNA.

FACS analysis of the vector-introduced cells after four weeks of proliferation (FIG. 23) found a larger population at the ESA(−) fraction, when TuD-200c or TuD-141 was introduced into ESA(+)/CD24(+) or ESA(+)/CD24(−) cells. The larger population in ESA(−)/CD24(+) or ESA(−)/CD24 (−) cells introduced with miR-200c expression lentiviral vector was converted to ESA(+) cells, while the degree of conversion by exogenous miR-141 expression was lower (FIG. 23).

The results described above revealed that modulation of miR-200c and -141 in the subpopulations was useful to change the equilibrium among the subpopulations.

[Example 2-4] Promotion of Transition from ESA (−) to ESA(+) by miR-141 and -200c, and Promotion of Transition from ESA(+) to ESA(−) by the Inhibition of miR-141 and -200c The interconversion that is induced by modulating the functional level of miR-200c or miR-141 alone is evident but still remains partial. This is assumed to reflect the previous observation that targets of miR-200c and miR-141 significantly overlap one another but there are also different target genes between the two miRNAs (Bracken et al., EMBO J. 33: 2040-20506, 2014). Thus, both of them were expressed or inhibited at the same time using a single vector, and the effect was assessed. To achieve simultaneous high-level expression, miR-141 and miR-200c expression units were placed in tandem in a lentiviral vector (miR-141+miR-200c expression vector). Furthermore, a lentiviral vector that expresses a hybrid-type TuD molecule with two miRNA-binding sites composed of sequences complementary to miR-141 and miR-200c, respectively, was used to achieve simultaneous inhibition (Example 1). The vectors were introduced into the mixed cell population described above, in which a luciferase gene expression vector had been introduced in advance for subsequent in vivo analyses. Two days after introduction of each vector, the vector-introduced cells were sorted into four subpopulations and allowed to proliferate for three weeks. The expression level of ESA and CD24 was determined by FACS analysis (FIG. 13). Almost all ESA(−)/CD24(+) and ESA(−)/CD24(−) cells introduced with the miR-141+miR-200c expression vector were converted to ESA(+) cells. Furthermore, about 80% of ESA(+)/CD24(+) and ESA(+)/CD24(−) cells introduced with TuD-141/200c were converted to ESA(−) cells. ESA(+)/CD24(+) and ESA(+)/CD24(−) populations were sorted and allowed to proliferate for 16 days, and ESA(−) cells were isolated by sorting from each of these parallel cultures. No conversion into ESA(+) cells was detected for ESA(−)/CD24(+) and ESA(−)/CD24(−) cells introduced with TuD-141/200c, unlike cells introduced with an empty vector. This suggests that TuD RNA functioned preventively even in the cells which originally contain only a small amount of target miRNAs and stochastically undergo induction later.

[Example 2-5] Loss of Tumorsphere Forming Activity by Suppressing the Activity of miR-200 Family Tumorsphere (mammosphere) formation is often used to assess cancer stem cell traits. Thus, all vector-introduced cells prepared as described above were sorted as single cells, which were then allowed to proliferate in mammosphere assay medium using low-attachment plates. As shown in FIG. 14A, all ESA(+) cells introduced with an empty vector formed typical mammospheres at a frequency higher than 10%; however, in ESA(+) cells introduced with TuD-141/200c vector, the mammosphere formation was dramatically reduced (about 2%) to the level comparable to that of ESA(−) cells introduced with an empty vector. When miR-141/200c vector was introduced into ESA(−) cells, the mammosphere formation frequency was increased to a level greater than 10%. Importantly, these observations were unaffected by the expression level of CD24. Furthermore, it is noteworthy that all vector-introduced cells assessed here exhibited no significant difference in the growth rate even when they were measured by monolayer culture (FIG. 24). Thus, the observed conversion between subpopulations cannot be interpreted in terms of a difference in growth rate between distinct states. These findings, when viewed as a whole, show that the high-level expression of miR-200c is deeply correlated with the mammosphere formation activity.

In the course of assay, it was found that like ESA(+) cells introduced with TuD-141/200c vector, ESA(−) cells introduced with an empty vector formed sheet-like colonies in low-attachment plates (FIG. 14B).

Since the frequency of sheet-like colony formation was high in ESA(−) cells, the biological property represented by the sheet-like colony may be correlated with non-epithelial traits. Furthermore, it is noteworthy that ESA(−) cells introduced with miR-200c/141 formed colonies of intermediate type as well as colonies of the two types (FIG. 14A, B), suggesting that the cells are a mixture of cell populations that are different in the state of conversion between epithelial and non-epithelial cell types.

[Example 2-6] Changes in Gene Expression Profiles Induced by Inhibition of miRNA200 Family To obtain more information on each of the four subpopulations, real-time RT-PCR was performed (FIG. 16) to quantify Zeb1, Zeb2, and TGFβ2 mRNA (which are well known targets of the miR-200 family); transcripts such as ESRP1 (FIG. 15) and CDH1 (E-Cad) (FIG. 16) mRNA (which are targets of transcriptional suppressors Zeb1/Zeb2); and transcripts such as ESA and CDH3 (epithelial markers), and vimentin and CDH2 mRNAs (mesenchymal markers). When the level of RNA transcripts in the cells of each subpopulation introduced with an empty vector was compared, ESA(+) cells expressed high levels of ESA, CDH1, CDH3, and ESRP1 (epithelial markers) while ESA (−) cells expressed Zeb1, Zeb2, vimentin, and CDH2 at high levels (FIGS. 15 and 16). Meanwhile, the expression level of Snail, Slug, and Twist, which have often been reported as molecular switches that serve as a key for promoting EMT, was not significantly different between ESA(+) and ESA(−) cells in this cell system (FIG. 16). These results show that the spontaneous interconversions between ESA(+) and ESA (−) subpopulations observed with parent SUM149PT can be each interpreted as typical EMT or MET, thus demonstrating the epithelial plasticity of the cell line. Importantly, endogenous pri-miR-200c/141 and Zeb1, which have been reported to form double negative feedback loop, stochastically changed in an interconvertible manner and the cells existed as ESA(+) cells (major subpopulation) containing pri-miR-200c/141 transcripts at high levels and a small amount of Zeb1 mRNA or as ESA(−) cells (minor subpopulation) containing pri-miR-200c/141 and a large amount of Zeb1.

When the activity of the miR-200 family was inhibited in the ESA(+) subpopulation using a vector that expresses TuD-141/200c, the epithelial phenotype changed to a mesenchymal phenotype, which was highly similar to the phenotype of the ESA(−) subpopulation introduced with an empty vector. Meanwhile, when the miR-200c+miR-141 vector was introduced into the ESA(−) subpopulation, the mesenchymal phenotype changed to an epithelial-like phenotype, which was similar to the phenotype of the ESA(+) subpopulation introduced with an empty vector, except for vimentin and CDH2 mRNAs. The expression level of vimentin and CDH2 mRNAs was almost negligible in the ESA(+) subpopulation but they were expressed at significant levels in the ESA(−) subpopulation introduced with the miR-200c+miR-141 vector. These two genes have been reported to be positively regulated in an indirect manner by Zeb-1/Zeb-2. This suggests that the observation described above may partly reflect that the cells are a mixture of cell populations that are different in the state of conversion between epithelial and non-epithelial cell types.

[Example 2-7] Tumor-Suppressing Effect by Inhibition of miRNA200 Family, which is Exerted on the Entire Subpopulations of Tumor Cells Cells introduced with miR-141+miR-200c expression lentiviral vector or TuD-141/200c expression lentiviral vector prepared as described above were injected into mammary fat pads of nude mice to assess their tumorigenicity (FIG. 17). TuD-141/200c significantly reduced the tumorigenicity of ESA(+)/CD24(+) and ESA(+)/CD24(−) cells. Since ESA (−) fractions sorted from the cells did not significantly form tumor, their remnant tumorigenicity is assumed to originate from cell fractions which have not completely been converted to ESA(−). In contrast, ESA(−)/CD24(+) and ESA (−)/CD24(−) cells introduced with the miR-141+miR-200c vector formed tumor at much higher frequencies than the cells introduced with an empty vector, which formed small tumor at later stages. Furthermore, ESA(−)/CD24(+) and ESA(−)/CD24(−) cells introduced with the TuD-141/200c vector formed no tumor.

When the luciferase activity of tumor cells in individual mice was imaged by IVIS, metastasis was not detected in all cases on day 57. Furthermore, IVIS analysis detected cells of small cancer at the injection sites only in mice transplanted with ESA(−)/CD24(+) or ESA(−)/CD24(−) cells introduced with an empty vector; however, in mice introduced with TuD-141/200c, no tumor was formed even on day 127. Since TuD-141/200c completely abolished the conversion from ESA(−)/CD24(+) cells or ESA(−)/CD24(−) cells to ESA(+) cells, ESA(+) cells derived from ESA(−)/CD24(+) cells or ESA(−)/CD24(−) cells introduced with an empty vector were the possible cause of the tumorigenicity and were assumed to contain tumor initiating cells that were stochastically generated from ESA(−) non-tumor initiating cells. The result that TuD-141/200c also inhibited the tumorigenicity in a preventive manner even in cells expressing almost no miR-200c and -141, which are targets of TuD-141/200c, supports that miR-200c and -141 are key factors for tumorigenicity.

[Example 2-8] Regression of Formed Tumor by TuD-141/200c

To further demonstrate the therapeutic applicability of TuD-141/200c, a mouse model system that can precisely control TuD-141/200c expression was constructed using a lentiviral vector system (Example 1) that carries Dox (tetracycline derivative)-dependent TuD expression unit (Tet-ON). The detail of preparation of SUM149PT cells carrying a Tet-inducible TuD-141/200c vector or an empty vector is shown in FIG. 25. The cells were injected into mice on day 25. When tumor with a size of 42-60 mm$^3$ was formed, water containing Dox (doxycycline) was given to a half of the mice (five heads in each). As a result, tumor size in mice with Dox-inducible TuD-141/200c was reduced only when the Dox water was given (FIG. 18). The reduction of tumor size in these mice lasted for 14 days after administration of the Dox water. Although the tumor size began to increase at later stages, the rate of increase was significantly lower as compared to the mice that were continuously given Dox-water; thus, the simultaneous inhibition of miR-200c and -141 was confirmed to exhibit a significant therapeutic effect on already-formed tumor as well.

[Example 3] Application of miR-200 Family Inhibition Therapy to Cancers Derived from Other Organs Analyses were performed using lung cancer cells to confirm whether the change in the expression pattern of stem cell gene markers in tumor, the decrease in the tumorsphere formation efficiency, and the reduction of in vivo tumor formation in mice by inhibiting the miR-200 family, which were observed with the breast cancer cell line, are also induced with cancer cells derived from other organs.
<Materials and Methods>
Cell Culture Non-small cell lung cancer cell lines H596, A-427, and HCC827 were obtained from ATCC. H596 cells were cultured at 37° C. in DMEM supplemented with 10% fetal bovine serum (FBS). A-427 cells were cultured at 37° C. in EMEM supplemented with 10% fetal bovine serum (FBS). HCC827 cells were cultured at 37° C. in RPMI1640 supplemented with 10% fetal bovine serum (FBS).
Virus Introduction H596 cells were seeded at 1×10$^5$ cells/well in a 6-well plate in DMEM. 24 hours later, cells were introduced with each TuD RNA virus stock (3×10$^5$ TU) in the presence of 8 μg/ml Polybrene. Another 24 hours later, the culture medium was changed with DMEM supplemented with puromycin (1 μg/ml). Following seven days of selection, puromycin was removed from the medium. A-427 cells were seeded at 1×10$^5$ cells/well in a 6-well plate in EMEM. 24 hours later, the cells were introduced with each TuD RNA virus stock (3×10$^5$ TU) in the presence of 8 μg/ml Polybrene. Another 24 hours later, the culture medium was changed with EMEM supplemented with puromycin (1 μg/ml). Following seven days of selection, puromycin was removed from the medium.

HCC827 cells were seeded at 1×10$^5$ cells/well in a 6-well plate in RPMI1640. 24 hours later, the cells were introduced with each TuD RNA virus stock (3×10$^5$ TU) in the presence of 8 μg/ml Polybrene. Another 24 hours later, the culture medium was changed with RPMI1640 supplemented with puromycin (1 μg/ml). Following seven days of selection, puromycin was removed from the medium.
Antibody Staining, FACS Analysis and MACS Analysis H596, A-427, and HCC827 cells were stained with αESA-APC (324208, BioLegend), αCD24-PE (311106, BioLegend), and αCD44-FITC (338804, BioLegend), and analyzed by FACS Calibur (BD) or MACSQuant (Miltenyi Biotec).
Tumorsphere Assay A-427 and HCC827 cells introduced with virus were sorted by FACS Aria (BD) and were seeded at a single cell/well in an ultra-low attachment round-bottomed 96-well plate (Corning) in Phenol red-free DMEM/F12 (Life Technologies) supplemented with 20 ng/ml human bFGF (Sigma-Aldrich), 20 ng/ml human EGF (Sigma-Aldrich), 1× B27 (Life Technologies), and 4 μg/ml heparin (Stem cell Technology). Human bFGF, human EGF, and heparin were added every three days.
Animal Experiments Female BALB/c nude mice were purchased from Japan SLC, and all experiments were carried out using 6-week-old mice. H596 cells introduced with virus were suspended in DMEM, and combined with an equal amount of Matrigel (BD). The cells were injected in the right flank. Tumor volume was measured with a digital caliper.
Statistical Analysis Tumor volume data were analyzed by two-way ANOVA using Tukey post-hoc test. P value is considered significant when p value<0.05. In line graphs of tumor volume, data are shown as mean+SD. In other graphs, data are shown as mean±SD.

[Example 3-1] Promotion of Transition from ESA(+) to ESA(−) in Non-Small Cell Lung Cancer Cell Lines by Inhibition of miR-141 and -200c A lentiviral vector that expresses a hybrid-type TuD molecule with two miRNA-binding sites composed of sequences complementary to miR-141 and miR-200c, respectively, was used to simultaneously inhibit miR-141 and miR-200c (Example 1). The vector was introduced into H596 cells, A-427 cells, and HCC827 cells, and after puromycin selection, the cells were allowed to proliferate for two to three weeks. The expression level of ESA, CD44, and CD24 was determined by FACS and MACS analyses. As CD44 was more excellent than CD24 for separating cell populations of non-small cell lung cancer lines, the present inventors decided to use ESA/CD44 marker in subsequent analyses (FIG. 26).

ESA(+) cells that originally accounted for about 1% in H596 cells almost disappeared from H596 cells introduced with TuD-141/200c. In A-427 cells introduced with TuD-141/200c, about 80% of ESA(+) cells were converted to ESA(−) cells. In HCC827 cells introduced with TuD-141/200c, about 40% of ESA(+) cells were converted to ESA(−) cells.

[Example 3-2] Loss of Tumorsphere Forming Activity by Inhibiting the Activity of miR-200 Family Tumorsphere (sphere) formation is often used to assess cancer stem cell traits. Then, A-427 cells introduced with TuD-NC (negative control) or TuD-141/200c were sorted as single cells and allowed to proliferate in tumorsphere assay medium using low-attachment plates. As shown in FIG. 27A, A-427 cells introduced with TuD-NC vector formed typical tumorspheres at a formation efficiency of about 6% whereas when TuD-141/200c vector was introduced, the tumorsphere formation efficiency of A-427 cells was reduced to less than 1%.

Furthermore, also in HCC827 cells, the reduction of tumorsphere formation rate was observed when TuD-141/200c was introduced into the cells, as compared to when the cells were introduced with the negative control TuD vector.

ESA(+) cells and ESA(−) cells from HCC827 cells without virus introduction, HCC827 cells introduced with TuD-NC (negative control), and ESA(+) cells and ESA(−) cells from HCC827 cells introduced with TuD-141/200c were each sorted as a single cell, and were allowed to proliferate in tumorsphere assay medium using low-attachment plates. The result showed that ESA(+) cells from HCC827 cells without virus introduction formed tumorspheres while the ESA(−) cells formed no tumorspheres. Likewise, cells of the ESA(−) fraction that had been increased by introduction of TuD-141/200c vector formed no tumorspheres. This suggests that cells with tumorsphere-forming ability (cancer stem cells) are present in the ESA(+) cell population.

These findings, when viewed as a whole, show that the high-level expression of miR-200c is deeply correlated with the tumorsphere formation activity also in lung cancer cells and that tumor can be suppressed effectively by inhibiting the miR-200 family.

[Example 3-3] Tumor-Suppressing Effect by Inhibition of miRNA200 Family, which is Also Exerted on Cells of Non-Small Cell Lung Cancer Cell Line H596

H596 cells introduced with the TuD-141/200c expression lentiviral vector were injected into the right flank of nude mice to assess their tumorigenicity (FIG. 28). H596 cells introduced with TuD-NC showed tumorigenicity whereas H596 cells introduced with TuD-141/200c formed no tumor even two and a half months after transplantation.

INDUSTRIAL APPLICABILITY

The present invention provides methods for suppressing tumors by inhibiting miRNAs. The present invention provides novel therapeutic methods against tumors.

The invention claimed is:

1. A method for suppressing a tumor, which comprises inhibiting both at least one miRNA comprising 5'-AACACUG-3' as a seed sequence and at least one miRNA comprising 5'-AAUACUG-3' as a seed sequence in a subject, thereby suppressing a tumor in the subject, wherein the inhibition comprises using a Tough Decoy (TuD) comprising the nucleotide sequence of SEQ ID NO: 73.

2. The method of claim 1, wherein the tumor is a colorectal cancer.

3. The method of claim 1, wherein the tumor is a lung cancer.

4. The method of claim 1, wherein the tumor is a triple-negative breast cancer (TNBC).

5. The method of claim 1, wherein the inhibition reduces tumorigenicity of a group of cells of the tumor.

6. The method of claim 1, wherein the inhibition suppresses transition of a group of cells of the tumor to cells with higher tumorigenicity.

7. The method of claim 1, wherein the inhibition promotes epithelial-mesenchymal transition in the tumor.

8. The method of claim 1, wherein the inhibition inhibits at least miR-200c and miR-141.

* * * * *